(12) United States Patent
Chen et al.

(10) Patent No.: US 12,338,255 B2
(45) Date of Patent: Jun. 24, 2025

(54) BICYCLIC SUBSTITUTED SULFONYLUREA COMPOUNDS AS INHIBITORS OF INTERLEUKIN-1 ACTIVITY

(71) Applicant: Viva Star Biosciences (Suzhou) Co., Ltd., Jiangsu (CN)

(72) Inventors: Ping Chen, Shanghai (CN); Hongjian Zhang, Plainsboro, NJ (US); Fei Jiang, Shanghai (CN); Peihua Sun, Shanghai (CN)

(73) Assignee: Viva Star Biosciences (Suzhou) Co., Ltd., Jiangsu (CN)

( * ) Notice: Subject to any disclaimer, the term of this patent is extended or adjusted under 35 U.S.C. 154(b) by 120 days.

(21) Appl. No.: 18/111,283

(22) Filed: Feb. 17, 2023

(65) Prior Publication Data
US 2023/0279026 A1    Sep. 7, 2023

(30) Foreign Application Priority Data
Feb. 21, 2022  (WO) ................ PCT/CN2022/076992

(51) Int. Cl.
*C07D 519/00*    (2006.01)
(52) U.S. Cl.
CPC .................. *C07D 519/00* (2013.01)
(58) Field of Classification Search
CPC ................................................... C07D 519/00
USPC ........................................................ 514/230
See application file for complete search history.

(56) References Cited

FOREIGN PATENT DOCUMENTS

| WO | WO-2019/034686 A1 | 2/2019 | | |
|---|---|---|---|---|
| WO | WO-2019/079119 A1 | 4/2019 | | |
| WO | WO-2019/092170 A1 | 5/2019 | | |
| WO | WO-2020/018970 A1 | 1/2020 | | |
| WO | WO-2023116812 A1 * | 6/2023 | ............ | A61K 31/40 |

OTHER PUBLICATIONS

Holbrook et al., Neurodegenerative Disease and the NLRP3 Inflammasome, Mar. 10, 2021, Frontiers in Pharmacology, vol. 12, pp. 8-9 (Year: 2021).*
Dobson et al., Editorial: Preventing Multiple Sclerosis, Jul. 20, 2022, Frontiers in Neurology, vol. 13, pp. 1-3 (Year: 2022).*
Varadhachary, Carcinoma of Unknown Primary Origin, 2007, Gastroinest. Cancer. Res., vol. 1(6), pp. 229-235 (Year: 2007).*
Peña-Bautista et al., Stress and neurodegeneration, Jan. 24, 2020, Clinica Chimica Acta, vol. 503, pp. 163-168 (Year: 2020).*
Tao Li et al., Lessons From the Misdiagnosis of Cryopyrin-Associated Periodic Syndrome as an Infection, Dec. 2021, Journal of Clinical Rheumatology, vol. 27, Supplement 3, pp. S485-S487 (Year: 2021).*
WIPO English machine translation of WO 2023116812 A1, Zhang et al. (Year: 2023).*
International Search Report and Written Opinion issued for PCT App No. PCT/US2023/013344 dated May 19, 2023 (16 pages).

* cited by examiner

*Primary Examiner* — Jeffrey H Murray
*Assistant Examiner* — Rilla Marie Samsell
(74) *Attorney, Agent, or Firm* — Foley & Lardner LLP

(57) ABSTRACT

This application relates to novel bicyclic substituted sulfonylurea compounds and analogues, their manufacture, pharmaceutical compositions comprising them, and their use as medicaments for treating a disease associated with modulation of cytokines such as IL-1β and IL-18, modulation of NLRP3, or inhibition of the activation of NLRP3 or related components of the inflammatory process.

19 Claims, No Drawings

BICYCLIC SUBSTITUTED SULFONYLUREA COMPOUNDS AS INHIBITORS OF INTERLEUKIN-1 ACTIVITY

CROSS-REFERENCE TO RELATED APPLICATIONS

This application is a U.S. Utility Application claiming priority under 35 USC 119(a) and 365(a) to PCT International Application No. PCT/CN2022/076992, filed Feb. 21, 2022, the contents of which is incorporated herein by reference in its entirety and for all purposes.

FIELD

This application relates to novel bicyclic substituted sulfonylurea compounds and analogues, their manufacture, pharmaceutical compositions comprising them, and their use as medicaments for treating a disease associated with modulation of cytokines such as IL-1β and IL-18, modulation of NLRP3, or inhibition of the activation of NLRP3 or related components of the inflammatory process.

BACKGROUND

Nucleotide-binding oligomerization domain-like receptors (or NOD-like receptors, NLRs) belong to the family of pattern recognition receptors, acting as intracellular sensors of pathogen-associated molecular patterns (PAMPs) and damage-associated molecular patterns (DAMPs). Accumulating evidence indicates that NLRs play important roles in innate immune responses against infection and cellular damages. Among numerous NOD-like receptors, NLR pyrin domain containing 3 (NLRP3) has been well characterized in the inflammasome formation.

NLRP3 is predominantly expressed in macrophages and a few other cell types with certain degree of tissue specificity. The formation of NLRP3 inflammasome activates caspase-1, which in turn catalyzes proteolytic reactions, releasing pro-inflammatory cytokines such as interleukin-1β (IL-1β) and IL-18 [Nat Rev Immunol. 2013 June; 13(6)]. Inflammasome activation is also associated with pyroptosis, a rapid and pro-inflammatory form of cell death via membrane pore-forming gasdermin D fragments.

It has been shown that dysregulated inflammasome activation participates in the pathogenesis of several human diseases. Most notably, a gain-of-function mutation in NLRP3 causes hereditary diseases characterized by IL-1β-mediated systemic inflammation such as Cryopyrin-associated periodic syndrome (CAPS). In addition, aberrant activation of NLRP3 inflammasomes exacerbates chronic human diseases such as neurodegenerative disorders (multiple sclerosis, AD, and PD), metabolic ailments (atherosclerosis and type 2 diabetes), and inflammatory syndromes (gout flares and osteoarthritis). Recently, roles of NLRP3 in the initiation and progression of cancers have been documented [Nat Immunol. 2021 Mar. 11. doi: 10.1038 s41590-021-00886-5].

Therapeutically targeting the NLRP3/IL-1β innate immunity pathway has been proved to be successful based on the findings from the CANTOS study, where treatment of canakinumab (a monoclonal antibody against IL-1β) resulted in a significantly lower rate of recurrent cardiovascular events, demonstrating a clear benefit of targeting inflammation in high-risk patients with cardiovascular diseases. Targeting NLRP3 activation by small molecules is also feasible as exemplified by MCC950, which directly interacts with the Walker B motif within the NLRP3 NACHT domain, blocking ATP hydrolysis and inhibiting NLRP3 activation and inflammasome formation [Nat Chem Biol. 2019 June; 15(6):556-559].

Therefore, inhibition of the NLRP3/IL-1β innate immunity pathway via small molecule modulators may be a useful and practical approach to treat and prevent hereditary diseases (Cryopyrin-associated periodic syndrome, CAPS), neurodegenerative disorders (multiple sclerosis, AD, and PD), metabolic ailments (atherosclerosis and type 2 diabetes), inflammatory syndromes (gout flares and osteoarthritis), cancer, among other related human diseases.

There is a need to provide compounds with improved pharmaceutical properties and/or those that provide a useful alternative to known compounds, which can help achieve therapeutic efficacy while reducing undesired side effects.

SUMMARY

The present technology provides novel compounds that are effective in inhibiting an inflammasome, such as the NLRP3 inflammasome, as well as in modulating interleukins. In addition, small molecule compounds disclosed herein show good pharmaceutical properties including solubility, ADME (absorption, distribution, metabolism, and excretion), pharmacokinetics, CYP inhibition and other safety profiles, which are useful for obtaining therapeutic efficacy while minimizing undesired properties.

In one aspect, the present technology relates to a compound of Formulae (II)-(IV):

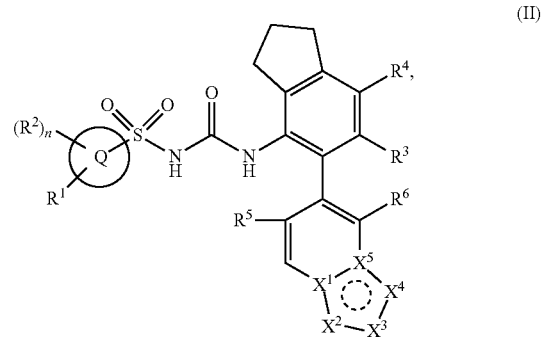

(II)

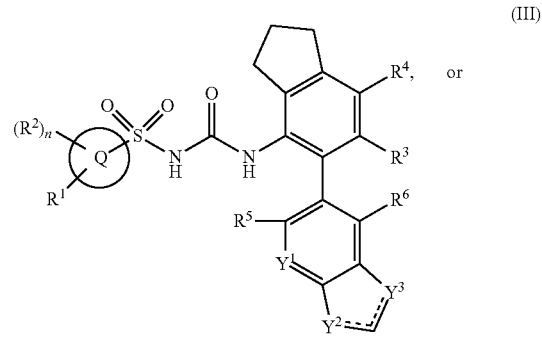

(III) or

-continued

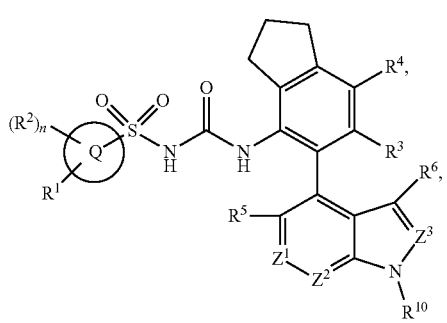

(IV)

or a pharmaceutically acceptable salt, tautomer or stereoisomer thereof,
wherein:
each occurrence of Ring Q is independently

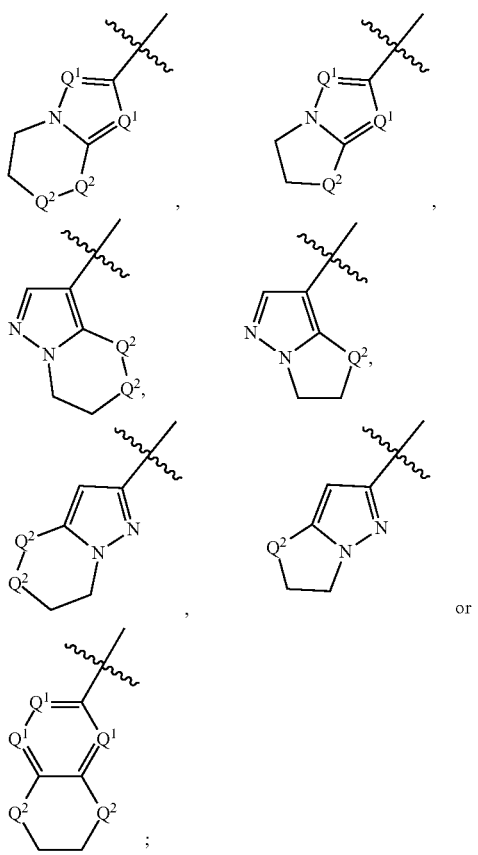

each occurrence of $Q^1$ is independently N or CH, provided that at least one $Q^1$ is N;
each occurrence of $Q^2$ is independently O, S, S(=$O_2$), $CH_2$, or $NR^{12}$,
$X^1$ and $X^5$ are each independently N or C, $X^2$, $X^3$, and $X^4$ are each independently N or $CR^7$, and the dashed circle denotes bonds forming a five-membered aromatic ring; provided that at least two but no more than three of $X^1$, $X^2$, $X^3$, $X^4$ and $X^5$ are N;
$Y^1$ is N or CH, $Y^2$ is N, $NR^8$ or CH, and $Y^3$ is N, $NR^8$ or CH, and

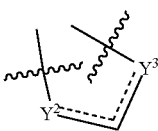

in Formula (III) denotes

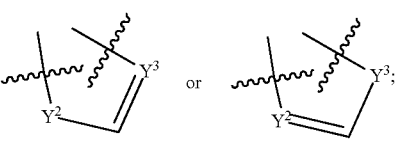

$Z^1$ is N or CH, $Z^2$ is N or $CR^9$, and $Z^3$ is N or CH;
each occurrence of $R^1$ is independently hydrogen, $C_{1-4}$alkyl, halo$C_{1-4}$alkyl, $C_{3-7}$cycloalkyl, $C_{1-4}$alkoxy, $C_{3-7}$cycloalkoxy, oxo (=O), $NR^aR^b$, C(=O)$OR^a$, OC(=O)$R^a$, C(=O)$NR^aR^b$, $NR^bC$(=O)$R^a$, C(=O)NHC(=O)$R^a$, or 4-6-membered heterocyclyl, each of which is optionally substituted with one to three $R^{11}$;
each occurrence of $R^2$ is independently hydrogen, $C_{1-4}$alkyl, halo$C_{1-4}$alkyl, $C_{3-7}$cycloalkyl, halogen, CN, OH, $C_{1-4}$alkoxy, $NR^aR^b$, C(=O)$NR^aR^b$, or 4-6-membered heterocyclyl, each of which is optionally substituted with one to two $R^{11}$, or two $R^2$ groups at geminal position may optionally form a spiro $C_{3-5}$cycloalkyl;
$R^3$, $R^4$, $R^5$ and $R^6$ are each independently hydrogen, halogen, CN, $C_{1-4}$alkyl, or halo$C_{1-4}$alkyl;
each occurrence of $R^7$ is independently hydrogen or $C_{1-4}$alkyl;
each occurrence of $R^8$ is independently hydrogen or $C_{1-4}$alkyl;
each occurrence of $R^9$ is independently hydrogen, $C_{1-4}$alkyl or $C_{1-4}$alkoxy;
each occurrence of $R^{10}$ is independently hydrogen, $C_{1-4}$alkyl, $C_{3-7}$cycloalkyl, or 4-6-membered heterocyclyl optionally substituted with $C_{1-4}$alkyl;
each occurrence of $R^{11}$ is independently hydrogen, $C_{1-4}$alkyl, halo$C_{1-4}$alkyl, halogen, CN, OH, $C_{3-7}$cycloalkyl, $C_{1-4}$alkoxy, $C_{3-7}$cycloalkoxy, $NR^aR^b$, C(=O)$OR^a$, OC(=O)$R^a$, C(=O)$NR^aR^b$, $NR^bC$(=O)$R^a$, C(=O)NHC(=O)$R^a$, or 4-6-membered heterocyclyl;
each occurrence of $R^{12}$ is independently hydrogen, $C_{1-4}$alkyl, halo$C_{1-4}$alkyl, $C_{3-7}$cycloalkyl, $C_{1-4}$alkyl-$C_{3-7}$cycloalkyl, $C_{1-4}$alkyl-$NR^aR^b$, C(=O)$R^a$, C(=O)$NR^aR^b$, or 4-6-membered heterocyclyl optionally substituted with one to three groups selected from $C_{1-4}$alkyl, halo$C_{1-4}$alkyl, $C_{3-7}$cycloalkyl, halogen, CN, OH, $C_{1-4}$alkoxy, $C_{3-7}$cycloalkoxy, or $NR^aR^b$;
each occurrence of $R^a$ and $R^b$ is independently hydrogen, $C_{1-4}$alkyl, $C_{3-5}$cycloalkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl; and
each occurrence of n is independently 0, 1, or 2.

The technology also relates to a pharmaceutical composition comprising a compound of Formulae (I)-(IV), its manufacture and use as medicaments for treating or preventing a disease associated with modulation of cytokines such as IL-1β and IL-18, modulation of NLRP3, or inhibition of the activation of NLRP3 or related components of the inflammatory process. Accordingly, the compounds of Formulae (I)-(IV) are useful for treating or preventing hereditary diseases (Cryopyrin-associated periodic syndrome, CAPS), neurodegenerative disorders (multiple sclerosis, AD, and PD), metabolic ailments (atherosclerosis and type 2 diabetes), inflammatory syndromes (gout flares and osteoarthritis), cancer, among other related human diseases.

DETAILED DESCRIPTION

In one aspect, the present technology provides compounds, and their pharmaceutically acceptable forms, including, but not limited to, salts, hydrates, solvates, isomers, sterioisomers, enantiomers, prodrugs, and isotopically labeled derivatives thereof.

In another aspect, the present technology provides methods of treating and/or managing various diseases and disorders, which comprises administering to a patient a therapeutically effective amount of a compound provided herein, or a pharmaceutically acceptable form (e.g., salts, hydrates, solvates, isomers, sterioisomers, enantiomers, prodrugs, and isotopically labeled derivatives) thereof. Non-limiting examples of diseases and disorders are described herein.

Also provided herein are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, sterioisomers, enantiomers, prodrugs, and isotopically labeled derivatives) thereof.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of ordinary skill in the art to which this specification pertains.

Definitions

As used in the specification and claims, the singular form "a", "an" and "the" includes plural references unless the context clearly dictates otherwise.

As used herein, "agent" or "biologically active agent" or "second active agent" refers to a biological, pharmaceutical, or chemical compound or another moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide active compounds, such as plant or animal extracts, and the like. A skilled artisan can readily recognize that there is no limit as to the structural nature of the agents of this disclosure.

"Administration" of a disclosed compound encompasses the delivery to a subject of a compound as described herein, or a prodrug or other pharmaceutically acceptable derivative thereof, using any suitable formulation or route of administration, as discussed herein.

The term "co-administration," "administered in combination with," and their grammatical equivalents, as used herein, encompasses administration of two or more agents to the subject so that both agents and/or their metabolites are present in the subject at the same time. Co-administration includes simultaneous administration in separate compositions, administration at separate times in separate compositions, or administration in a composition in which both agents are present.

The term "effective amount" or "therapeutically effective amount" refers to that amount of a compound or pharmaceutical composition described herein that is sufficient to affect the intended application including, but not limited to, disease treatment, as illustrated below. In some embodiments, the amount is that effective for detectable inhibition of NLRP3, which, for example, can be determined in a biological assay as described herein. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a response in target cells, e.g., reduction of cell migration. The specific dose will vary depending on, for example, the compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

All methods described herein can be performed in any suitable order unless otherwise indicated herein or otherwise clearly contradicted by context.

As used herein, the terms "treatment", "treating", "palliating" "managing" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a disease, or to a patient reporting one or more of the physiological symptoms of a disease, even though a diagnosis of this disease may not have been made.

The terms "preventing" and "prophylaxis" as used herein refer to administering a pharmaceutical compound or medicament or a composition including the pharmaceutical compound or medicament to a subject before a disease, disorder, or condition fully manifests itself, to forestall the appearance and/or reduce the severity of one or more symptoms of the disease, disorder or condition. The person of ordinary skill in the art recognizes that the term "prevent" is not an absolute term. In the medical art it is understood to refer to the prophylactic administration of a drug to diminish the likelihood or seriousness of a disease, disorder or condition, or a symptom thereof, and this is the sense that such terms are used in this disclosure.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body. In vivo also includes events occurring in rodents, such as rats, mice, guinea pigs, and the like.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. *Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. For example, pharmaceutically acceptable salts include adipate, alginate, ascorbate, aspartate, benzenesulfonate, besylate, benzoate, bisulfate, borate, butyrate, camphorate, camphor sulfonate, citrate, cyclopentane propionate, digluconate, dodecyl sulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In some embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_{1-8}$)alkyl, ($C_{1-12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_{1-2}$)alkylamino($C_{2-3}$)alkyl (such as [3-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a disclosed compound contains an alcohol functional group, a prodrug can be formed by the replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N-($C_{1-6}$)alkoxycarbonylaminomethyl, succinoyl, ($C_{1-6}$)alkanoyl, $\alpha$-amino($C_{1-4}$)alkanoyl, arylacyl, and $\alpha$-aminoacyl, or $\alpha$-aminoacyl-$\alpha$-aminoacyl, where each $\alpha$-aminoacyl group is independently selected from the naturally occurring L-amino acids, —P(O)(OH)$_2$, —P(O)(O($C_{1-6}$)alkyl)$_2$ or glycosyl (the radical resulting from the removal of a hydroxyl group of the hemiacetal form of a carbohydrate).

If a disclosed compound incorporates an amine functional group, a prodrug can be formed by the replacement of a hydrogen atom in the amine group with a group such as R-carbonyl, RO-carbonyl, NRR'-carbonyl where R and R' are each independently selected from ($C_{1-10}$)alkyl, ($C_{3-7}$)cycloalkyl, benzyl, a natural $\alpha$-aminoacyl or natural $\alpha$-aminoacyl-natural-$\alpha$-aminoacyl, —C(OH)C(O)OY$^1$ wherein Y$^1$ is H, ($C_{1-6}$)alkyl or benzyl; —C(OY$^2$)Y$^3$ wherein Y$^2$ is ($C_{1-4}$)alkyl and Y$^3$ is ($C_{1-6}$)alkyl, carboxy($C_{1-6}$)alkyl, amino($C_{1-4}$)alkyl or mono-N- or di-N,N-($C_{1-6}$)alkylaminoalkyl; and —C(Y$^4$)Y$^5$ wherein Y$^4$ is H or methyl and Y$^5$ is mono-N- or di-N-($C_{1-6}$)alkylamino, morpholino, piperidin-1-yl or pyrrolidin-1-yl.

In some embodiments, the disclosed compounds may encompass an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ⁻⁻⁻⁻ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "($\pm$)" is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

In some embodiments, an enantiomer is provided partly or substantially free of the corresponding enantiomer, and may be referred to as "optically enriched," "enantiomerically enriched," "enantiomerically pure," and "non-racemic," as used interchangeably herein. The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. In some embodiments, compositions described herein contain an enantiomeric excess of at least about 50%, at least about 60%, at least about 70%, at least about 80%, at least about 90%, at least about 95%, at least about 98%, at least about 99%, or at least about 99.5% of the S enantiomer, or a range between and including any two of the foregoing values (e.g., 50-99.5% ee). In other words, the compositions contain an enantiomeric excess of the S enantiomer over the R enantiomer. In other embodiments, some compositions described herein contain an enantiomeric excess of at least about 50%, at least about 60%, at least about 70%, at least about 80%, at least about 90%, at least about 95%, at least about 98%, at least about 99%, or at least about 99.5% of the R enantiomer or a range between any two of the foregoing values (e.g., 50-99.5% ee). In other words, the compositions contain an enantiomeric excess of the R enantiomer over the S enantiomer. Where the enrichment of one enantiomer is much greater than about 80% by weight, the compositions are referred to as "substantially enantiomerically enriched," "substantially enantiomerically pure" or a "substantially non-racemic" preparation.

Thus, a composition containing 90% of one enantiomer and 10% of the other enantiomer is said to have an enantiomeric excess of 80%. In some embodiments, compositions described herein contain an enantiomeric excess of at least about 50%, at least about 60%, at least about 70%, at least about 80%, at least about 90%, at least about 95%, at least about 98%, at least about 99%, or at least about 99.5% of the S enantiomer, or a range between and including any two of the foregoing values (e.g., 50-99.5% ee). In other words, the compositions contain an enantiomeric excess of the S enantiomer over the R enantiomer. In other embodiments, some compositions described herein contain an enantiomeric excess of at least about 50%, at least about 60%, at least about 70%, at least about 80%, at least about 90%, at least about 95%, at least about 98%, at least about 99%, or at least about 99.5% of the R enantiomer or a range between any two of the foregoing values (e.g., 50-99.5% ee). In other words, the compositions contain an enantiomeric excess of the R enantiomer over the S enantiomer. Where the enrichment of one enantiomer is much greater than about 80% by weight, the compositions are referred to as "substantially enantiomerically enriched," "substantially enantiomerically pure" or a "substantially non-racemic" preparation.

Optical isomers can be obtained by resolution of the racemic mixtures according to conventional processes, e.g., by formation of diastereoisomeric salts, by treatment with an optically active acid or base. Examples of appropriate acids include, but are not limited to, tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In any embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The disclosure also embraces pharmaceutically acceptable forms that are "isotopically labeled derivatives" which are compounds that are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}$H, $^{3}$H, $^{13}$C $^{14}$C, $^{15}$N, $^{18}$O, $^{17}$O, $^{31}$P, $^{32}$P, $^{35}$S, $^{18}$F, and $^{36}$Cl, respectively. Certain isotopically-labeled disclosed compounds (e.g., those labeled with $^{3}$H and $^{14}$C) are useful in compound and/or substrate tissue distribution assays. Tritiated (i.e., $^{3}$H) and carbon-14 (i.e., $^{14}$C) isotopes can allow for ease of preparation and detectability. Further, substitution with heavier isotopes such as deuterium (i.e., $^{2}$H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure. In some embodiments, radiolabeled compounds are useful for studying metabolism and/or tissue distribution of the compounds or to alter the rate or path of metabolism or other aspects of biological functioning.

"Pharmaceutically acceptable carrier" or "pharmaceutically acceptable excipient" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sansalito, 1999; Smith and March *March's Advanced Organic Chemistry*, 5th ed., John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd ed., Cambridge University Press, Cambridge, 1987.

Recitation of ranges of values herein merely serve as a shorthand method of referring individually to each separate value and sub-range falling within the range, unless otherwise indicated herein, and each separate value and sub-range is incorporated into the specification as if it were individually recited herein. For example, "$C_{1-6}$alkyl" will be understood to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$alkyl. Likewise, 1-4 substituents will be understood to encompass 1, 2, 3, 4, 1-2, 1-3, 1-4, 2-3, 2-4 or 3-4 substituents.

"Alkyl" refers to a straight or branched hydrocarbon chain radical consisting solely of carbon and hydrogen atoms, containing no unsaturation, having from one to ten carbon atoms (e.g., $C_{1-10}$alkyl). Whenever it appears herein, a numerical range such as "1 to 10" refers to each integer in the given range; e.g., "1 to 10 carbon atoms" means that the alkyl group can consist of 1, 2, 3, 4, 5, 6, 7, 8, 9, or 10 carbon atoms, although the present definition also covers the occurrence of the term "alkyl" where no numerical range is designated. In some embodiments, alkyl groups have 1 to 10, 1 to 8, 1 to 6, or 1 to 3 carbon atoms. Representative saturated straight chain alkyls include, but are not limited to, methyl, ethyl, n-propyl, n-butyl, n-pentyl, and n-hexyl groups; while saturated branched alkyls include, but are not limited to, isopropyl, sec-butyl, isobutyl, tert-butyl, isopentyl, 2-methylbutyl, 3-methylbutyl, 2-methylpentyl, 3-methylpentyl, 4-methylpentyl, 2methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group may be optionally substituted by one or more of substituents disclosed herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, cyclopropylmethyl, cyclobutoxymethyl, benzyl, and phenethyl.

"Alkenyl" refers to a straight or branched hydrocarbon chain radical group consisting solely of carbon and hydrogen atoms, containing at least one double bond, and having from two to ten carbon atoms (i.e., $C_{2-10}$alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In any embodiments, an alkenyl comprises two to eight carbon atoms. In other embodiments, an alkenyl comprises two to six carbon atoms (e.g., $C_{2-6}$alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$alkenyl groups include the aforementioned $C_{2-4}$alkenyl groups as well as pentenyl ($C_5$), pentadienyl ($C_5$), hexenyl ($C_6$), 2,3-dimethyl-2-butenyl ($C_6$) and the like. Additional examples of alkenyl include heptenyl ($C_7$), octenyl ($C_8$), octatrienyl ($C_8$) and the like. Unless stated otherwise in the specification, an alkenyl group may be optionally substituted by one or more of substituents disclosed herein.

"Alkynyl" refers to a straight or branched hydrocarbon chain radical group consisting solely of carbon and hydrogen atoms, containing at least one triple bond, having from two to ten carbon atoms (i.e., $C_{2-10}$alkynyl). Whenever it appears herein, a numerical range such as "2 to 10" refers to each integer in the given range; e.g., "2 to 10 carbon atoms"

means that the alkynyl group can consist of 2 carbon atoms, 3 carbon atoms, etc., up to and including 10 carbon atoms. In any embodiments, an alkynyl comprises two to eight carbon atoms. In other embodiments, an alkynyl has two to six carbon atoms (e.g., $C_{2-6}$alkynyl). The alkynyl is attached to the parent molecular structure by a single bond, for example, ethynyl, propynyl, butynyl, pentynyl, 3-methyl-4-pentynyl, hexynyl, and the like. Unless stated otherwise in the specification, an alkynyl group may be optionally substituted by one or more of substituents disclosed herein.

"Alkoxy" refers to the group —O-alkyl, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, tbutoxy, pentoxy, cyclopropyloxy, cyclohexyloxy and the like. "Lower alkoxy" refers to alkoxy groups containing one to six carbons. In some embodiments, $C_{1-4}$alkoxy is an alkoxy group which encompasses both straight and branched chain alkyls of from 1 to 4 carbon atoms. Unless stated otherwise in the specification, an alkoxy group may be optionally substituted by one or more of substituents disclosed herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

"Aromatic" or "aryl" refers to a radical with 6 to 14 ring atoms (e.g., $C_{6-14}$ aromatic or $C_6$14 aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "idene" to the name of the corresponding univalent radical, e.g., a naphthyl group with two points of attachment is termed naphthylidene. Whenever it appears herein, a numerical range such as "6 to 14 aryl "refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl group may be optionally substituted by one or more of substituents disclosed herein.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic cycloalkyl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo [2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group may be optionally substituted by one or more of substituents disclosed herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof, preferably substituted with one, two, or three halo groups. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2trifluoroethyl, 1-fluoromethyl-2-fluoroethyl, —O—$CHF_2$, and the like. Each of the alkyl, alkenyl, alkynyl and alkoxy groups are as defined herein and can be optionally further substituted as defined herein.

"Heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having one or more ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having one or more ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having one or more ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having one or more ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms independently selected from nitrogen, oxygen, phosphorous, and sulfur. In some embodiments, the 5-6 membered heteroaryl has 1-2 ring heteroatoms independently selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimdinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl group may be optionally substituted by one or more of substituents disclosed herein.

"Heterocyclyl", "heterocycloalkyl" or "heterocarbocyclyl" each refer to any 3 to 18-membered non-aromatic radical monocyclic or polycyclic moiety comprising at least one carbon atom and at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-ene" to the name of the corresponding univalent radical, e.g., a piperidine group with two points of attachment is a piperidylene.

An N-containing heterocyclyl moiety refers to a non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having one or more ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having one or more ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having one or more ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having one or more ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms independently selected from nitrogen, oxygen phosphorous and sulfur. In some embodiments, the 5-6 membered heterocyclyl has 1-2 ring heteroatoms independently selected from nitrogen, oxygen, phosphorous and sulfur. In some embodiments, the 5-6 membered heterocyclyl has 1 ring heteroatom selected from nitrogen, oxygen, phosphorous and sulfur.

"Heterocyclyl" may include one or more ketone group (—C(=O)—) as part of the ring. Examples of a ketone-containing heterocycle include, without limitation, pyridin-2(1H)-one, pyrazin-2(1H)-one, pyrimidin-2(1H)-one, pyrimidin-4(3H)-one, pyridazin-3(2H)-one, pyridin-4(1H)-one, imidazolidin-2-one, 1,3-dihydro-2H-imidazol-2-one, 2,4-dihydro-3H-1,2,4-triazol-3-one, oxazol-2(3H)-one, and oxazolidin-2-one. A ketone-containing heterocyclyl is obtainable by removing a hydrogen atom from its corresponding ketone-containing heterocycle at any available N—H or C—H position.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2, 5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise in the specification, a heterocyclyl group may be optionally substituted by one or more of substituents disclosed herein.

Where substituent groups are specified by their conventional chemical formulae, written from left to right, they equally encompass the chemically identical substituents that would result from writing the structure from right to left, e.g., —CH$_2$O— is equivalent to —OCH$_2$—.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy, trifluoromethyloxy, and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. Non-limiting embodiments of functional groups that can be masked with a protecting group include an amine, hydroxy, thiol, carboxylic acid, and aldehyde. For example, a hydroxy protected form is where at least one of the hydroxy groups present in a compound is protected with a hydroxy protecting group. A variety of protecting groups are disclosed, for example, Greene's Protective Groups in Organic Synthesis, Fifth Edition, Wiley (2014), incorporated herein by reference in its entirety. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); Greene's Protective Groups in Organic Synthesis, Fifth Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). These references are incorporated herein by reference in their entirety.

The terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties (other than hydrogen) can be optionally substituted with one or more substituents (up to six, valence permitting) independently selected from OH, NH$_2$, oxo, halo, nitro, COOH, C(O)NH$_2$ or cyano. For example, a cycloalkyl substituent can have a halide substituted at one or more ring carbons, and the like. The protecting groups that can form the protective derivatives of the above substituents are known to those of skill in the art and can be found in references such as Greene and Wuts, above.

Suitable substituents include, but are not limited to, haloalkyl and trihaloalkyl, alkoxyalkyl, halophenyl, -M-heteroaryl, -M-heterocycle, -M-aryl, -M-OR$^a$, -M-SR$^a$, -M-N(R$^a$)$_2$, -M-OC(O)N(R$^a$)$_2$, -M-C(=NR$^a$)N(R$^a$)$_2$, -M-C(=NR$^a$)OR$^a$, -M-P(O)(R$^a$)$_2$, Si(R$^a$)$_3$, -M-NR$^a$C(O)R$^a$, -M-NR$^a$C(O)OR$^a$, -M-C(O)R$^a$, -M-C(=S)R$^a$, -M-C(=S)NR$^a$R$^a$, -M-C(O)N(R$^a$)$_2$, -M-C(O)NR$^a$-M-N(R$^a$)$_2$, -M-NR$^a$C(NR$^a$)N(R$^a$)$_2$, -M-NR$^a$C(S)N(R$^a$)$_2$, -M-S(O)$_2$R$^a$, -M C(O)R$^a$, -M-OC(O)R$^a$, -MC(O)SR$^a$, -M-S(O)$_2$N(R$^a$)$_2$, —C(O)-M-C(O)R$^a$, -MCO$_2$R$^a$, -MC(=O)N(R$^a$)$_2$, -M-C(=NH)N(R$^a$)$_2$, and -M-OC(=NH)N(R$^a$)$_2$ (wherein M is a C$_{1-6}$alkyl group).

When a ring system (e.g., cycloalkyl, heterocyclyl, aryl, or heteroaryl) is substituted with several substituents varying within an expressly defined range, it is understood that the total number of substituents does not exceed the normal available valencies under the existing conditions. Thus, for example, a phenyl ring substituted with "p" substituents (where "p" ranges from 0 to 5) can have 0 to 5 substituents, whereas it is understood that a pyridinyl ring substituted with "p" substituents has several substituents ranging from 0 to 4. The maximum number of substituents that a group in the disclosed compounds can have can be easily determined. The substituted group encompasses only those combinations of substituents and variables that result in a stable or chemically feasible compound. A stable compound or chemically feasible compound is one that, among other factors, has stability sufficient to permit its preparation and detection. In some embodiments, disclosed compounds are sufficiently stable that they are not substantially altered when kept at a temperature of 40° C. or less, in the absence of moisture (e.g., less than about 10%, less than about 5%, less than about 2%, less than about 1%, or less than about 0.5%) or other chemically reactive conditions, for e.g., at least about 3 days, at least about a week, at least about 2 weeks, at least about 4 weeks, or at least about 6 weeks.

The terms "combine, combining, to combine, combination" refer to the action of adding at least one chemical substance to another chemical substance(s) either sequentially or simultaneously. In some embodiments, bringing these chemical substances together can result in transformation of the initial chemical substances into one or more different chemical substances. This transformation can occur through one or more chemical reactions, e.g., where covalent bonds are formed, broken, rearranged and the like. A non-limiting example can include hydrolysis of an ester into an alcohol and carboxylic acid which can result from the combination of the ester with a suitable base. In another non-limiting example, an aryl fluoride can be combined with an amine to provide an aryl amine through a substitution process. These terms also include changes in association of charged chemical substances and creation of charged chemical substances, such as, but not limited to, N-oxide formation, acid addition salt formation, basic addition salt formation, and the like. These terms include the creation and/or transformation of radical chemical substances and isotopically labeled chemical substances.

The terms "convert, converting, to convert, conversion" refer to a subset of "combination" and its grammatical equivalents, where the action of one or more reagents transforms one or more functional groups on a chemical substance to another functional group(s). For example, a conversion includes, but is not limited to, transforming a nitro functional group on a chemical substance to an amine with a reducing agent. Conversions also include changes in charged chemical substances, radical chemical substances and isotopically labeled chemical substances. However, the term "convert" does not include alteration of conserved bonds in disclosed genuses and compounds.

Compounds

In one aspect, the present technology relates to a compound of Formula (I):

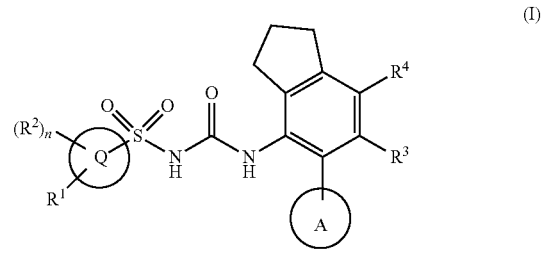

or a pharmaceutically acceptable salt, tautomer or stereoisomer thereof,
wherein:
Ring A is a fused 6,5-bicyclic aryl or heteroaryl ring system, wherein the heteroaryl ring system comprises 1, 2, 3, or 4 nitrogen atoms as ring members, and the Ring A bears an R$^5$ and an R$^6$ substituent and bears 1, 2 or 3 substituents on ring carbons selected from R$^7$ or R$^9$, and/or bears 1 or 2 substituents on ring nitrogens selected from R$^8$ and R$^{10}$.
Ring Q is a fused 6,5-bicyclic heteroaryl or a fused 6,6-bicyclic heteroaryl ring system comprising 1, 2 or 3 nitrogen atoms as ring members and optionally comprising 1 or 2 ring members selected from O, S or S(=O$_2$), wherein the Ring Q bears R$^1$ and R$^2$ substituents as indicated in Formula (I), and optionally bears 1 or 2 R$^{12}$ substituents;
each occurrence of R$^1$ is independently hydrogen, C$_{1-4}$alkyl, haloC$_{1-4}$alkyl, C$_{3-7}$cycloalkyl, C$_{1-4}$alkoxy, C$_{3-7}$cycloalkoxy, oxo (=O), NR$^a$R$^b$, C(=O)OR$^a$, OC(=O)R$^a$, C(=O)NR$^a$R$^b$, NR$^b$C(=O)R$^a$, C(=O)NHC(=O)R$^a$, or 4-6-membered heterocyclyl, each of which is optionally substituted with one to three R$^{11}$;
each occurrence of R$^2$ is independently C$_{1-4}$alkyl, haloC$_{1-4}$alkyl, C$_{3-7}$cycloalkyl, halogen, CN, OH, C$_{1-4}$alkoxy, NR$^a$R$^b$, C(=O)NR$^a$R$^b$, or 4-6-membered heterocyclyl, each of which is optionally substituted with one to two R$^{11}$, or two R$^2$ groups at geminal position may optionally form a spiro C$_{3-5}$cycloalkyl;
R$^3$, R$^4$, R$^5$, and R$^6$ are each independently hydrogen, halogen, CN, C$_{1-4}$alkyl, or haloC$_{1-4}$alkyl;

each occurrence of $R^7$ is independently hydrogen or $C_{1-4}$alkyl;

each occurrence of $R^8$ is independently hydrogen or $C_{1-4}$alkyl;

each occurrence of $R^9$ is independently hydrogen, $C_{1-4}$alkyl or $C_{1-4}$alkoxy;

each occurrence of $R^{10}$ is independently hydrogen, $C_{1-4}$alkyl, $C_{3-7}$cycloalkyl, or 4-6-membered heterocyclyl optionally substituted with $C_{1-4}$alkyl;

each occurrence of $R^{11}$ is independently, $C_{1-4}$alkyl, halo$C_{1-4}$alkyl, halogen, CN, OH, $C_{3-7}$ cycloalkyl, $C_{1-4}$alkoxy, $C_{3-7}$ cycloalkoxy, $NR^aR^b$, $C(=O)OR^a$, $OC(=O)R^a$, $C(=O)NR^aR^b$, $NR^bC(=O)R^a$, $C(=O)NHC(=O)R^a$, or 4-6-membered heterocyclyl;

each occurrence of $R^{12}$ is independently hydrogen, $C_{1-4}$alkyl, halo$C_{1-4}$alkyl, $C_{3-7}$cycloalkyl, $C_{1-4}$alkyl-$C_{3-7}$cycloalkyl, $C_{1-4}$alkyl-$NR^aR^b$, $C(=O)R^a$, $C(=O)NR^aR^b$, or 4-6-membered heterocyclyl optionally substituted with one to three groups selected from $C_{1-4}$alkyl, halo$C_{1-4}$alkyl, $C_{3-7}$cycloalkyl, halogen, CN, OH, $C_{1-4}$alkoxy, $C_{3-7}$cycloalkoxy, or $NR^aR^b$;

each occurrence of $R^a$ and $R^b$ is independently hydrogen, $C_{1-4}$alkyl, $C_{3-5}$cycloalkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl; and each occurrence of n is independently 0, 1, or 2.

In some embodiments, the present technology relates to a compound of Formula (I) having the structure of any of Formulae (II)-(IV):

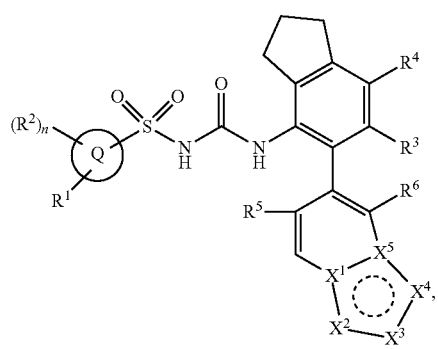

(II)

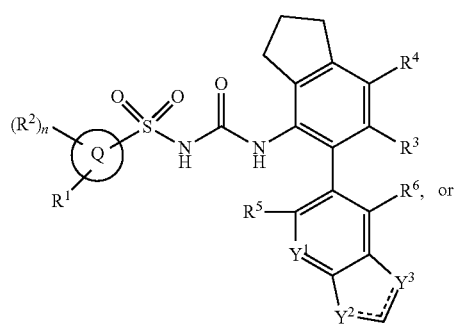

(III)

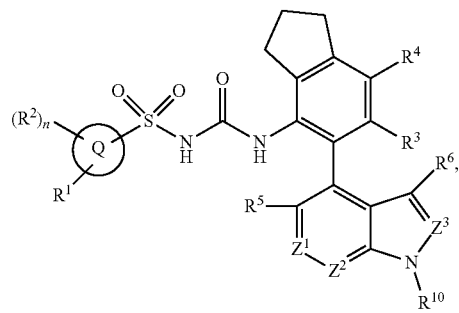

(IV)

or a pharmaceutically acceptable salt, tautomer or stereoisomer thereof,
wherein:
each occurrence of Ring Q is independently

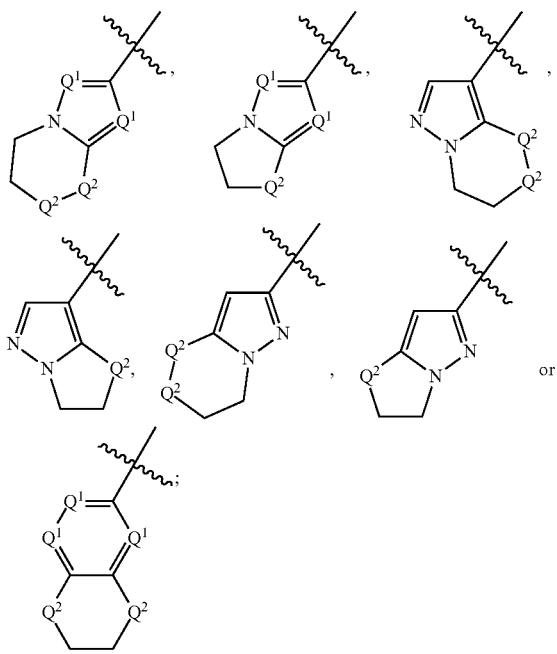

each occurrence of $Q^1$ is independently N or CH, provided that at least one $Q^1$ is N;
each occurrence of $Q^2$ is independently O, S, S($=O_2$), $CH_2$, or $NR^{12}$, provided that at least one $Q^2$ is CH when two $Q^2$ are adjacent in a ring;
$X^1$ and $X^5$ are each independently N or C, $X^2$, $X^3$, and $X^4$ are each independently N or $CR^7$, and the dashed circle denotes bonds forming a five-membered aromatic ring; provided that at least two but no more than three of $X^1$, $X^2$, $X^3$, $X^4$ and $X^5$ are N;
$Y^1$ is N or CH, $Y^2$ is N, $NR^8$ or CH, and $Y^3$ is N, $NR^8$ or CH, and

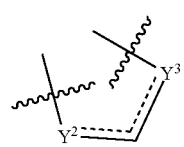

in Formula (III) denotes

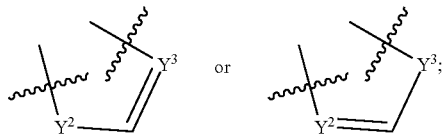

$Z^1$ is N or CH, $Z^2$ is N or $CR^9$, and $Z^3$ is N or CH;

each occurrence of $R^1$ is independently hydrogen, $C_{1-4}$alkyl, halo$C_{1-4}$alkyl, $C_{3-7}$cycloalkyl, $C_{1-4}$alkoxy, $C_{3-7}$cycloalkoxy, oxo (=O), $NR^aR^b$, C(=O)$OR^a$, OC(=O)$R^a$, C(=O)$NR^aR^b$, $NR^bC$(=O)$R^a$, C(=O)NHC(=O)$R^a$, or 4-6-membered heterocyclyl, each of which is optionally substituted with one to three $R^{11}$;

each occurrence of $R^2$ is independently hydrogen, $C_{1-4}$alkyl, halo$C_{1-4}$alkyl, $C_{3-7}$cycloalkyl, halogen, CN, OH, $C_{1-4}$alkoxy, $NR^aR^b$, C(=O)$NR^aR^b$, or 4-6-membered heterocyclyl, each of which is optionally substituted with one to two $R^{11}$, or two $R^2$ groups at geminal position may optionally form a spiro $C_{3-5}$cycloalkyl;

$R^3$, $R^4$, $R^5$ and $R^6$ are each independently hydrogen, halogen, CN, $C_{1-4}$alkyl, or halo$C_{1-4}$alkyl;

each occurrence of $R^7$ is independently hydrogen or $C_{1-4}$alkyl;

each occurrence of $R^8$ is independently hydrogen or $C_{1-4}$alkyl;

each occurrence of $R^9$ is independently hydrogen, $C_{1-4}$alkyl or $C_{1-4}$alkoxy;

each occurrence of $R^{10}$ is independently hydrogen, $C_{1-4}$alkyl, $C_{3-7}$cycloalkyl, or 4-6-membered heterocyclyl optionally substituted with $C_{1-4}$alkyl;

each occurrence of $R^{11}$ is independently hydrogen, $C_{1-4}$alkyl, halo$C_{1-4}$alkyl, halogen, CN, OH, $C_{3-7}$cycloalkyl, $C_{1-4}$alkoxy, $C_{3-7}$cycloalkoxy, $NR^aR^b$, C(=O)$OR^a$, OC(=O)$R^a$, C(=O)$NR^aR^b$, $NR^bC$(=O)$R^a$, C(=O)NHC(=O)$R^a$, or 4-6-membered heterocyclyl;

each occurrence of $R^{12}$ is independently hydrogen, $C_{1-4}$alkyl, halo$C_{1-4}$alkyl, $C_{3-7}$cycloalkyl, $C_{1-4}$alkyl-$C_{3-7}$cycloalkyl, $C_{1-4}$alkyl-$NR^aR^b$, C(=O)$R^a$, C(=O)$NR^aR^b$, or 4-6-membered heterocyclyl optionally substituted with one to three groups selected from $C_{1-4}$alkyl, halo$C_{1-4}$alkyl, $C_{3-7}$cycloalkyl, halogen, CN, OH, $C_{1-4}$alkoxy, $C_{3-7}$cycloalkoxy, or $NR^aR^b$;

each occurrence of $R^a$ and $R^b$ is independently hydrogen, $C_{1-4}$alkyl, $C_{3-5}$cycloalkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl; and each occurrence of n is independently 0, 1, or 2.

In some embodiments, the present technology relates to a compound of Formula (II):

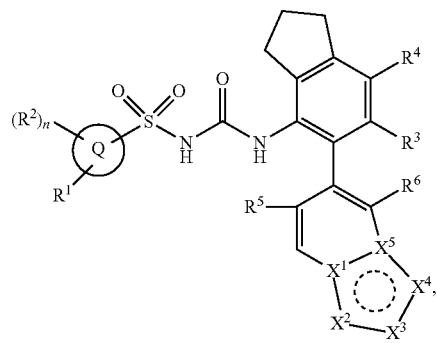

or a pharmaceutically acceptable salt, tautomer or stereoisomer thereof, wherein Q, $Q^1$, $Q^2$, $X^1$, $X^2$, $X^3$, $X^4$, $X^5$, $R^1$, $R^2$, $R^3$, $R^4$, $R^5$, $R^6$, $R^7$, $R^{11}$, $R^{12}$, $R^a$, $R^b$, and n are each as defined above, or may have any of the values disclosed herein.

In any embodiments of the compounds of Formula (II),

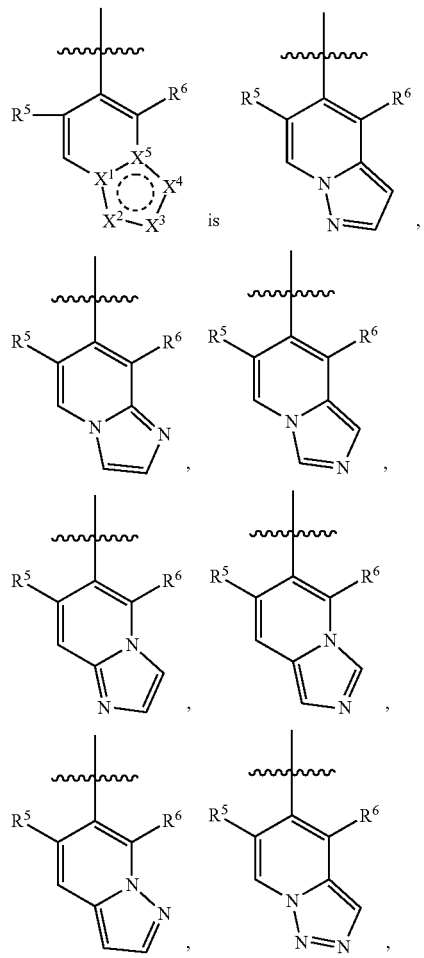

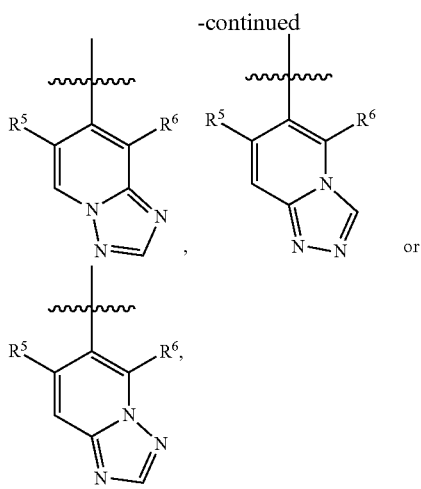

wherein $R^5$ and $R^6$ are each as defined above, or may have any of the values disclosed herein.

In some embodiments, the present technology relates to a compound of Formula (III):

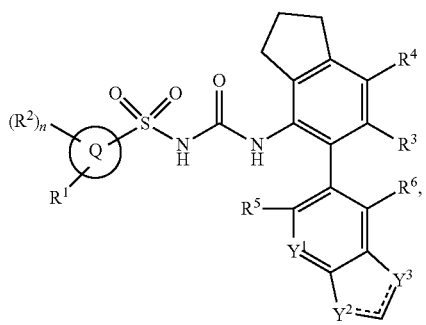

(III)

or a pharmaceutically acceptable salt, tautomer or stereoisomer thereof, wherein Q, $Q^1$, $Q^2$, $Y^1$, $Y^2$, $Y^3$, $R^1$, $R^2$, $R^3$, $R^4$, $R^5$, $R^6$, $R^8$, $R^{11}$, $R^{12}$, $R^a$, $R^b$, and n are each as defined above, or may have any of the values disclosed herein.

In any embodiments of the compounds of Formula (III),

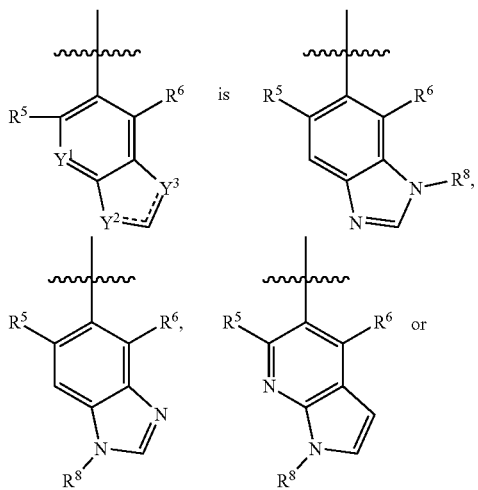

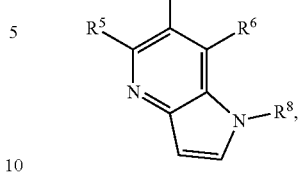

wherein $R^5$, $R^6$ and $R^8$ are each as defined above, or may have any of the values disclosed herein.

In some embodiments, the present technology relates to a compound of Formula (IV):

(IV)

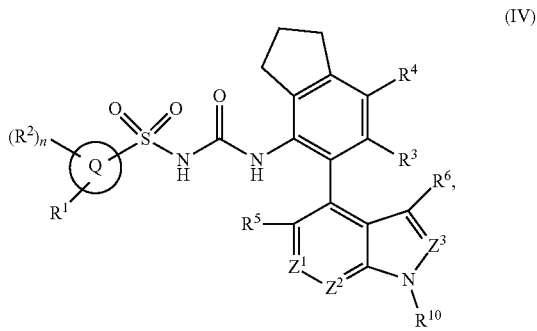

or a pharmaceutically acceptable salt, tautomer or stereoisomer thereof, wherein Q, $Q^1$, $Q^2$, $Z^1$, $Z^2$, $Z^3$, $R^1$, $R^2$, $R^3$, $R^4$, $R^5$, $R^6$, $R^9$, $R^{10}$, $R^{11}$, $R^{12}$, $R^a$, $R^b$, and n are each as defined above, or may have any of the values disclosed herein.

In any embodiments of the compounds of Formula (IV),

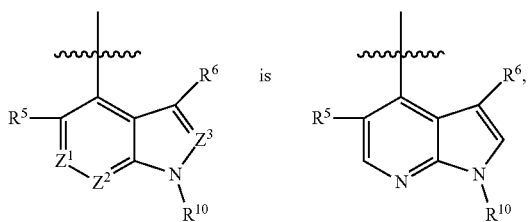

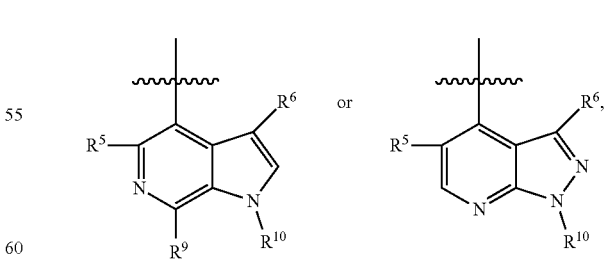

wherein $R^5$, $R^6$, $R^9$, and $R^8$ are each as defined above, or may have any of the values disclosed herein.

In any embodiments of the present compounds (including but not limited to compounds of Formulae I, II, III, and IV), Q at each occurrence is independently

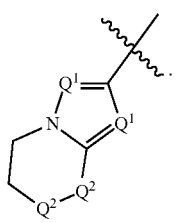

In some embodiments, Q at each occurrence is independently

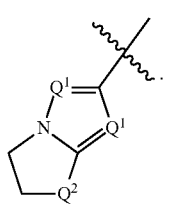

In some embodiments, Q at each occurrence is independently

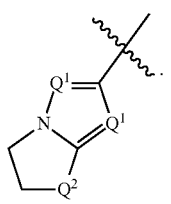

In some embodiments, Q at each occurrence is independently

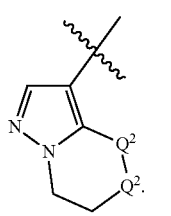

In some embodiments, Q at each occurrence is independently In some embodiments, Q at each occurrence is independently

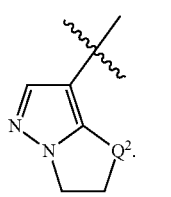

In some embodiments, Q at each occurrence is independently

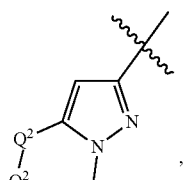

In some embodiments, Q at each occurrence is independently

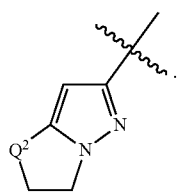

In some embodiments, Q at each occurrence is independently

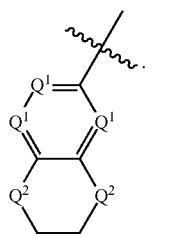

In some embodiments, Q at each occurrence together with $R^1$ and $R^2$ is independently

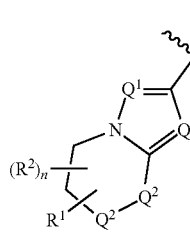

In some embodiments, Q at each occurrence together with $R^1$ and $R^2$ is independently

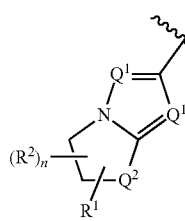

In some embodiments, Q at each occurrence together with $R^1$ and $R^2$ is independently

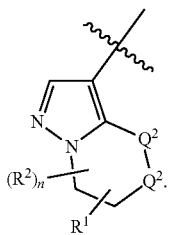

In some embodiments, Q at each occurrence together with $R^1$ and $R^2$ is independently

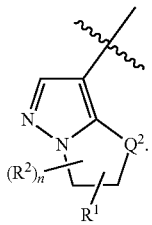

In some embodiments, Q at each occurrence together with $R^1$ and $R^2$ is independently

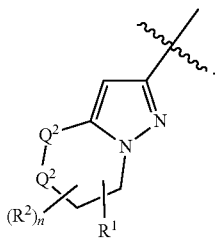

In some embodiments, Q at each occurrence together with $R^1$ and $R^2$ is independently

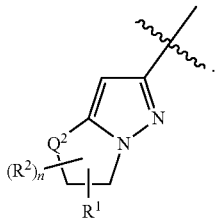

In some embodiments, Q at each occurrence together with $R^1$ and $R^2$ is independently

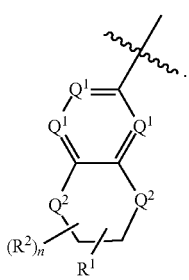

In any embodiments of the present compounds, each occurrence of $Q^1$ is independently N or CH, provided that only one $Q^1$ is N per ring. In some embodiments, each occurrence of $Q^2$ is independently O, $CH_2$ or $NR^{12}$, provided that at least one $Q^2$ is CH when there are two adjacent $Q^2$ groups in a ring.

In any embodiments of the present compounds, $R^1$ at each occurrence is independently $C_{1-4}$alkyl, halo$C_{1-4}$alkyl, cyclopropyl, cyclobutyl, $C_{1-4}$alkoxy, cyclopropyloxy, cyclobutyloxy, $NR^aR^b$, or 4-6-membered heterocyclyl, each of which is optionally substituted with one to three $R^{11}$. In some embodiments, $R^1$ at each occurrence is independently $C_{1-4}$alkyl, $C_{3-5}$cycloalkyl, $C_{1-4}$alkoxy, $C_{3-5}$cycloalkoxy, $NR^aR^b$, or 4-6-membered heterocyclyl, each of which is optionally substituted with one to three $R^{11}$. In some embodiments, the $C_{3-5}$cycloalkyl is cyclopropyl or cyclobutyl, and the $C_{3-5}$cycloalkoxy is cyclopropyloxy or cyclobutyloxy. In some embodiments, $R^1$ at each occurrence is independently $C_{1-4}$alkyl. In some embodiments, $R^1$ at each occurrence is independently $C_{1-4}$alkyl, which is optionally substituted with one to three $R^{11}$. In some embodiments, $R^1$ at each occurrence is independently methyl. In some embodiments, $R^1$ at each occurrence is independently methyl, which is optionally substituted with one $R^{11}$. In some embodiments, $R^1$ at each occurrence is independently methoxy. In some embodiments, $R^1$ at each occurrence is independently cyclopropyl. In some embodiments, $R^1$ at each occurrence is independently cyclopropyl, which is optionally substituted with one $R^{11}$. In some embodiments, $R^1$ at each occurrence is independently cyclobutyl. In some embodiments, $R^1$ at each occurrence is independently cyclobutyl, which is optionally substituted with one $R^{11}$. In some embodiments, $R^1$ at each occurrence is independently oxetane. In some embodiments, $R^1$ at each occurrence is independently oxetane, which is optionally substituted with one $R^{11}$. In some embodiments, $R^1$ at each occurrence is independently

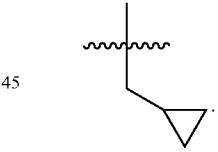

In some embodiments, $R^1$ at each occurrence is independently

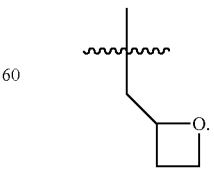

In some embodiments, $R^1$ at each occurrence is independently

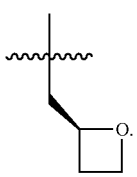 [SMILES: *C[C@@H]1CCO1]

In any embodiments of the present compounds, $R^2$ at each occurrence is independently hydrogen, $C_{1-4}$alkyl, halo$C_{1-4}$alkyl, $C_{3-5}$cycloalkyl, halogen, CN, OH, $C_{1-4}$alkoxy, $NR^aR^b$, or 4-6-membered heterocyclyl, each of which is optionally substituted with one to two $R^{11}$. In some embodiments, two $R^2$ groups at geminal position may optionally form a spiro $C_{3-5}$cycloalkyl. In some embodiments, two $R^2$ groups at geminal position may optionally form a spiro cyclobutyl. In some embodiments, $R^3$ at each occurrence is independently hydrogen, methyl, F, or Cl. In some embodiments, $R^4$ at each occurrence is independently hydrogen, methyl or halogen. In some embodiments, $R^5$ at each occurrence is independently is hydrogen or methyl. In some embodiments, $R^6$ at each occurrence is independently hydrogen or methyl. In some embodiments, $R^7$ at each occurrence is independently hydrogen or methyl. In some embodiments, $R^8$ at each occurrence is independently hydrogen or methyl. In some embodiments, $R^9$ at each occurrence is independently hydrogen, methyl or methoxy. In some embodiments, $R^{10}$ at each occurrence is independently hydrogen, $C_{1-4}$alkyl, $C_{3-5}$cycloalkyl, or 4-6-membered heterocyclyl optionally substituted with $C_{1-4}$alkyl, in which the 4-6-membered heterocyclyl contains one to two heteroatoms selected from N, O and S. In some embodiments, $R^{11}$ at each occurrence is independently hydrogen, $C_{1-4}$alkyl, $C_{3-5}$cycloalkyl, halogen, CN, OH, $C_{1-4}$alkoxy, $C_{3-5}$cycloalkoxy, $NR^aR^b$, or 4-6-membered heterocyclyl, in which the 4-6-membered heterocyclyl contains one to two heteroatoms selected from N, O and S. In some embodiments, $R^{11}$ at each occurrence is independently cyclopropyl. In some embodiments, $R^{11}$ at each occurrence is independently cyclobutyl. In some embodiments, $R^{11}$ at each occurrence is independently oxetane. In some embodiments, $R^{12}$ at each occurrence is independently hydrogen, $C_{1-4}$alkyl, halo$C_{1-4}$alkyl, $C_{3-5}$cycloalkyl, $C_{1-4}$alkyl-$C_{3-5}$cycloalkyl, $C_{1-4}$alkyl-$NR^aR^b$, $C(=O)R^a$, $C(=O)NR^aR^b$, or 4-6-membered heterocyclyl optionally substituted with one to three groups selected from $C_{1-4}$alkyl, halo$C_{1-4}$alkyl, $C_{3-5}$cycloalkyl, halogen, CN, OH, $C_{1-4}$alkoxy, $C_{3-5}$cycloalkoxy, or $NR^aR^b$, in which the 4-6-membered heterocyclyl contains one to two heteroatoms selected from N, O and S. In some embodiments, $R^{12}$ at each occurrence is independently $C_{1-4}$alkyl. In some embodiments, $R^{12}$ at each occurrence is independently methyl. In some embodiments, $R^{12}$ at each occurrence is independently $C_{3-5}$cycloalkyl. In some embodiments, $R^{12}$ at each occurrence is independently cyclopropyl.

In any embodiments of the present compounds, n is 0. In some embodiments, n is 1. In some embodiments, n is 2.

In any embodiments, the compound is selected from:

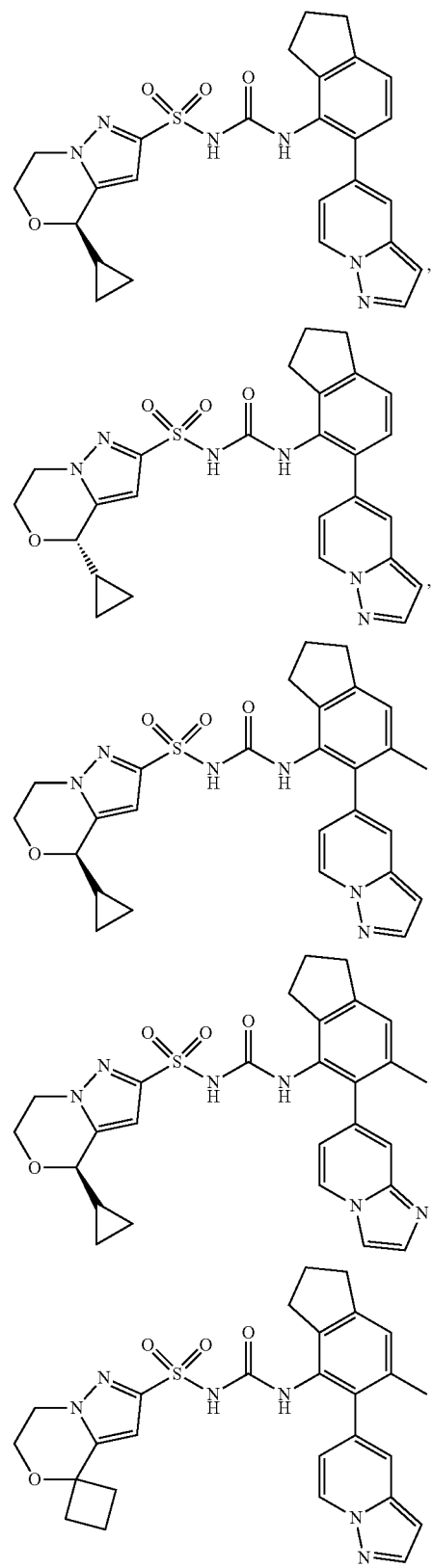

In any embodiments, the compound is selected from:

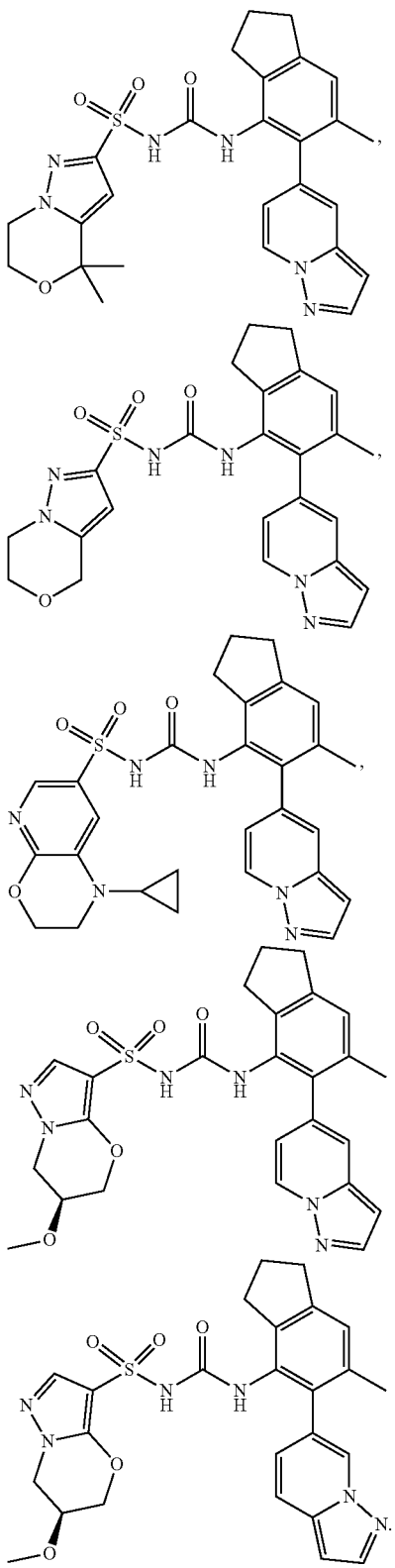

and

In some embodiments, the present technology relates to a compound of Formulae (I), (II), (III) and (IV), including each exemplified compound, wherein at least one hydrogen (H) is replaced with deuterium (D). Enriching for deuterium may afford certain therapeutic advantages, such as increasing in vivo half-life or reducing dosage requirements, or may provide a compound useful as a standard for characterization of biological samples. In some other embodiments, a compound provided herein may have an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In another aspect, the present technology relates to a pharmaceutical composition comprising a compound disclosed herein (including but not limited to a compound of Formulae Formulae (I), (II), (III) and (IV)) and a pharmaceutically acceptable carrier.

In yet another aspect, the present technology relates to a method for treating or preventing a disease or condition which is responsive to inhibition of the NLRP3 in a subject in need thereof, comprising administering an effective amount of a compound disclosed herein (including but not limited to a compound of Formulae (I), (II), (III) and (IV)) to the subject.

In yet another aspect, the present technology relates to a method for treating or preventing a disease or condition in a subject in need thereof, comprising administering an effective amount of a compound disclosed herein (including but not limited to a compound of Formulae (I), (II), (III) and (IV)) to the subject, wherein the disease or condition is a hereditary disease, a neurodegenerative disorder, a metabolic ailment, an inflammatory syndrome, or cancer. In some embodiments, the hereditary disease is Cryopyrin-associated periodic syndrome. In some embodiments, the neurodegenerative disorder is multiple sclerosis, Alzheimer's disease or Parkinson's disease. In some embodiments, the metabolic ailment is atherosclerosis or type 2 diabetes. In some embodiments, the inflammatory syndrome is gout flares or osteoarthritis.

In yet another aspect, the present technology relates to a process of making a compound of Formulae (I), (II), (III) and (IV), including each exemplified compound and intermediate described herein.

EXAMPLES

General Synthetic Methods

The compounds of the present technology can be synthesized using the methods described herein, together with synthetic methods known in the art of synthetic organic chemistry, or by variations thereon as appreciated by those skilled in the art. Preferred methods include, but are not limited to, those exemplary schemes and working examples described below. All substituents are as defined hereinabove unless otherwise indicated. The reactions are performed in a solvent or solvent mixture appropriate to the reagents and materials employed and suitable for the transformations proposed. This will sometimes require a judgment to modify the order of synthetic steps or to select on particular process scheme over another in order to obtain a desired compound of the technology.

It will be recognized that another major consideration in the planning of any synthetic route in this field is the judicious choice of the protecting group used for protection of the reactive functional groups present in the compounds described in this technology. An authoritative account describing the many alternatives to the trained practitioner is by Greene et al., Greene's Protective Groups in Organic Synthesis, Fifth Edition, Wiley (2014). It will also be recognized that the compound names referred to in the decryptions of Schemes 1-3 are for convenience only, and do not necessarily reflect the actual chemical names of those compounds.

ence of a Pd catalyst (e.g. Pd(dppf)Cl$_2$) and base (e.g. K$_2$CO$_3$) in an appropriate solvent (e.g. 1,4-dioxane/water) provides Compound 3. Treatment Compound 3 with triphosgene in the presence of a base (e.g. TEA, DIPEA) in an appropriate solvent (e.g. DCM, THF) yields an isocyanate intermediate, which is then reacted with Compound 4 in the presence of a base (e.g. NaH, t-BuONa) in an appropriate solvent (e.g. THF, CH$_3$CN) to provide the desired the compounds of Formula (II).

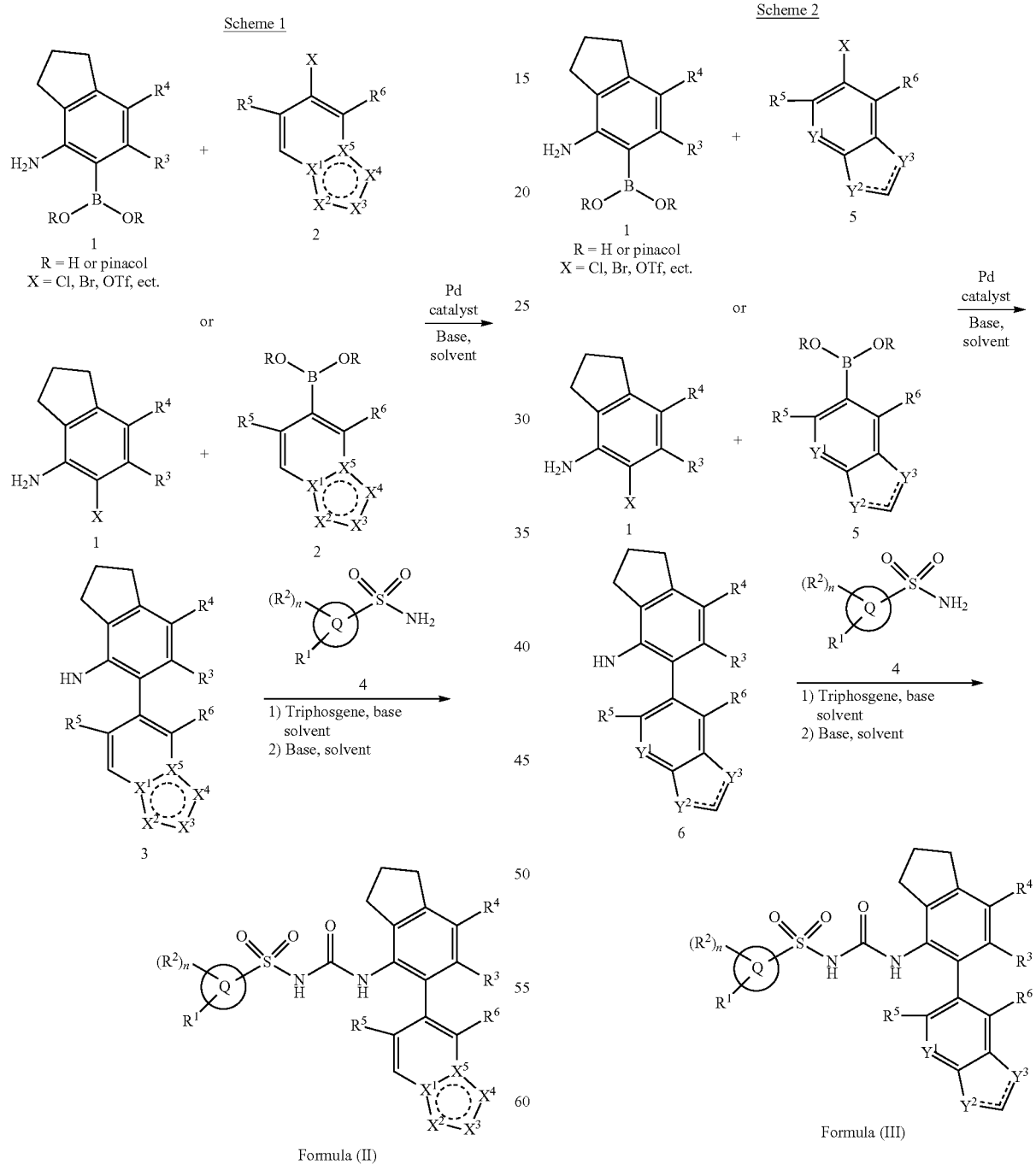

Scheme 1 describes a general synthetic route to the compounds of Formula (II). Treatment of Compound 1 and Compound 2 under Suzuki coupling conditions in the presence of a Pd catalyst (e.g. Pd(dppf)Cl$_2$) and base (e.g. K$_2$CO$_3$) in Scheme 2 describes a general synthetic route to the compounds of Formula (III). Treatment of Compound 1 and Compound 5 under Suzuki coupling conditions the presence of a Pd catalyst (e.g. Pd(dppf)Cl$_2$) and base (e.g. K$_2$CO$_3$) in an appropriate solvent (e.g. 1,4-dioxane/water) provides Compound 6. Treatment of Compound 6 with triphosgene in the presence of a base (e.g. TEA, DIPEA) in an appropriate solvent (e.g. DCM, THF) gives isocyanate intermediate, which is then reacted with Compound 4 in the presence of a base (e.g. NaH, t-BuONa) in an appropriate solvent (e.g. THF, CH$_3$CN) to provide the compounds of Formula (III).

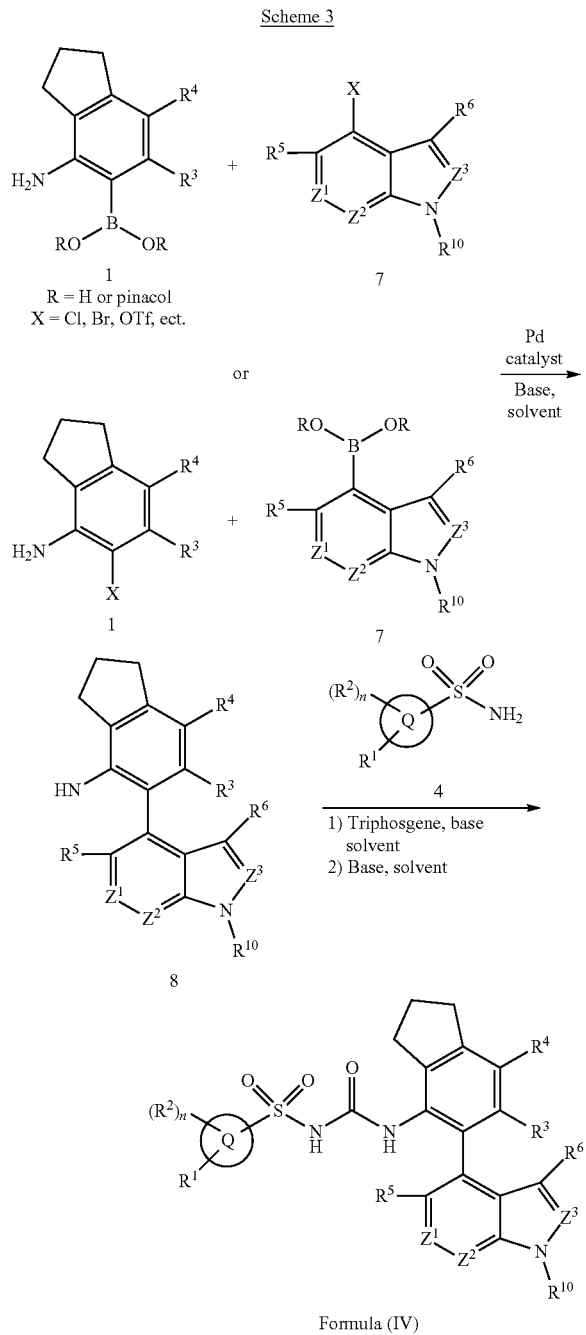

Scheme 3

Scheme 3 describes a general synthetic route to the compounds of Formula (IV). Treatment of Compound 1 and Compound 7 under Suzuki coupling conditions in the presence of a Pd catalyst (e.g. Pd(dppf)Cl$_2$) and base (e.g. K$_2$CO$_3$) in an appropriate solvent (e.g. 1,4-dioxane/water) provides compound 8. Treatment of Compound 8 with triphosgene in the presence of a base (e.g. TEA, DIPEA) in an appropriate solvent (e.g. DCM, THF) gives an isocyanate intermediate, which is then reacted with Compound 4 in the presence of a base (e.g. NaH, t-BuONa) in an appropriate solvent (e.g. THF, CH$_3$CN) to provide the compounds of Formula (IV).

Pharmaceutical Compositions and Methods

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of the present technology, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of the present technology include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of the present technology may be administered orally, parenterally, by inhalation spray, topically, rectally, nasally, buccally, vaginally or via an implanted reservoir, preferably by oral administration or administration by injection. The pharmaceutical compositions of the present technology may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of the present technology may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of the present technology may also be administered in the form of suppositories for rectal administration. These compositions can be prepared by mixing a compound of the present technology with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of the present technology is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of the present technology include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of the present technology may also be topically applied to the lower intestinal tract by rectal suppository formulation or in a suitable enema formulation. Topically-transdermal patches are also included in the present technology.

The pharmaceutical compositions of the present technology may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of the present technology comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of the present technology. Alternatively, those agents may be part of a single dosage form, mixed together with the compounds of the present technology in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the drug. The methods herein contemplate administration of an effective amount of compound or compound composition to achieve the desired or stated effect. Typically, the pharmaceutical compositions of the present technology will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of the present technology may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Abbreviations used herein are as follows:

| Abbrv. | Full Name | Abbrv. | Full Name |
| --- | --- | --- | --- |
| anhy. | anhydrous | aq. | aqueous |
| min | minute(s) | satd. | saturated |
| mL | milliliter | hrs | hours |
| mmol | millimole(s) | mol | mole(s) |
| MS | mass spectrometry | NMR | nuclear magnetic resonance |
| TLC | thin layer chromatography | HPLC | high-performance liquid chromatography |
| r.t. | Room temperature | SFC | Supercritical Fluid Chromatography |
| LCMS | Liquid chromatography-mass spectrometry | PPTS | Pyridinium p-Toluenesulfonate |
| DCE | 1,2-dichloroethane | $CHCl_3$ | chloroform |
| DCM | dichloromethane | DMF | dimethylformamide |
| $Et_2O$ | diethyl ether | EtOH | ethyl alcohol |
| EtOAc | ethyl acetate | MeOH | methyl alcohol |
| MeCN | acetonitrile | PE | petroleum ether |
| THF | tetrahydrofuran | DMSO | dimethyl sulfoxide |
| AcOH | acetic acid | HCl | hydrochloric acid |
| $H_2SO_4$ | sulfuric acid | $NH_4Cl$ | ammonium chloride |
| KOH | potassium hydroxide | NaOH | sodium hydroxide |
| $K_2CO_3$ | potassium carbonate | $Na_2CO_3$ | sodium carbonate |
| TFA | trifluoroacetic acid | $Na_2SO_4$ | sodium sulfate |
| $NaBH_4$ | sodium borohydride | $NaHCO_3$ | sodium bicarbonate |
| LiHMDS | lithium hexamethyldisilylamide | $NaBH_4$ | sodium borohydride |
| NMP | N-methyl pyrrolidone | t-BuONO | tert-Butyl nitrite |
| $Et_3N$ or TEA | Triethylamine | Py or Pyr | pyridine |
| TBAF | Tetrabutylammonium fluoride | MsCl | Methanesulfonyl chloride |
| BnBr | Benzyl bromide | DHP | 3,4-Dihydro-2H-pyran |
| Cbz | carbobenzyloxy | m-CPBA | 3-Chloroperoxybenzoic acid |
| Dess-Martin | 1,1,1-Triacetoxy-1,1-Dihydro-1,2-Benziodoxol-3(1H)-On | DIAD | Diisopropyl azodicarboxylate |
| DMAP | 4-(dimethylamino)pyridine | DIPEA | N,N-diisopropylethylamine |
| $ClSO_3H$ | Chlorosulfonic acid | $PCl_5$ | Phosphorus pentachloride |
| MeMgBr | Methylmagnesium bromide | KSAc | Potassium thioacetate |
| NCS | N-Chlorosuccinimide | PTSA | p-Toluenesulfonic acid |
| TosCl | p-Toluenesulfonyl chloride | MTBE | tert-Butyl methyl ether |
| DIBAL-H | Diisobutylaluminum Hydride | | |
| $Pd_2(dba)_3$ | Tris(dibenzylideneacetone)dipalladium | | |
| $Pd(OAc)_2$ | Palladium acetate | | |
| $Pd(dppf)Cl_2$ | [1,1'-Bis(diphenylphosphino)ferrocene]dichloropalladium(II) | | |
| Xant-Phos | 4,5-Bis(diphenylphosphino)-9,9-dimethyl-xanthene | | |

General Conditions and Procedures

In the following examples, the chemical reagents were purchased from commercial sources (such as Alfa, Acros, Sigma Aldrich, TCI and Shanghai Chemical Reagent Company), and used without further purification. THF was continuously refluxed and freshly distilled from sodium and benzophenone under nitrogen, dichloromethane was continuously refluxed and freshly distilled from $CaH_2$ under nitrogen.

Flash chromatography was performed on an Ez Purifier III via column with silica gel particles of 200-300 mesh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland) at around 20-30° C. unless otherwise specified. The following abbreviations are used: s, singlet; d, doublet; t, triplet; q, quartet; m, multiplet; dd, doublet of doublets; ddd, doublet of doublet of doublet; dt, doublet of triplets; bs, broad signal. Chemical shifts were reported in parts per million (ppm, δ) downfield from tetramethylsilane. Mass spectra were run with electrospray ionization (ESI) from a Waters LCT TOF Mass Spectrometer (Waters, USA). Compound purification was carried out as needed using a variety of traditional methods including, but not limited to, preparative chromatography under acidic, neutral, or basic conditions using either normal phase or reverse phase HPLC or flash columns or Prep-TLC plates.

Preparative HPLC: unless otherwise described, the compounds were purified using a WATERS Fractionlynx system equipped with a YMC Pack Pro ds Column (5 m, 120 A, 50×20 mm) and the following solvent system: $H_2O$, AcCN, and 2% TFA in H₂O. Specific elution gradients were based on the retention times obtained with an analytical LC-MS, however, in general all elution gradients of H₂O and MeCN were run over a 7 minutes run time with a flow rate of 35 mL/min. An auto-blend method was used to ensure a concentration of 0.1% TFA throughout each run. Specific elution gradients were based on the retention times obtained with an analytical LC-MS, however, in general, all elution gradients of H₂O and MeCN were run over at 8 minutes run time with a flow rate of 50 mL/min.

Analytical LC-MS: analytical LC-MS was performed on a WATERS Acquity UPLC-MS instrument equipped with a ACQUITY UPLC BEH $C_{i8}$ Column (2.1×50 mm, 1.7μη), a column temperature of 45° C. and using the following solvent system: Solvent A: 0.1% HCOOH in H₂O; and Solvent B: 0.1% HCOOH in AcCN. All compounds were run using the same elution gradient, i.e., 5% to 95% Solvent B over a 1.5 min run time with a flow rate of 0.6 mL/min.

Preparative Chiral SFC Separation: stereoisomer mixtures were separated using a Berger Minigram SFC instrument on one of the following columns: ChiralPak AS-H (10×250 mm), ChiralPak IA (10×250 mm), ChiralPak AD-H (21×250 mm), Phenomenex Lux-2 (21.2×250 mm), or ChiralPak IC (10×250 mm); eluting with either 0.1% diethylamine in MeOH/CO₂, or 0.1% diethylamine in EtOH/CO₂ or 0.1% diethylamine in isopropanol/CO₂ with a flow rate of 2.5 mL/min and a column temperature of 35° C.

Analytical Chiral SFC Separation: stereoisomer mixtures or single enantiomers were analyzed using a JASCO analytical SFC instrument on one of the following columns: ChiralPak AS-H (4.6×250 mm), ChiralPak IA (4.6×250 mm), ChiralPak AD-H (4.6×250 mm), Phenomenex Lux-2 (4.6×250 mm), or ChiralPak IC (4.6×250 mm); eluting with either 0.1% diethylamine in MeOH/CO₂, or 0.1% diethylamine in EtOH/CO₂ or 0.1% diethylamine in isopropanol/CO₂, with a flow rate of 6.0 mL/min and a column temperature of 35° C.

PREPARATION OF INTERMEDIATES

Intermediate A1 & A2: (R)-4-cyclopropyl-6,7-dihydro-4H-pyrazolo[5,1-c][1,4]oxazine-2-sulfonamide & (S)-4-cyclopropyl-6,7-dihydro-4H-pyrazolo[5,1-c][1,4]oxazine-2-sulfonamide

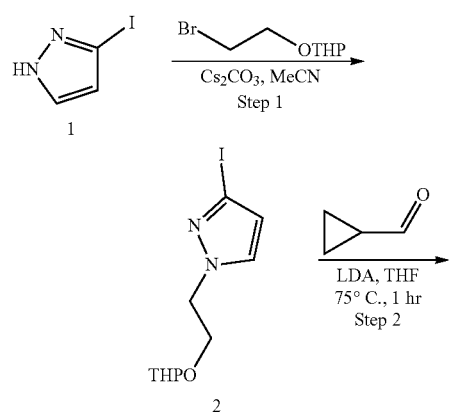

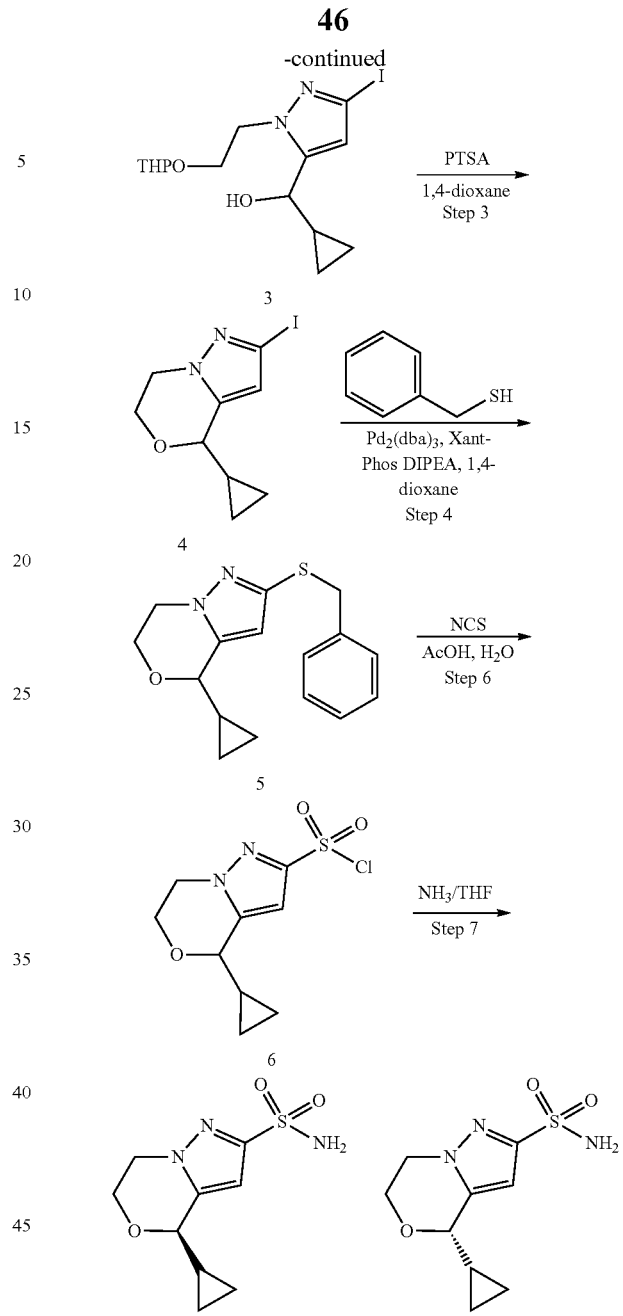

Step 1: 3-iodo-1-(2-((tetrahydro-2H-pyran-2-yl)oxy)ethyl)-1H-pyrazole

To a stirred solution of 3-iodo-1H-pyrazole (3 g, 15 mmol) in MeCN (30 mL) was added 2-(2-bromoethoxy)tetrahydro-2H-pyran (3.8 g, 18 mmol) and Cs₂CO₃ (15 g, 46 mmol) at r.t. After being stirred at r.t. for 3 hrs, the mixture was filtered. The filtrate was poured into water and extracted with EtOAc (2×10 mL). The combined organic phases were washed with water and brine, dried over anhydrous Na₂SO₄, filtered and concentrated to dryness. The residue was purified by flash chromatography (silica gel, 0-50% EtOAc in PE) to give the title compound (2 g, 40% yield) as colorless oil. LC/MS (ESI) m/z: 323 (M+H)⁺.

Step 2: cyclopropyl(3-iodo-1-(2-((tetrahydro-2H-pyran-2-yl)oxy)ethyl)-1H-pyrazol-5-yl)methanol To a stirred solution of 3-iodo-1-(2-((tetrahydro-2H-pyran-2-yl)oxy)ethyl)-1H-pyrazole (2 g, 6.2 mmol) in THF (30 mL) was added LDA (3.5 mL, 7 mmol, 2M in THF) drop-wisely at −75° C. After being stirred at −75° C. for 30 min, cyclopropanecarbaldehyde (0.5 mL, 6.2 mmol) was added to the mixture and the resulting mixture was stirred at −75° C. for 1 hr. The mixture was poured into ice-water and extracted with EtOAc (2×10 mL). The combined organic phases were washed with water and brine, dried over anhydrous $Na_2SO_4$, filtered and concentrated to dryness. The residue was purified by flash chromatography (silica gel, 0-30% EtOAc in PE) to give the title compound (1.4 g, 57% yield) as colorless oil. LC/MS (ESI) m/z: 309 (M+H)$^+$.

Step 3: 4-cyclopropyl-2-iodo-4H,6H,7H-pyrazolo[3,2-c][1,4]oxazine

To a stirred solution of 2-(5-(cyclopropyl(hydroxy)methyl)-3-iodo-1H-pyrazol-1-yl)ethan-1-ol (1.4 g, 3.6 mmol) in DCE (20 mL) was added PTSA (0.31 g, 1.8 mmol) and the mixture was stirred at 95° C. for 3 hrs. The mixture was poured into ice-water and extracted with DCM (2×20 mL). The combined organic phases were washed with water and brine, dried over anhydrous $Na_2SO_4$, filtered and concentrated to dryness. The residue was purified by flash chromatography (silica gel, 0-50% EtOAc in PE) to give the title compound (400 mg, 38% yield) as white solid. LC/MS (ESI) m/z: 291 (M+H)$^+$.

Step 4: 2-(benzylsulfanyl)-4-cyclopropyl-4H,6H,7H-pyrazolo[3,2-c][1,4]oxazine To a stirred solution of 4-cyclopropyl-2-iodo-4H,6H,7H-pyrazolo[3,2-c][1,4]oxazine (400 mg, 1.36 mmol) in 1,4-dioxane (15 mL) was added phenylmethanethiol (0.2 mL, 1.8 mmol), $Pd_2(dba)_3$ (140 mg, 0.16 mmol), Xant-Phos (180 mg, 0.32 mmol) and DIPEA (1 mL, 6 mmol) under $N_2$ atmosphere. The mixture was degassed under $N_2$ atmosphere for three times and stirred under $N_2$ atmosphere at 95° C. for 3 hrs. The mixture was diluted with EtOAc, washed with water and brine, dried over anhydrous $Na_2SO_4$, filtered and concentrated to dryness. The residue was purified by flash chromatography (silica gel, 0-50% EtOAc in PE) to give the title compound (360 mg, 91% yield) as yellow solid. LC/MS (ESI) m/z: 287 (M+H)$^+$.

Step 5: 4-cyclopropyl-4H,6H,7H-pyrazolo[3,2-c][1,4]oxazine-2-sulfonyl chloride To a stirred solution of 2-(benzylsulfanyl)-4-cyclopropyl-4H,6H,7H-pyrazolo[3,2-c][1,4]oxazine (360 mg, 1.26 mmol) in AcOH (8 mL)/$H_2O$ (2 mL) was added NCS (738 mg, 5.5 mmol) at 0° C. and the mixture was stirred at r.t. for 3 hrs. The mixture was poured into ice-water and extracted with EtOAc (2×10 mL). The combined organic phases were washed with water and brine, dried over $Na_2SO_4$, filtered and concentrated to dryness to give the title compound (300 mg, 90% yield) as yellow oil, which was directly used in the next reaction without purification.

Step 6: (R)-4-cyclopropyl-6,7-dihydro-4H-pyrazolo[5,1-c][1,4]oxazine-2-sulfonamide & (S)-4-cyclopropyl-6,7-dihydro-4H-pyrazolo[5,1-c][1,4]oxazine-2-sulfonamide A mixture of 4-cyclopropyl-4H,6H,7H-pyrazolo[3,2-c][1,4]oxazine-2-sulfonyl chloride (300 mg, 1.14 mmol) in $NH_3$/THF (20 mL, 1M) was stirred at r.t. for 1 hr. The mixture was poured into ice-water and extracted with DCM (3×10 mL). The combined organic phases were washed with water and brine, dried over anhydrous $Na_2SO_4$, filtered and concentrated to dryness. The residue was purified by flash chromatography (silica gel, 0-50% EtOAc in PE) to give 4-cyclopropyl-6,7-dihydro-4H-pyrazolo[5,1-c][1,4]oxazine-2-sulfonamide (180 mg, 64.8% yield) as off-white solid, which was repurified by chiral SFC to give arbitrarily assigned (R)-4-cyclopropyl-6,7-dihydro-4H-pyrazolo[5,1-c][1,4]oxazine-2-sulfonamide (Intermediate A1, 80 mg, 28.8% yield) and (S)-4-cyclopropyl-6,7-dihydro-4H-pyrazolo[5,1-c][1,4]oxazine-2-sulfonamide (Intermediate A2, 85 mg, 30.6% yield) as white solid.

Intermediate A1 (peak 1, retention time: 5.728 min), $^1$H NMR (400 MHz, DMSO-$d_6$) δ 7.42 (s, 1H), 6.51 (s, 1H), 4.29-4.25 (m, 1H), 4.16-4.13 (m, 2H), 4.05-4.03 (d, J=8.8 Hz, 1H), 3.94-3.90 (m, 1H), 1.16-1.14 (m, 1H), 0.69-0.67 (m, 1H), 0.59-0.51 (m, 2H), 0.47-0.45 (m, 2H). LC/MS (ESI) m/z: 244 (M+H)$^+$.

Intermediate A2 (peak 2, retention time: 6.700 min), $^1$H NMR (400 MHz, DMSO-$d_6$) δ 7.42 (s, 1H), 6.52 (s, 1H), 4.29-4.25 (m, 1H), 4.16-4.13 (m, 2H), 4.05-4.03 (d, J=8.8 Hz, 1H), 3.94-3.89 (m, 1H), 1.17-1.12 (m, 1H), 0.69-0.67 (m, 1H), 0.58-0.52 (m, 2H), 0.47-0.45 (m, 2H). LC/MS (ESI) m/z: 244 (M+H)$^+$.

SFC condition: Column: ChiralPak IC-H, 250×21.2 mm I.D., 5 μm; Mobile phase: A for $CO_2$ and B for Methanol (0.1% $NH_4OH$); Gradient: B 25%; Flow rate: 50 mL/min.

Intermediate A3: 6',7'-dihydrospiro[cyclobutane-1,4'-pyrazolo[5,1-c][1,4]oxazine]-2'-sulfonamide

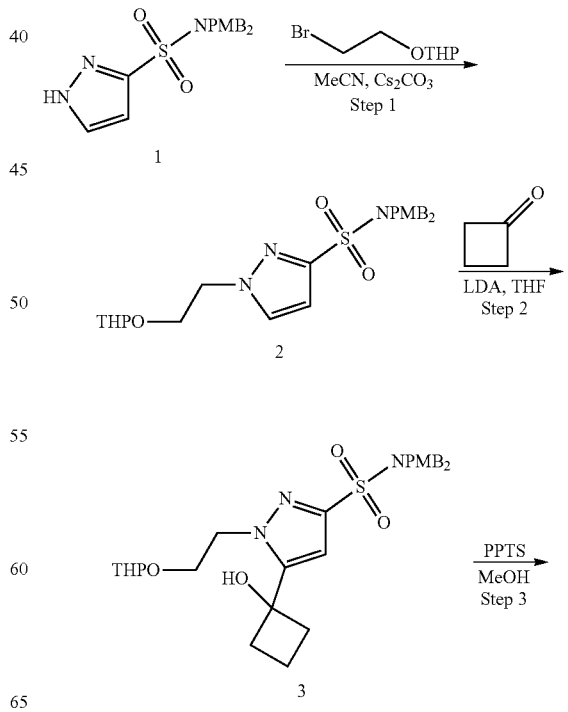

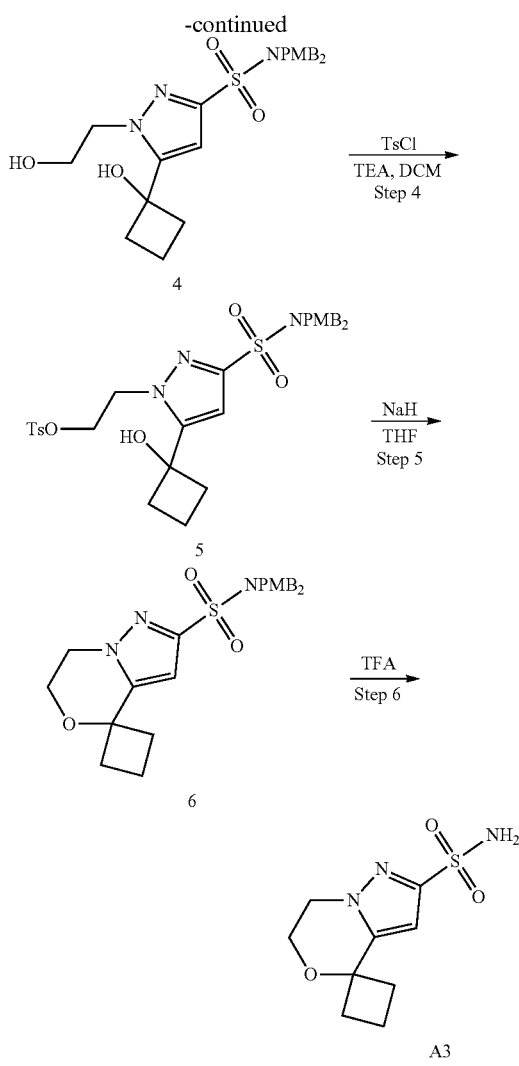

Step 1: N,N-bis(4-methoxybenzyl)-1-(2-((tetrahydro-2H-pyran-2-yl)oxy)ethyl)-1H-pyrazole-3-sulfonamide To a solution of N,N-bis(4-methoxybenzyl)-1H-pyrazole-3-sulfonamide (2 g, 5.16 mmol) in MeCN (25 mL) was added 2-(2-bromoethoxy)tetrahydro-2H-pyran (1.0 mL, 6.71 mmol) and $Cs_2CO_3$ (3.4 g, 10.3 mmol) and the mixture reaction was stirred at 65° C. under $N_2$ atmosphere for 16 hrs. The reaction mixture was poured into water and extracted with EtOAc (3×20 mL). The combined organic layers were washed with brine, dried over anhydrous $Na_2SO_4$, filtered and concentrated to dryness. The residue was purified by flash chromatography (silica gel, 0-50% EtOAc in PE) to give title compound (2.1 g, 94.3% yield) as yellow solid. LC/MS (ESI) (m/z): 516 (M+H)$^+$.

Step 2: 5-(1-hydroxycyclobutyl)-N,N-bis(4-methoxybenzyl)-1-(2-((tetrahydro-2H-pyran-2-yl)oxy)ethyl)-1H-pyrazole-3-sulfonamide To a solution of N,N-bis(4-methoxybenzyl)-1-(2-((tetrahydro-2H-pyran-2-yl)oxy)ethyl)-1H-pyrazole-3-sulfonamide (700 mg, 1.62 mmol) in THF (8 mL) was added LDA (1.1 mL, 2.2 mmol, 2M in THF) drop-wisely at −70° C. and the mixture was stirred at this temperature for 1 hr. A solution of cyclobutanone (0.13 mL, 1.78 mmol) in THF (4 mL) was added drop-wisely at −70° C. and the resulting mixture was stirred at −70° C. to r.t. for 2 hrs. The reaction mixture was quenched with ice-cooled saturated aq·$NH_4Cl$ solution and extracted with EtOAc (2×10 mL). The combined organic layers were washed with brine, dried with anhydrous $Na_2SO_4$, filtered and concentrated to dryness. The residue was purified by flash chromatography (silica gel, 0-30% of EtOAc in PE) to give the title compound (200 mg, 24.6% yield) as yellow solid. LC/MS (ESI) (m/z): 586 (M+H)$^+$.

Step 3: 5-(1-hydroxycyclobutyl)-1-(2-hydroxyethyl)-N,N-bis(4-methoxybenzyl)-1H-pyrazole-3-sulfonamide To a solution of 5-(1-hydroxycyclobutyl)-N,N-bis(4-methoxybenzyl)-1-(2-((tetrahydro-2H-pyran-2-yl)oxy)ethyl)-1H-pyrazole-3-sulfonamide (100 mg, 0.17 mmol) in MeOH (5 mL) was added PPTS (43 mg, 0.17 mmol) and the mixture reaction was stirred at 50° C. for 1 hr. The mixture was diluted with EtOAc, washed with water and brine, dried over anhydrous $Na_2SO_4$, filtered and concentrated to dryness. The residue was purified by flash chromatography (silica gel, 0-50% of EtOAc in PE) to give the title compound (40 mg, 46.6% yield) as yellow oil. LC/MS (ESI) (m/z): 502 (M+H)$^+$.

Step 4: 2-(3-(N,N-bis(4-methoxybenzyl)sulfamoyl)-5-(1-hydroxycyclobutyl)-1H-pyrazol-1-yl)ethyl 4-methylbenzenesulfonate To a solution of 5-(1-hydroxycyclobutyl)-1-(2-hydroxyethyl)-N,N-bis(4-methoxybenzyl)-1H-pyrazole-3-sulfonamide (100 mg, 0.20 mmol) in DCM (5 mL) was added TosCl (38 mg, 0.20 mmol), DIPEA (77 mg, 0.60 mmol) and DMAP (24 mg, 0.20 mmol) and the mixture was stirred at room temperature for 30 minutes. The mixture was diluted with DCM, washed with water and brine, concentrated to dryness. The residue was purified by flash chromatography (silica gel, 0-30% of EtOAc in PE) to give the title compound (105 mg, 80% yield) as yellow solid. LC/MS (ESI) (m/z): 656 (M+H)$^+$.

Step 5: N,N-bis(4-methoxybenzyl)-6',7'-dihydrospiro[cyclobutane-1,4'-pyrazolo[5,1-c][1,4]oxazine]-2'-sulfonamide To a solution of 2-(3-(N,N-bis(4-methoxybenzyl)sulfamoyl)-5-(1-hydroxycyclobutyl)-1H-pyrazol-1-yl)ethyl 4-methylbenzenesulfonate (80 mg, 0.12 mmol) in THF (3 mL) was added NaH (10 mg, 0.24 mmol, 60% dispersion in mineral oil) at 0° C. and the mixture reaction was stirred at r.t. for 30 minutes. The reaction was quenched with ice-water and extracted with EtOAc (3×10 mL). The combined organic layers were washed with brine, dried over anhydrous $Na_2SO_4$, filtered and concentrated to dryness. The residue was purified by flash chromatography (silica gel, 0-30% of EtOAc in PE) to give the title compound (40 mg, 67.8% yield) as yellow solid. LC/MS (ESI) (m/z): 484 (M+H)$^+$.

Step 6: 6',7'-dihydrospiro[cyclobutane-1,4'-pyrazolo[5,1-c][1,4]oxazine]-2'-sulfonamide A solution of N,N-bis(4-methoxybenzyl)-6',7'-dihydrospiro[cyclobutane-1,4'-pyrazolo[5,1-c][1,4]oxazine]-2'- sulfonamide (40 mg, 0.08 mmol) in TFA (3 mL) was stirred at r.t. for 2 hrs. The mixture was concentrated to dryness and the residue was dissolved in EtOAc, washed with water and brine, dried over $Na_2SO_4$, filtered and concentrated to dryness to give the title compound (15 mg, 74.6% yield) as yellow solid. LC/MS (ESI) (m/z): 244 $(M+H)^+$.

Intermediate A4: 8-cyclopropyl-5,6-dihydro-8H-imidazo[2,1-c][1,4]oxazine-2-sulfonamide

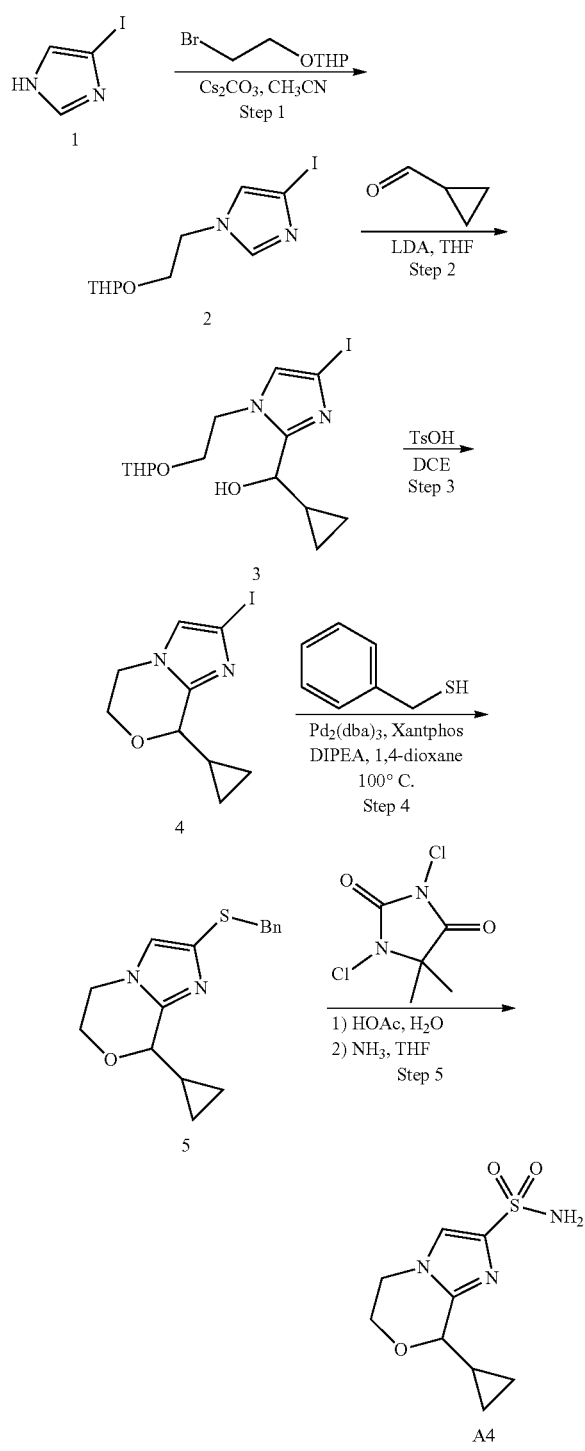

Step 1: 4-iodo-1-[2-(oxan-2-yloxy)ethyl]-1H-imidazole

To a mixture of 4-iodo-1H-imidazole (2.0 g, 10.3 mmol) and 2-(2-bromoethoxy)oxane (2.6 g, 12.4 mmol) in $CH_3CN$ (30 mL) was added $Cs_2CO_3$ (5.0 g, 15.5 mmol) and the mixture was stirred at 60° C. for 3 hrs. The mixture was diluted with EtOAc, washed with water and brine, dried over $Na_2SO_4$, filtered and concentrated to dryness. The residue was purified by flash chromatography (silica gel, 0-30% EtOAc in PE) to give the title compound (1.7 g, 51% yield) as light yellow oil. LC/MS (ESI) m/z: 323 $(M+H)^+$.

Step 2: cyclopropyl({4-iodo-1-[2-(oxan-2-yloxy)ethyl]-1H-imidazol-2-yl})methanol To a solution of 4-iodo-1-[2-(oxan-2-yloxy)ethyl]-1H-imidazole and 5-iodo-1-[2-(oxan-2-yloxy)ethyl]-1H-imidazole (1.7 g, 5.3 mmol) in THF (30 mL) was added LDA (4 mL, 2M in hexane) drop-wisely at −70° C. After being stirred at this temperature for 30 min, cyclopropanecarbaldehyde (440 mg, 6.3 mmol) was added and the resulting mixture was stirred at −70° C. to room temperature for 2 hrs. The reaction was poured into ice-water and extracted with EtOAc (2×20 mL). The organic layers were washed with brine, dried over anhydrous $Na_2SO_4$, filtered and concentrated to dryness. The residue was purified by flash chromatography (silica gel, 0-50% EtOAc in PE) to give the title compound (1.2 g, 58% yield) as colorless oil. LC/MS (ESI) m/z: 393 $(M+H)^+$.

Step 3: 8-cyclopropyl-2-iodo-5H,6H,8H-imidazo[2,1-c][1,4]oxazine

To a solution of cyclopropyl({4-iodo-1-[2-(oxan-2-yloxy)ethyl]-1H-imidazol-2-yl})methanol (1.0 g, 2.5 mmol) in DCE (15 mL) was added PTSA (220 mg, 1.3 mmol) and the mixture was stirred at reflux for 2 hrs. The mixture was diluted with DCM (10 mL), washed with water and brine, dried over $Na_2SO_4$, filtered and concentrated to dryness. The residue was purified by flash chromatography (silica gel, 0-60% EtOAc in PE) to give the title compound (240 mg, 32% yield) as white solid. LC/MS (ESI) m/z: 291 $(M+H)^+$.

Step 4: 2-(benzylsulfanyl)-8-cyclopropyl-5H,6H,8H-imidazo[2,1-c][1,4]oxazine

To a solution of 8-cyclopropyl-2-iodo-5H,6H,8H-imidazo[2,1-c][1,4]oxazine (240 mg, 0.8 mmol), phenylmethanethiol (133 mg, 1.0 mmol) and DIPEA (320 mg, 2.5 mmol) in toluene (8 mL) was added $Pd_2(dba)_3$ (151 mg, 0.16 mmol), Xant-Phos (96 mg, 0.16 mmol) under $N_2$ atmosphere. The mixture was degassed under $N_2$ atmosphere for three times and stirred under $N_2$ atmosphere at 100° C. for 3 hrs. The mixture was concentrated to dryness and the residue was purified by flash chromatography (silica gel, 0-50% EtOAc in PE) to give the title compound (230 mg, 97% yield) as yellow oil. LC/MS (ESI) m/z: 286 $(M+H)^+$.

Step 5: 8-cyclopropyl-5H,6H,8H-imidazo[2,1-c][1,4]oxazine-2-sulfonamide

To a stirred solution of 2-(benzylsulfanyl)-8-cyclopropyl-5H,6H,8H-imidazo[2,1-c][1,4]oxazine (100 mg, 0.35 mmol) in AcOH (4 mL) and $H_2O$ (1 mL) was added 1,3-dichloro-5,5-dimethylhydantoin (206 mg, 1.0 mmol) in portions at 0° C. and the mixture was stirred at r.t. for 30 min. The reaction mixture was diluted with DCM, washed with water and brine, dried over anhydrous Na₂SO₄, filtered and concentrated to dryness. The residue was dissolved in THF (1 mL) and NH₃/THF (2 mL, 1M) was added drop-wisely at 0° C. After being stirred at r.t. for 1 hr, the mixture was concentrated to dryness. The residue was purified by flash chromatography (silica gel, 0-60% EtOAc in PE) to give the title compound (40 mg, 47% yield) as white solid. LC/MS (ESI) m/z: 244 (M+H)⁺.

Intermediate A5: 4,4-dimethyl-6,7-dihydro-4H-pyrazolo[5,1-c][1,4]oxazine-2-sulfonamide

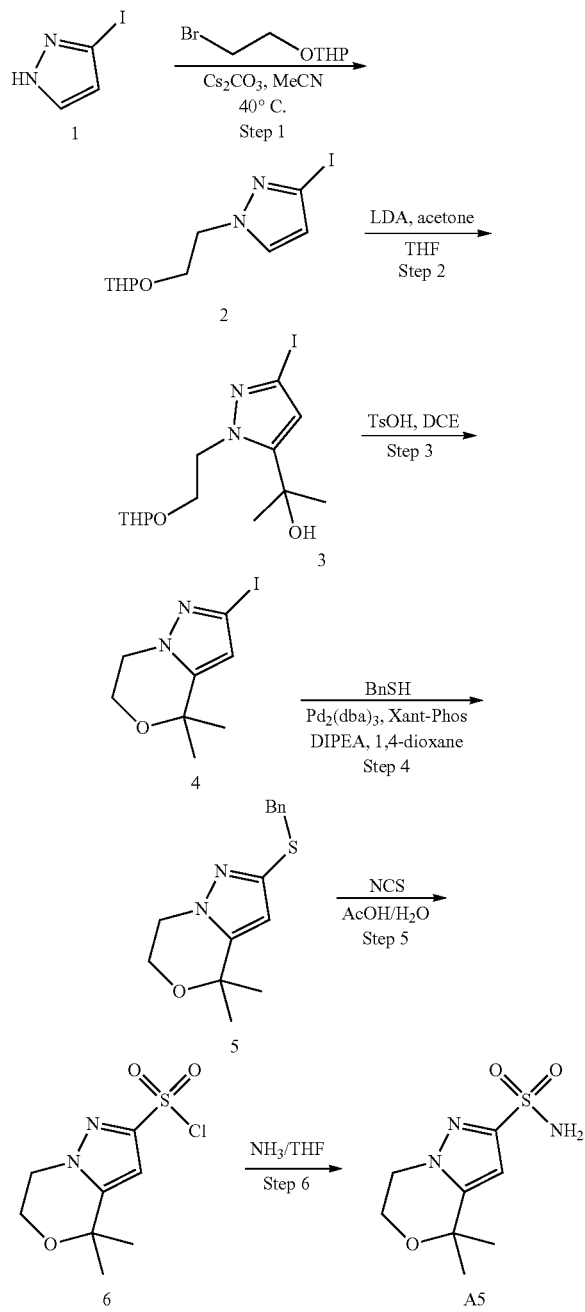

Step 1: 3-iodo-1-[2-(oxan-2-yloxy)ethyl]-1H-pyrazole

To a stirred solution of 3-iodo-1H-pyrazole (5 g, 26 mmol) in MeCN (100 mL) was added 2-(2-bromoethoxy)tetrahydro-2H-pyran (4.7 mL, 31 mmol) and Cs₂CO₃ (17 g, 51 mmol) and the mixture was stirred at 40° C. for 2 hrs. The mixture was diluted with EtOAc, washed with water and brine, dried over Na₂SO₄, filtered and concentrated to dryness. The residue was purified by flash chromatography (silica gel, 0-30% EtOAc in PE) to give the title compound (8 g, 96% yield) as colorless oil. LC/MS (ESI) m/z: 323 (M+H)⁺.

Step 2: 2-{3-iodo-1-[2-(oxan-2-yloxy)ethyl]-1H-pyrazol-5-yl}propan-2-ol

To a stirred solution of 3-iodo-1-[2-(oxan-2-yloxy)ethyl]-1H-pyrazole (2 g, 6.2 mmol) in THF (30 mL) was added LDA (3.8 mL, 7.1 mmol, 2M in THF) drop-wisely at −75° C. After being stirred at −75° C. for 30 min, acetone (1 mL, 18 mmol) was added to the mixture drop-wisely and the resulting mixture was stirred at −75° C. for 1 hr. The mixture was poured into ice-water and extracted with EtOAc (2×15 mL). The combined organic phases were washed with water and brine, dried over Na₂SO₄, filtered and concentrated to dryness. The residue was purified by flash chromatography (silica gel, 0-50% EtOAc in PE) to give the title compound (1.1 g, 46% yield) as light yellow oil. LC/MS (ESI) m/z: 381 (M+H)⁺.

Step 3: 2-iodo-4,4-dimethyl-4H,6H,7H-pyrazolo[3,2-c][1,4]oxazine

To a stirred solution of 2-{3-iodo-1-[2-(oxan-2-yloxy)ethyl]-1H-pyrazol-5-yl}propan-2-ol (1.1 g, 2.9 mmol) in DCE (20 mL) was added PTSA (0.3 g, 1.8 mmol) and the mixture was stirred at 95° C. for 3 hrs. The mixture was poured into ice-water and extracted with DCM (2×20 mL). The combined organic phases were washed with water and brine, dried over anhydrous Na₂SO₄, filtered and concentrated to dryness. The residue was purified by flash chromatography (silica gel, 0-80% EtOAc in PE) to give the title compound (500 mg, 62% yield) as yellow oil. LC/MS (ESI) m/z: 279 (M+H)⁺.

Step 4: 2-(benzylsulfanyl)-4,4-dimethyl-4H,6H,7H-pyrazolo[3,2-c][1,4]oxazine

To a stirred solution of 2-iodo-4,4-dimethyl-4H,6H,7H-pyrazolo[3,2-c][1,4]oxazine (500 mg, 1.8 mmol) in 1,4-dioxane (15 mL) was added phenylmethanethiol (0.2 mL, 1.9 mmol), Pd₂(dba)₃ (140 mg, 0.16 mmol), Xant-Phos (190 mg, 0.33 mmol) and DIPEA (1 mL, 6 mmol) under N₂ atmosphere, the mixture was degassed under N₂ atmosphere for three times and stirred under N₂ atmosphere at 95° C. for 3 hrs. The mixture was diluted with EtOAc, washed with water and brine, dried over anhydrous Na₂SO₄, filtered and concentrated to dryness. The residue was purified by flash chromatography (silica gel, 0-50% EtOAc in PE) to give the title compound (400 mg, 81% yield) as yellow solid. LC/MS (ESI) m/z: 275 (M+H)⁺.

Step 5: 4,4-dimethyl-4H,6H,7H-pyrazolo[3,2-c][1,4]oxazine-2-sulfonyl chloride

To a stirred solution of 2-(benzylsulfanyl)-4,4-dimethyl-4H,6H,7H-pyrazolo[3,2-c][1,4]oxazine (200 mg, 0.72 mmol) in AcOH (8 mL)/H₂O (2 mL) was added NCS (738 mg, 5.5 mmol) in portions at 0° C. and the mixture was stirred at r.t. for 1 hr. The mixture was poured into water and extracted with DCM (2×10 mL). The combined organic layers were washed with water and brine, dried over anhydrous Na₂SO₄, filtered and concentrated to dryness to give the title compound (120 mg, 66% yield) as colorless oil, which was directly used in the next reaction without purification.

Step 6: 4,4-dimethyl-4H,6H,7H-pyrazolo[3,2-c][1,4]oxazine-2-sulfonamide

A mixture of 4,4-dimethyl-4H,6H,7H-pyrazolo[3,2-c][1,4]oxazine-2-sulfonyl chloride (120 mg, 0.48 mmol) in NH₃/THF (20 mL, 2M) was stirred at r.t. for 1 hr. The mixture was poured into ice-water and extracted with DCM (3×10 mL). The combined organic phases were washed with water and brine, dried over Na₂SO₄, filtered and concentrated to dryness. The residue was purified by chromatography (silica gel, 0-50% EtOAc in PE) to give the title compound (40 mg, 36% yield) as white solid. LC/MS (ESI) m/z: 232 (M+H)⁺.

Intermediate A6: 6,7-dihydro-4H-pyrazolo[5,1-c][1,4]oxazine-2-sulfonamide

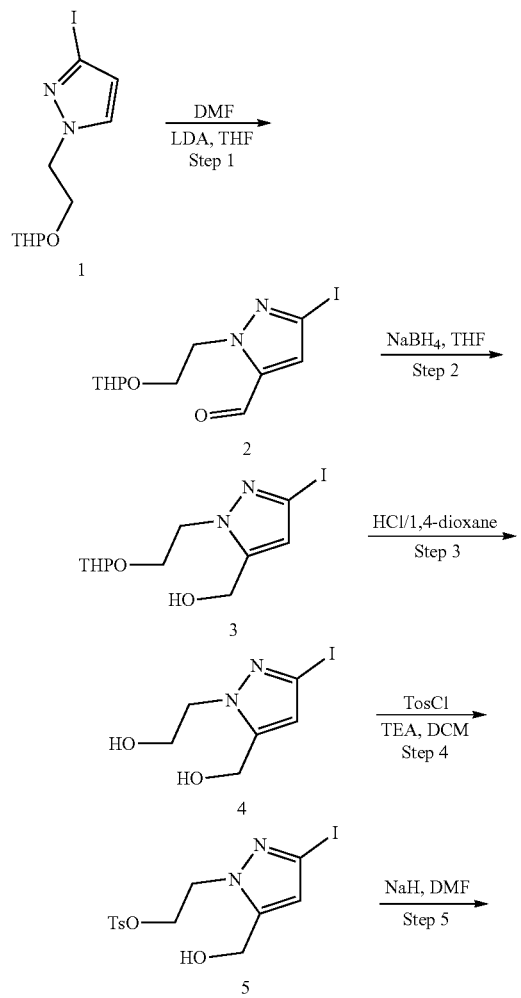

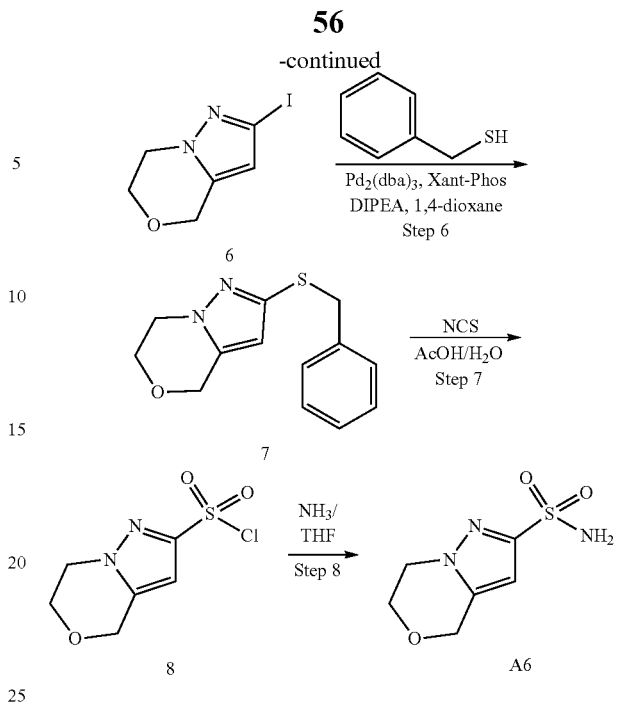

Step 1: 3-iodo-1-(2-((tetrahydro-2H-pyran-2-yl)oxy)ethyl)-1H-pyrazole-5-carbaldehyde To a solution of 3-iodo-1-[2-(oxan-2-yloxy)ethyl]-1H-pyrazole (2 g, 6.2 mmol) in THF (10 mL) was added LDA (3.7 mL, 7.4 mmol, 2M in THF) at −70° C. and the mixture was stirred at −70° C. for 0.5 hr. A solution of DMF (0.9 mL, 12.4 mmol) in THF (5 mL) was added to the mixture drop-wisely at −70° C. and the resulting mixture was stirred at −70° C. to r.t. for 2 hrs. The reaction mixture was poured into saturated aq·NH₄Cl solution and extracted with EtOAc (2×20 mL). The combined organic layers were washed with brine, dried over Na₂SO₄, filtered and concentrated to dryness. The residue was purified by flash chromatography (silica gel, 0-20% EtOAc in PE) to give the title compound (1.1 g, 50.6% yield) as light yellow oil. LC/MS (ESI) (m/z). 351(M+H)⁺.

Step 2: (3-iodo-1-(2-((tetrahydro-2H-pyran-2-yl)oxy)ethyl)-1H-pyrazol-5-yl)methanol To a solution of 3-iodo-1-[2-(oxan-2-yloxy)ethyl]-1H-pyrazole-5-carbaldehyde (1.1 g, 3.1 mmol) in THF (15 mL) was added NaBH₄ (178 mg, 4.7 mmol) in portions at 0° C. and the mixture was stirred at r.t. for 0.5 hr. The reaction mixture was poured into ice-water and extracted with EtOAc (2×10 mL). The combined organic layers were washed with brine, dried over Na₂SO₄, filtered and concentrated to dryness. The residue was purified by flash chromatography (silica gel, 0-20% EtOAc in PE) to give the title compound (950 mg, 85.8% yield) as colorless oil. LC/MS (ESI) (m/z): 353 (M+H)⁺.

Step 3: 2-(5-(hydroxymethyl)-3-iodo-1H-pyrazol-1-yl)ethan-1-ol

A solution of 5-[(R)-cyclopropyl(methoxy)methyl]-1-methyl-1H-pyrazole-3-sulfonyl chloride (1 g, 0.3 mmol) in HCl/1,4-dioxane (5 mL, 4M) was stirred at room temperature for 1 hr. The mixture was filtered and the filter cake was washed with PE, dried under vacuum to give the title compound (500 mg, 72.9% yield) as white solid. LC/MS (ESI) (m/z): 269 (M+H)+.

Step 4: 2-(5-(hydroxymethyl)-3-iodo-1H-pyrazol-1-yl)ethyl 4-methylbenzenesulfonate To a solution of 2-[5-(hydroxymethyl)-3-iodo-1H-pyrazol-1-yl]ethan-1-ol (300 mg, 1.1 mmol) in DCM (2 mL) was added TEA (0.5 mL, 3.4 mmol) and TosCl (0.2 mL, 1.1 mmol) at 0° C. and the mixture was stirred at r.t. for 16 hrs. The mixture was diluted with DCM, washed with water and brine, dried over Na$_2$SO$_4$, filtered and concentrated to dryness. The residue was purified by flash chromatography (silica gel, 0-50% EtOAc in PE) to give the title compound (240 mg, 50.7% yield) as colorless oil. LC/MS (ESI) (m/z): 423 (M+H)+.

Step 5: 2-iodo-6,7-dihydro-4H-pyrazolo[5,1-c][1,4]oxazine

To a solution of 2-[5-(hydroxymethyl)-3-iodo-1H-pyrazol-1-yl]ethyl 4-methylbenzene-1-sulfonate (240 mg, 0.57 mmol) in THE (2 mL) was added NaH (68 mg, 1.7 mmol, 60% dispersion in mineral oil) in portions at 0° C. and the mixture was stirred at r.t. for 1 hr. The mixture was poured into saturated aq·NH$_4$Cl solution and extracted with EtOAc (2×10 mL). The combined organic layers were washed with brine, dried over Na$_2$SO$_4$, filtered and concentrated to dryness. The residue was purified by flash chromatography (silica gel, 0-30% EtOAc in PE) to give the title compound (140 mg, 98.5% yield) as light yellow oil. LC/MS (ESI) (m/z): 251 (M+H)+.

Step 6: 2-(benzylthio)-6,7-dihydro-4H-pyrazolo[5,1-c][1,4]oxazine

To a mixture of 2-iodo-4H,6H,7H-pyrazolo[3,2-c][1,4]oxazine (150 mg, 0.60 mmol), phenylmethanethiol (0.07 mL, 0.6 mmol) and DIPEA (0.3 mL, 1.8 mmol) in 1,4-dioxane (10 mL) were added Pd$_2$(dba)$_3$ (110 mg, 0.1 mmol), XantPhos (139 mg, 0.2 mmol) under N$_2$ atmosphere. The mixture was degassed under N$_2$ atmosphere for three times and stirred at 100° C. for 2 hrs. The mixture was concentrated to dryness and the residue was purified by flash chromatography (silica gel, 0-40% EtOAc in PE) to give the title compound (140 mg, 94.7% yield) as yellow oil. LC/MS (ESI) (m/z): 247 (M+H)+

Step 7: 6,7-dihydro-4H-pyrazolo[5,1-c][1,4]oxazine-2-sulfonyl chloride

To a solution of 2-(benzylsulfanyl)-4H,6H,7H-pyrazolo[3,2-c][1,4]oxazine (140 mg, 0.57 mmol) in H$_2$O (1 mL) and AcOH (5 mL) was added NCS (379 mg, 2.8 mmol) in portions at 0° C. and the mixture was stirred at r.t. for 1 hr. The reaction mixture was poured into water and extracted with EtOAc (2×5 mL). The combined organic layers were washed with brine, dried over anhydrous Na$_2$SO$_4$, filtered and concentrated to dryness. The residue was purified by flash chromatography (silica gel, 0-50% EtOAc in PE) to give the title compound (90 mg, 70.9% yield) as light yellow oil. LC/MS (ESI) (m/z): 223 (M+H)+

Step 8: 6,7-dihydro-4H-pyrazolo[5,1-c][1,4]oxazine-2-sulfonamide

To a solution of 6,7-dihydro-4H-pyrazolo[5,1-c][1,4]oxazine-2-sulfonyl chloride (70 mg, 0.31 mmol) in THE (2 mL) was added NH$_3$/THF (2 mL, 1M) at 0° C. and the mixture was stirred at r.t. for 1 hr. The mixture was filtered and the filtrate was concentrated under vacuum to give the title compound (55 mg, 86.2% yield) as white solid. LC/MS (ESI) (m/z): 204 (M+H)+.

Intermediate A7: 6,7-dihydro-4H-pyrazolo[5,1-c][1,4]oxazine-3-sulfonamide

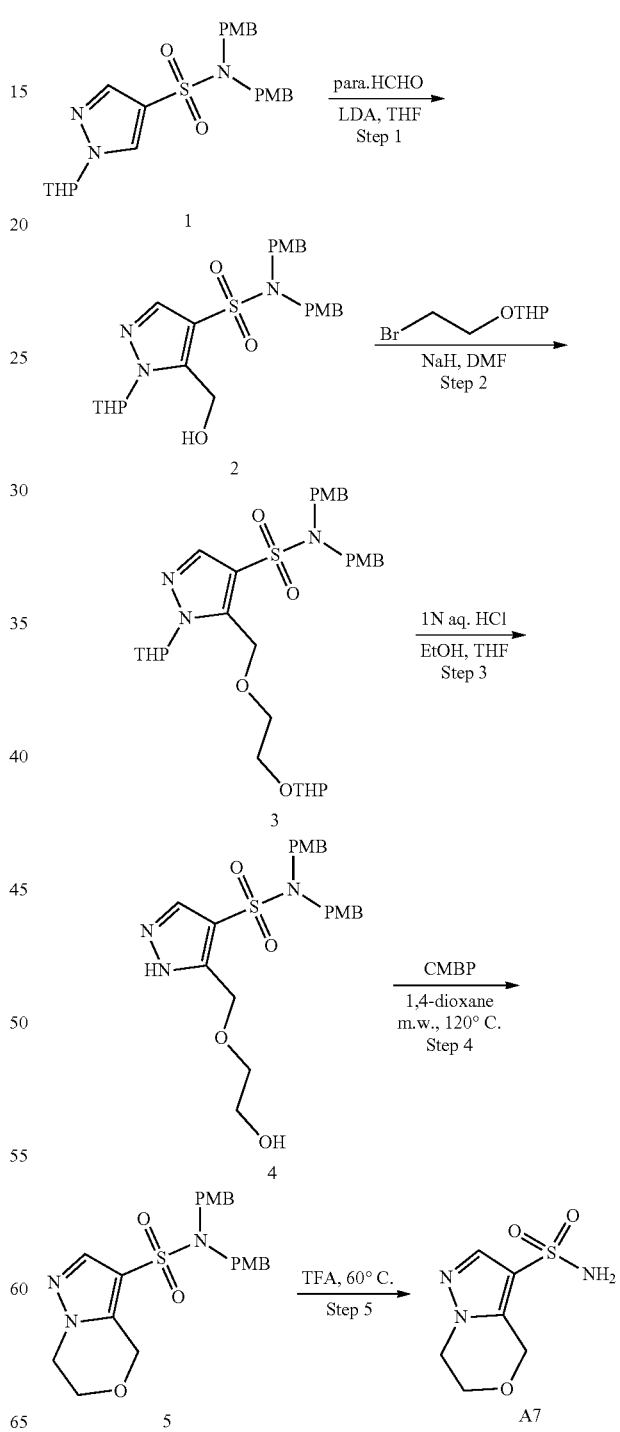

Step 1: 5-(hydroxymethyl)-N,N-bis[(4-methoxyphenyl)methyl]-1-(oxan-2-yl)-1H-pyrazole-4-sulfonamide To a solution of N,N-bis[(4-methoxyphenyl)methyl]-1-(oxan-2-yl)-1H-pyrazole-4-sulfonamide (2.0 g, 4.2 mmol) in THF (40 mL) was added LDA (3.2 mL, 6.4 mmol, 2M in THF) drop-wisely at −70° C. and the mixture was stirred at −70° C. for 30 min. Paraformaldehyde (380 mg, 12.7 mmol) was added and the mixture was stirred at −70° C. to r.t. for 2 hrs. The reaction was poured into ice-water and extracted with EtOAc (2×10 mL). The combined organic layers were washed with brine, dried over $Na_2SO_4$, filtered and concentrated to dryness. The residue was purified by flash chromatography (silica gel, 0-40% EtOAc in PE) to give the title compound (1.2 g, 56% yield) as brown oil. LC/MS (ESI) (m/z): 323 $(M+H)^+$.

Step 2: N,N-bis[(4-methoxyphenyl)methyl]-1-(oxan-2-yl)-5-{[2-(oxan-2-yloxy)ethoxy]methyl}-1H-pyrazole-4-sulfonamide To a solution of 5-(hydroxymethyl)-N,N-bis[(4-methoxyphenyl)methyl]-1-(oxan-2-yl)-1H-pyrazole-4-sulfonamide (300 mg, 0.6 mmol) in DMF (6 mL) was added NaH (36 mg, 0.9 mmol, 60% dispersion in mineral oil) at 0° C. After being stirred at 0° C. for 30 min, 2-(2-bromoethoxy)oxane (150 mg, 0.72 mmol) was added and the resulting mixture was stirred at r.t. for 16 hrs. The mixture was poured into ice-water and extracted with EtOAc (2×10 mL). The combined organic layers were washed with brine, dried over $Na_2SO_4$, filtered and concentrated to dryness. The residue was purified by flash chromatography (silica gel, 0-60% EtOAc in PE) to give the title compound (270 mg, 72% yield) as colorless oil. LC/MS (ESI) (m/z): 462 $(M-2THP+H)^+$.

Step 3: 5-[(2-hydroxyethoxy)methyl]-N,N-bis[(4-methoxyphenyl)methyl]-1H-pyrazole-4-sulfonamide To a solution of N,N-bis[(4-methoxyphenyl)methyl]-1-(oxan-2-yl)-5-{[2-(oxan-2-yloxy)ethoxy]methyl}-1H-pyrazole-4-sulfonamide (270 mg, 0.4 mmol) in EtOH (4 mL) and THF (4 mL) was added 1N aq·HCl (3 mL) and the mixture was stirred at room temperature for 16 hrs. The mixture was diluted with ice-water and extracted with EtOAc (2×10 mL). The combined organic layers were washed with brine, dried over $Na_2SO_4$, filtered and concentrated to dryness. The residue was purified by flash chromatography (silica gel, 0-8% MeOH in DCM) to give the title compound (150 mg, 76% yield) as colorless oil. LC/MS (ESI) (m/z): 462 $(M+H)^+$.

Step 4: N,N-bis[(4-methoxyphenyl)methyl]-4H,6H,7H-pyrazolo[3,2-c][1,4]oxazine-3-sulfonamide To a solution of 5-[(2-hydroxyethoxy)methyl]-N,N-bis[(4-methoxyphenyl)methyl]-1H-pyrazole-4-sulfonamide (150 mg, 0.3 mmol) in 1,4-dioxane (5 mL) was added cyanomethylenetributylphosphorane (157 mg, 0.6 mmol) under $N_2$ atmosphere and the mixture was stirred at 120° C. under CEM microwave reactor for 2 hrs. The mixture was concentrated to dryness and the residue was purified by flash chromatography (silica gel, 0-60% EtOAc in PE) to give the title compound (100 mg, 69% yield) as light yellow solid. LC/MS (ESI) (m/z): 444 $(M+H)^+$.

Step 5: 6,7-dihydro-4H-pyrazolo[5,1-c][1,4]oxazine-3-sulfonamide

A solution of N,N-bis[(4-methoxyphenyl)methyl]-4H,6H,7H-pyrazolo[3,2-c][1,4]oxazine-3-sulfonamide (100 mg, 0.2 mmol) in TFA (3 mL) was stirred at 60° C. for 2 hrs. The mixture was concentrated to dryness and the residue was purified by flash chromatography (silica gel, 0-60% EtOAc in PE) to give the title compound (35 mg, 86.1% yield) as yellow solid. LC/MS (ESI) (m/z): 204 $(M+H)^+$.

Intermediate A8: 7-cyclopropyl-6,7-dihydro-4H-pyrazolo[5,1-c][1,4]oxazine-2-sulfonamide

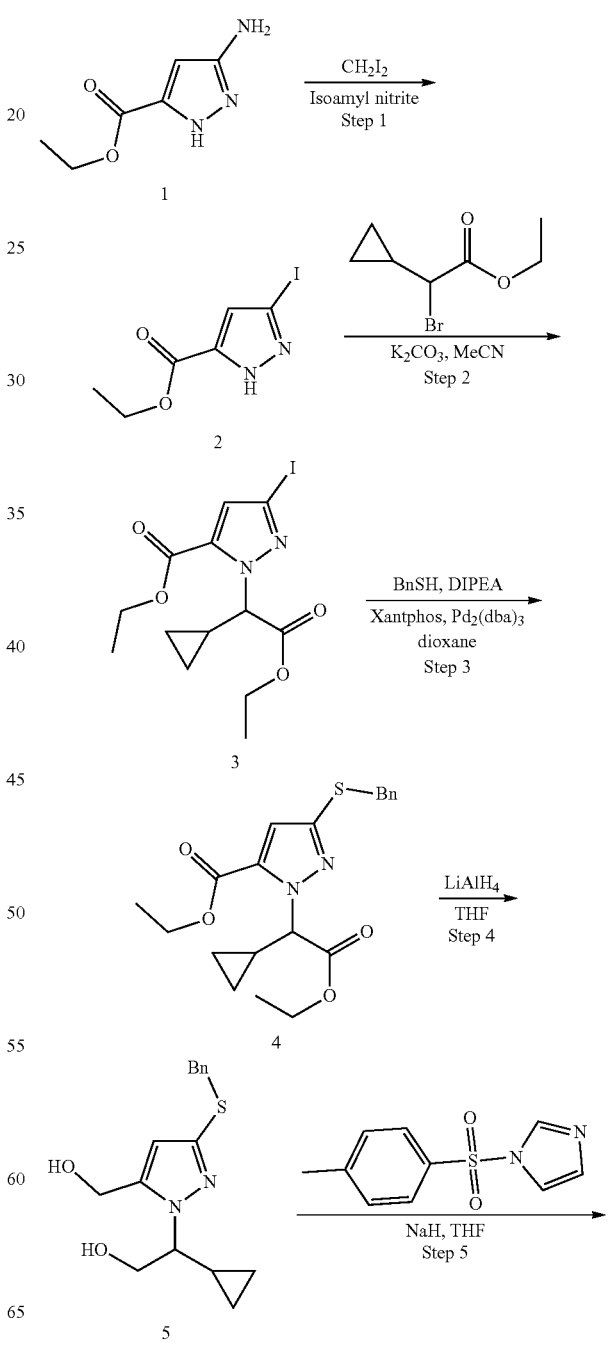

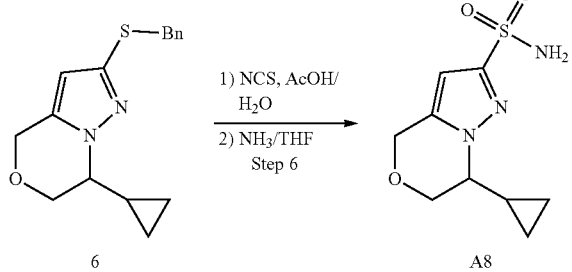

Step 1: ethyl 3-iodo-1H-pyrazole-5-carboxylate

To a solution of ethyl 5-amino-1H-pyrazole-3-carboxylate (2 g, 12.9 mmol) in diiodomethane (30 mL) was added isoamyl nitrite (15.6 mL, 116 mmol) at −10° C. under $N_2$ atmosphere over 20 mins. The mixture was stirred at r.t. for 1 hr and stirred at 90° C. for another 1 hr. The mixture was diluted with EtOAc (20 mL), washed with saturated aq·$Na_2S_2O_3$ solution, 1N aq·HCl and brine successively, dried over anhydrous $Na_2SO_4$, filtered and concentrated to dryness. The residue was purified by flash chromatography (silica gel, 0-30% EtOAc in PE) to give the title compound (1.4 g, 40.8% yield) as yellow solid. LC/MS (ESI) m/z: 266 (M+H)$^+$.

Step 2: ethyl 1-(1-cyclopropyl-2-ethoxy-2-oxo-ethyl)-3-iodo-1H-pyrazole-5-carboxylate To a mixture of ethyl 3-iodo-1H-pyrazole-5-carboxylate (1.27 g, 4.76 mmol) and ethyl 2-bromo-2-cyclopropylacetate (920 mg, 4.76 mmol) in MeCN (10 mL) was added $K_2CO_3$ (1.97 g, 14.3 mmol) and the mixture was stirred at 80° C. for 3 hrs. The mixture was diluted with EtOAc, washed with water and brine, dried over anhydrous $Na_2SO_4$, filtered and concentrated to dryness. The residue was purified by flash chromatography (silica gel, 0-9% of EtOAc in PE) to give the title compound (1.4 g, 75% yield) as colorless oil. $^1$H NMR (400 MHz, CDCl$_3$) δ 7.00 (s, 1H), 4.38 (q, J=7.1 Hz, 2H), 4.31 (d, J=10.1 Hz, 1H), 4.26-4.17 (m, 2H), 2.02-1.95 (m, 1H), 1.37 (t, J=7.1 Hz, 3H), 1.24 (t, J=7.1 Hz, 3H), 0.97-0.86 (m, 1H), 0.69-0.60 (m, 2H), 0.69-0.60 (m, 1H). LC/MS (ESI) m/z: 393 (M+H)$^+$.

Step 3: ethyl 3-(benzylthio)-1-(1-cyclopropyl-2-ethoxy-2-oxoethyl)-1H-pyrazole-5-carboxylate To a mixture of ethyl 1-(1-cyclopropyl-2-ethoxy-2-oxoethyl)-3-iodo-1H-pyrazole-5-carboxylate (460 mg, 1.17 mmol), benzyl mercaptan (0.23 mL, 1.88 mmol), DIPEA (0.62 mL, 3.74 mmol) and XantPhos (216 mg, 0.37 mmol) in 1,4-dioxane (5 mL) was added $Pd_2(dba)_3$ (171 mg, 0.19 mmol) under $N_2$ atmosphere. The mixture was degassed under $N_2$ atmosphere for three times and stirred at 90° C. overnight. The mixture was diluted with EtOAc, washed with water and brine, dried over anhydrous $Na_2SO_4$, filtered and concentrated to dryness. The residue was purified by flash chromatography (silica gel, 0-25% EtOAc in PE) to give the title compound (400 mg, 88% yield) as yellow oil. LC/MS (ESI) m/z: 389 (M+H)$^+$.

Step 4: 2-(3-(benzylthio)-5-(hydroxymethyl)-1H-pyrazol-1-yl)-2-cyclopropylethan-1-ol To a solution of ethyl 1-(1-cyclopropyl-2-ethoxy-2-oxoethyl)-3-iodo-1H-pyrazole-5-carboxylate (400 mg, 1.03 mmol) in THF (10 mL) was added LiAlH$_4$ (118 mg, 3.09 mmol) in portions at 0° C. under $N_2$ atmosphere and the mixture was stirred at room temperature for 1 hr. The reaction was quenched with $Na_2SO_4·10H_2O$ at 0° C. and filtered. The filtrate was concentrated to dryness to give the title compound (200 mg, 63.9% yield) as yellow solid. LC/MS (ESI) m/z: 305 (M+H)$^+$.

Step 5: 2-(benzylthio)-7-cyclopropyl-6,7-dihydro-4H-pyrazolo[5,1-c][1,4]oxazine To a solution of 2-(3-(benzylthio)-5-(hydroxymethyl)-1H-pyrazol-1-yl)-2-cyclopropylethan-1-ol (120 mg, 0.39 mmol) in THF (2 mL) was added NaH (38.6 mmol, 0.97 mmol, 60% dispersion in mineral oil) at 0° C. under $N_2$ atmosphere and the mixture was stirred at room temperature for 0.5 hr. The mixture was cooled to 0° C. and 1-(p-toluenesulfonyl)imidazole (88 mg, 0.39 mmol) was added. After being stirred at room temperature for 1 hr, the mixture was quenched with ice-water and extracted with EtOAc (2×10 mL). The combined organic layers were washed with water and brine, dried over $Na_2SO_4$, filtered and concentrated to dryness. The residue was purified by flash chromatography (silica gel, 0-10% of EtOAc in PE) to give the title compound (70 mg, 62% yield) as yellow oil. LC/MS (ESI) m/z: 287 (M+H)$^+$.

Step 6: 7-cyclopropyl-6,7-dihydro-4H-pyrazolo[5,1-c][1,4]oxazine-2-sulfonamide To a solution of 7-cyclopropyl-2-(phenylthio)-6,7-dihydro-4H-pyrazolo[5,1-c][1,4]oxazine (80 mg, 0.28 mmol) in AcOH (5 mL) and $H_2O$ (2 mL) was added NCS (135 mg, 1.0 mmol) at 0° C. and the mixture was stirred at 0° C. for 1 hr. The mixture was diluted with DCM, washed with water and brine, dried over anhydrous $Na_2SO_4$ and filtered. The filtrate was added to $NH_3$/THF solution (10 mL, 1M) at 0° C. and the resulting mixture was stirred 0° C. for 0.5 hr. The mixture was concentrated to dryness and the residue was purified by flash chromatography (silica gel, 0-50% of EtOAc in PE) to give the title compound (45 mg, 66.3% yield) as colorless oil. LC/MS (ESI) m/z: 244 (M+H)$^+$.

Intermediate A9: 1-cyclopropyl-2,3-dihydro-1H-pyrido[2,3-b][1,4]oxazine-7-sulfonamide

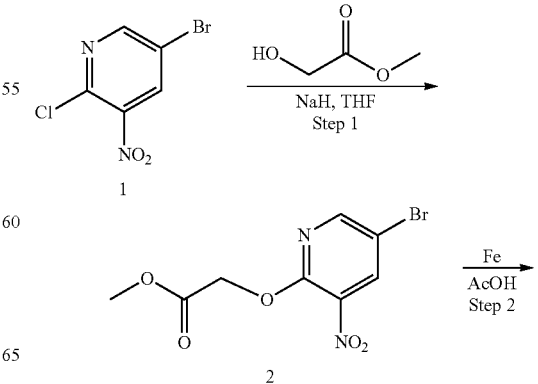

-continued

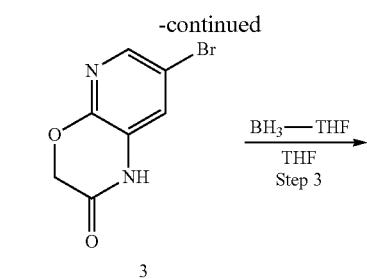

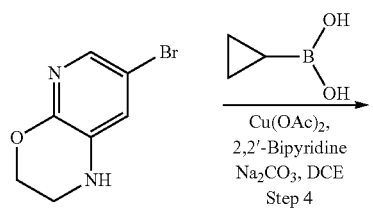

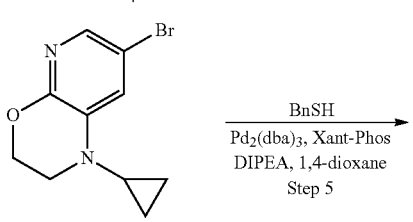

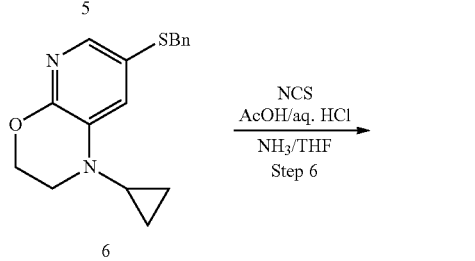

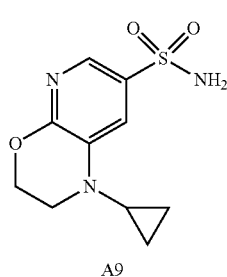

Step 1: methyl 2-((5-bromo-3-nitropyridin-2-yl)oxy)acetate

To a solution of 5-bromo-2-chloro-3-nitropyridine (10 g, 40.00 mmol) and methyl 2-hydroxyacetate (3.4 mL, 44.40 mmol) in dry THF (100 mL) was added NaH (1.76 g, 44.4 mmol, 60% dispersion in mineral oil) in portions at 0° C. and the mixture was stirred at r.t. for 1 hr. The reaction mixture was poured into ice-water and extracted with EtOAc (2×50 mL). The combined organic layers were washed with brine, dried over $Na_2SO_4$, filtered and concentrated to dryness. The residue was purified by flash chromatography (silica gel, 0-30% EtOAc in PE) to give the title compound (10 g, 90.3% yield) as light yellow solid. LC/MS (ESI) (m/z): 291/293(M+H)$^+$.

Step 2: 7-bromo-1H-pyrido[2,3-b][1,4]oxazin-2(3H)-one

To a solution of methyl 2-((5-bromo-3-nitropyridin-2-yl) oxy)acetate (10 g, 34.8 mmol) in AcOH (100 mL) was added Fe (9.75 g, 174.1 mmol) and the mixture was stirred at 80° C. for 1 hr. The mixture was filtered by diatomite and the filtrate was poured into water, extracted with EtOAc (3×50 mL). The combined organic layers were washed with brine, dried over anhydrous $Na_2SO_4$, filtered and concentrated under reduced pressure to dryness. The residue was purified by flash chromatography (silica gel, 0-25% EtOAc in PE) to give the title compound (4.7 g, 52.3% yield) as red solid. LC/MS (ESI) (m/z): 229/231 (M+H)$^+$.

Step 3: 7-bromo-2,3-dihydro-1H-pyrido[2,3-b][1,4]oxazine

To a solution of 7-bromo-1H-pyrido[2,3-b][1,4]oxazin-2(3H)-one (4 g, 17.5 mmol) in THF (40 mL) was added $BH_3$-THF complex (90 mL, 90 mmol, 1M in THF) and the mixture was stirred at 70° C. for 1 hr. The reaction was quenched with MeOH at 0° C. and the mixture was concentrated to dryness. The residue was dissolved in EtOH (20 mL) and 6 N aq·HCl (5 mL) and the mixture was stirred at 80° C. for 2 hrs. The mixture was basified with 1N aq·NaOH solution and extracted with EtOAc (3×20 mL). The combined organic layers were washed with brine, dried over $Na_2SO_4$, filtered and concentrated to dryness. The residue was purified by flash chromatography (silica gel, 0-50% EtOAc in PE) to give the title compound (1.4 g, 32.2% yield) as yellow solid. LC/MS (ESI) (m/z): 215/217 (M+H)$^+$.

Step 4: 7-bromo-1-cyclopropyl-2,3-dihydro-1H-pyrido[2,3-b][1,4]oxazine

To a mixture of 7-bromo-2,3-dihydro-1H-pyrido[2,3-b][1,4]oxazine (1.4 g, 5.76 mmol) and cyclopropylboronic acid (1.4 g, 11.52 mmol) in DCE (20 mL) was added $Cu(OAc)_2$ (1.12 g, 5.76 mmol), 2,2'-Bipyridine (1.92 g, 11.5 mmol) and $Na_2CO_3$ (1.30 g, 11.5 mmol) and the mixture was stirred at 70° C. under O2 atmosphere for 16 hrs. The mixture was filtered and the filtrate was diluted with DCM, washed with water and brine, dried over $Na_2SO_4$, filtered and concentrated to dryness. The residue was purified by flash chromatography (silica gel, 0-18% EtOAc in PE) to give the title compound (1.2 g, 52.3% yield) as white solid. LC/MS (ESI) (m/z): 255 (M+H)$^+$.

Step 5: 7-(benzylthio)-1-cyclopropyl-2,3-dihydro-1H-pyrido[2,3-b][1,4]oxazine To a mixture of 7-bromo-1-cyclopropyl-2,3-dihydro-1H-pyrido[2,3-b][1,4]oxazine (500 mg, 1.96 mmol) and phenylmethanethiol (0.25 mL, 2.16 mmol) in 1,4-dioxane (5. mL) was added DIPEA (556 mg, 2.20 mmol), Xant-Phos (56 mg, 0.098 mmol) and $Pd_2(dba)_3$ (45 mg, 0.049 mmol) under $N_2$ atmosphere, the mixture was degassed under $N_2$ atmosphere for three times and stirred at 120° C. for 16 hrs. The mixture was diluted with EtOAc, washed with water and brine, dried over anhydrous $Na_2SO_4$, filtered and concentrated under reduced pressure to dryness. The residue was purified by chromatography (silica gel, 0-17% EtOAc in PE) to give the title compound (580 mg, 93.2% yield) as yellow solid. LC/MS (ESI) (m/z): 299 (M+H)$^+$.

Step 6: 1-cyclopropyl-2,3-dihydro-1H-pyrido[2,3-b][1,4]oxazine-7-sulfonamide To a solution of 1-cyclopropyl-7-(phenylthio)-2,3-dihydro-1H-pyrido[2,3-b][1,4]oxazine (80 mg, 0.27 mmol) in AcOH (6 mL) and water (1.5 mL) was added NCS (107 mg, 0.8 mmol) and 1.0 N aq·HCl (2.0 mL) at 0° C. and the mixture was stirred at r.t. for 1 hr. The mixture was poured into water and extracted with DCM (2×5 mL). The combined organic layers were washed with brine, dried over anhydrous $Na_2SO_4$ and filtered. The filtrate was added to $NH_3$/THF solution (5 mL, 1M) at −50° C. and the resulting mixture was stirred at −50° C. for 30 mins. The mixture was concentrated to dryness and the residue was purified by flash chromatography (silica gel, 0-50% EtOAc in PE) to give the title compound (35 mg, 50.7% yield) as white solid. $^1$H NMR (400 MHz, DMSO-$d_6$) δ 7.88 (d, J=2.0 Hz, 1H), 7.65 (d, J=2.0 Hz, 1H), 4.39-4.34 (m, 2H), 3.03-2.97 (m, 1H), 2.38-2.34 (m, 1H), 2.28-2.24 (m, 1H), 0.70-0.68 (m, 2H), 0.63-0.57 (m, 2H). LC/MS (ESI) (m/z): 256 (M+H)$^+$.

Intermediate A10: (S)-6-methoxy-6,7-dihydro-5H-pyrazolo[5,1-b][1,3]oxazine-3-sulfonamide

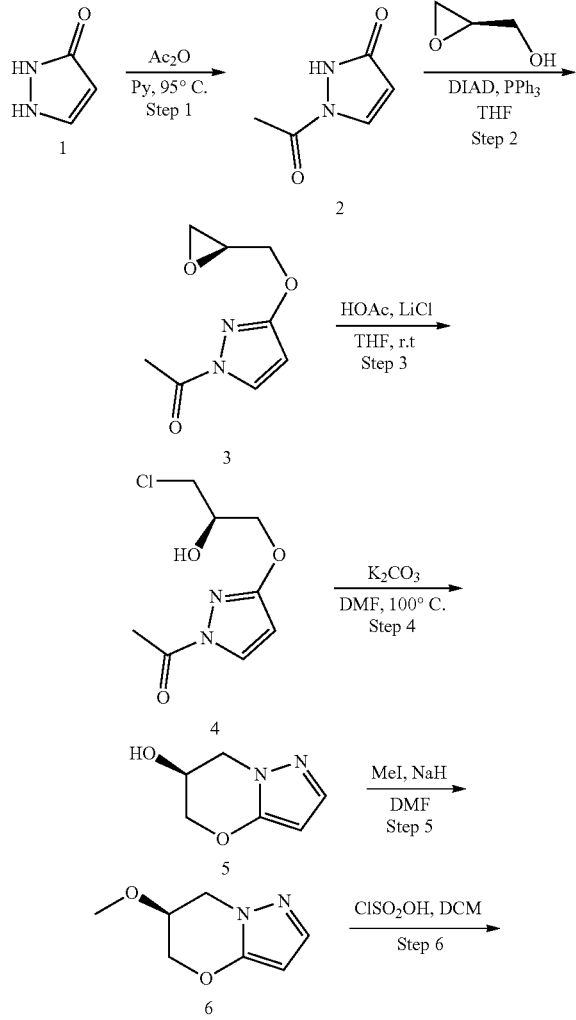

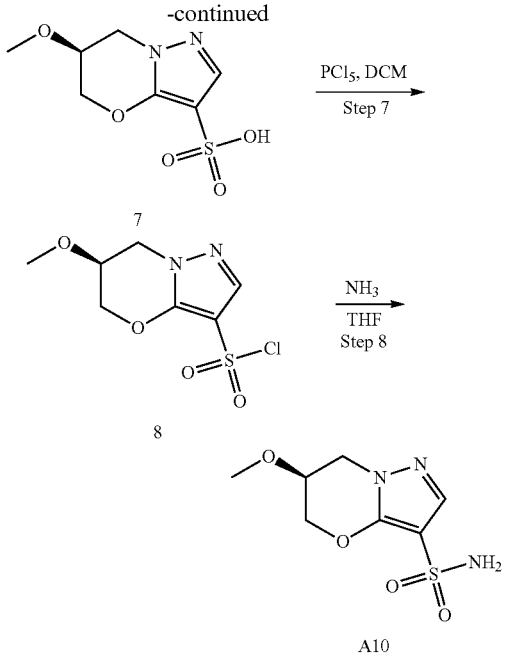

Step 1: 1-acetyl-1,2-dihydro-pyrazol-3-one

To a solution of 1,2-dihydro-pyrazol-3-one (5.0 g, 60 mmol) in pyridine (30 mL) was added acetic anhydride (6.12 g, 60 mmol) drop-wisely at 95° C. and the mixture was stirred at 95° C. for 1 hr. The mixture was concentrated to dryness and the residue was triturated with MeOH at 0° C. The slurry was filtered and the filter cake was dried under vacuum to give the title compound (5.4 g, 71% yield) as white solid. LC/MS (ESI) (m/z): 127 (M+H)$^+$.

Step 2: 1-(3-{[(2S)-oxiran-2-yl]methoxy}-1H-pyrazol-1-yl)ethan-1-one

To a mixture of 1-acetyl-2,3-dihydro-1H-pyrazol-3-one (5 g, 39.6 mmol) and PPh$_3$ (15.6 g, 59.4 mmol) in THF (400 mL) was added DIAD (11.8 mL, 59.4 mmol) drop-wisely at 0° C. under N$_2$ atmosphere and the mixture was stirred at 0° C. for 1 hr. [(2R)-oxiran-2-yl]methanol (3.16 mL, 47.6 mmol) was added to the mixture drop-wisely at 0° C. and the resulting mixture was stirred at r.t. for 16 hrs. The reaction mixture was concentrated to dryness and the residue was purified by flash chromatography (silica gel, 0-50% EtOAc in PE) to give the title compound (3.1 g, 42.9% yield) as white solid. LC/MS (ESI) (m/z): 183 (M+H)$^+$.

Step 3: 1-{3-[(2R)-3-chloro-2-hydroxypropoxy]-1H-pyrazol-1-yl}ethan-1-one

To a solution of 1-(3-{[(2S)-oxiran-2-yl]methoxy}-1H-pyrazol-1-yl)ethan-1-one (5 g, 27.4 mmol) in THF (100 mL) was added AcOH (4.71 mL, 82.3 mmol) and LiCl (3.49 mg, 82 mmol) and the mixture was stirred at r.t. for 16 hrs. The mixture was diluted with EtOAc, washed with saturated aq·NaHCO$_3$ solution and brine, dried over anhydrous Na$_2$SO$_4$, filtered and concentrated to dryness to give the title compound (6 g, 99% yield) as yellow oil, which was directly used in the next reaction without purification. LC/MS (ESI) (m/z): 219 (M+H)$^+$.

Step 4: (6S)-5H,6H,7H-pyrazolo[3,2-b][1,3]oxazin-6-ol

To a solution of 1-{3-[(2R)-3-chloro-2-hydroxypropoxy]-1H-pyrazol-1-yl}ethan-1-one (6 g, 27.4 mmol) in DMF (3 mL) was added K₂CO₃ (11.4 g, 82.3 mmol) and the mixture was stirred at 100° C. for 3 hrs. The mixture was diluted with EtOAc, washed with water and brine, dried over anhydrous Na₂SO₄, filtered and concentrated to dryness. The residue was purified by flash chromatography (silica gel, 0-10% DCM in MeOH) to give the title compound (3 g, 78% yield) as white solid. LC/MS (ESI) (m/z): 141 (M+H)⁺.

Step 5: (6S)-6-methoxy-5H,6H,7H-pyrazolo[3,2-b][1,3]oxazine

To a solution of (6S)-5H,6H,7H-pyrazolo[3,2-b][1,3]oxazin-6-ol (3 g, 21.4 mmol) in DMF (30 mL) was added NaH (1.28 g, 32.1 mmol, 60% dispersion in mineral oil) in portions at 0° C. and the mixture was stirred at 0° C. for 0.5 hr. MeI (1.99 mL, 32.1 mmol) was added and the resulting mixture was stirred at 25° C. for 4 hrs. The mixture was quenched with ice-water and extracted with EtOAc (2×10 mL). The combined organic layers were washed with saturated aq·NH₄Cl solution and brine, dried over anhydrous Na₂SO₄, filtered and concentrated to dryness. The residue was purified by flash chromatography (silica gel, 0-5% DCM in MeOH) to give the title compound (2.9 g, 87.9% yield) as white solid. LC/MS (ESI) (m/z): 155 (M+H)⁺.

Step 6: (6S)-6-methoxy-5H,6H,7H-pyrazolo[3,2-b][1,3]oxazine-3-sulfonic acid

To a solution of (6s)-6-methoxy-5H,6H,7H-pyrazolo[3,2-b][1,3]oxazine (2 g, 12.9 mmol) in DCM (20 mL) was added chlorosulfonic acid (2.59 mL, 38.9 mmol) and the mixture was stirred at room temperature for 16 hrs. The mixture was concentrated to dryness to give the title compound (3 g, 98% yield) as yellow oil, which was directly used in the next reaction without purification. LC/MS (ESI) (m/z): 235 (M+H)⁺.

Step 7: (6S)-6-methoxy-5H,6H,7H-pyrazolo[3,2-b][1,3]oxazine-3-sulfonyl chloride To a solution of (6S)-6-methoxy-5H,6H,7H-pyrazolo[3,2-b][1,3]oxazine-3-sulfonic acid (3 g, 12.8 mmol) in DCM (30 mL) was added PCl₅ (8.0 g, 38.4 mmol) and the mixture was stirred at room temperature for 4 hrs. The mixture was poured into ice-water and extracted with EtOAc (3×30 mL). The combined organic layers were washed with saturated aq·NaHCO₃ solution and brine, dried over anhydrous Na₂SO₄, filtered and concentrated to dryness. The residue was purified by flash chromatography (silica gel, 0-10% EtOAc in PE) to give the title compound (3 g, 92% yield) as white solid. LC/MS (ESI) (m/z): 253 (M+H)⁺.

Step 8: (6S)-6-methoxy-5H,6H,7H-pyrazolo[3,2-b][1,3]oxazine-3-sulfonamide

To a solution of (6S)-6-methoxy-5H,6H,7H-pyrazolo[3,2-b][1,3]oxazine-3-sulfonyl chloride (1 g, 3.95 mmol) in DCM (16 mL) was added NH₃/THF (10 mL, 1M) dropwisely at 0° C. and the mixture was stirred at r.t. for 1 hr. The mixture was filtered and the filtrate was concentrated to dryness. The residue was purified by flash chromatography (silica gel, 0-50% EtOAc in PE) to give the title compound (560 mg, 60.8% yield) as yellow solid. ¹H NMR (400 MHz, DMSO-d₆) δ 7.49 (s, 1H), 4.59 (d, J=11.9 Hz, 1H), 4.32 (d, J=11.9 Hz, 1H), 4.28-4.22 (m, 1H), 4.20-4.16 (m, 1H), 4.06-4.01 (m, 1H), 3.35 (s, 3H). LC/MS (ESI) (m/z): 234 (M+H)⁺.

Intermediate B1: 5-(imidazo[1,2-a]pyridin-7-yl)-2,3-dihydro-1H-inden-4-amine

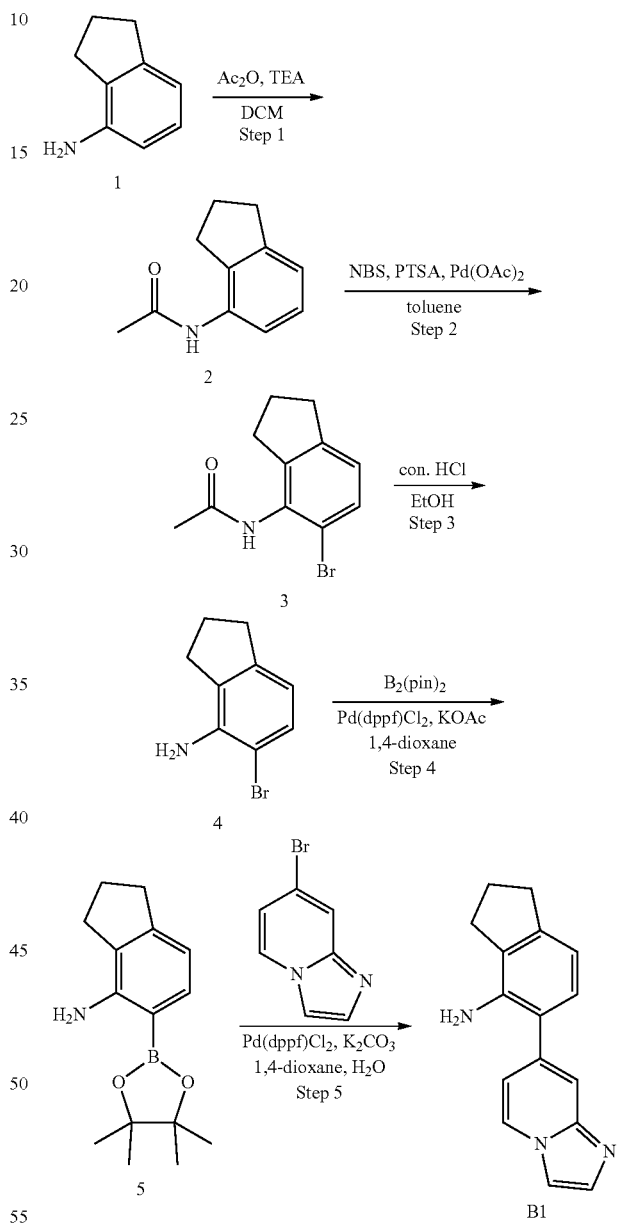

Step 1: N-(2,3-dihydro-1H-inden-4-yl)acetamide

To a mixture of 2,3-dihydro-1H-inden-4-amine (1.0 g, 7.52 mmol) and TEA (1.25 mL, 9.02 mmol) in DCM (15 mL) was added dropwise Ac₂O (767 mg, 7.52 mmol) at 0° C. and the mixture was stirred at r.t. for 2 hrs. The mixture was poured into water and extracted with DCM (2×10 mL). The combined organic layers were washed with brine, dried over anhydrous Na₂SO₄, filtered and concentrated to dryness to give the title compound (1.1 g, 91.8% yield) as white solid. LC/MS (ESI) m/z: 176 (M+H)+.

Step 2: N-(5-bromo-2,3-dihydro-1H-inden-4-yl)acetamide

A mixture of N-(2,3-dihydro-1H-inden-4-yl)acetamide (780 mg, 4.50 mmol), PTSA (460 mg, 2.44 mmol) and Pd(OAc)₂ (38 mg, 0.17 mmol) in toluene (10 mL) was stirred at room temperature for 0.5 hr under air. NBS (670 mg, 3.77 mmol) was added and the mixture was stirred at room temperature for 2 hrs. The mixture was poured into water and extracted with EtOAc (2×10 mL). The combined organic layers were washed with brine, dried over anhydrous Na₂SO₄, filtered and concentrated to dryness. The residue was purified by flash chromatography (silica gel, 0-30% EtOAc in PE) to give the title compound (700 mg, 61.9% yield) as white solid. LC/MS (ESI) m/z: 255 (M+H)+.

Step 3: 5-bromo-2,3-dihydro-1H-inden-4-amine

A mixture of N-(5-bromo-2,3-dihydro-1H-inden-4-yl)acetamide (650 mg, 2.56 mmol) in EtOH (10 mL) and con·HCl (15 mL, 36 wt % in water) was stirred at 80° C. for 16 hrs. The mixture was concentrated to dryness. The mixture was diluted with water and basified with saturated aq·NaHCO₃ solution to pH-8. The mixture was extracted with EtOAc (3×10 mL) and the combined organic layers were dried over Na₂SO₄, filtered and concentrated to dryness. The residue was purified by flash chromatography (silica gel, 0-16% EtOAc in PE) to give the title compound (300 mg, 55.3% yield) as grey solid. LC/MS (ESI) m/z: 212 (M+H)+.

Step 4: 5-(4,4,5,5-tetramethyl-1,3,2-dioxaborolan-2-yl)-2,3-dihydro-1H-inden-4-amine To a mixture of 5-bromo-2,3-dihydro-1H-inden-4-amine (500 mg, 2.36 mmol) and 4,4,4',4',5,5,5',5'-octamethyl-2,2'-bi(1,3,2-dioxaborolane) (780 mg, 3.07 mmol) in 1,4-dioxane (8 mL) were added KOAc (463 mg, 4.72 mmol) and Pd(dppf)Cl₂ (173 mg, 0.24 mmol) under N₂ atmosphere. The mixture was degassed under N₂ atmosphere for three times and stirred at 100° C. for 3 hrs. The mixture was diluted with EtOAc, washed with saturated aq·NH₄Cl solution and brine, dried over anhydrous Na₂SO₄, filtered and concentrated to dryness. The residue was purified by flash chromatography (silica gel, 0-5% EtOAc in PE) to give the title compound (200 mg, 32.7% yield) as yellow solid. LC/MS (ESI) (m/z): 260 (M+H)+.

Step 5: 5-(imidazo[1,2-a]pyridin-7-yl)-2,3-dihydro-1H-inden-4-amine

To a mixture of 7-bromoimidazo[1,2-a]pyridine (190 mg, 0.96 mmol) and 5-(4,4,5,5-tetramethyl-1,3,2-dioxaborolan-2-yl)-2,3-dihydro-1H-inden-4-amine (250 mg, 0.96 mmol) in 1,4-dioxane (5 mL) and H₂O (1 mL) were added K₂CO₃ (333 mg, 2.41 mmol) followed by Pd(dppf)Cl₂ (71 mg, 0.09 mmol) under N₂ atmosphere. The mixture was degassed under N₂ atmosphere for three times and stirred at 100° C. for 2 hrs. The mixture was diluted with EtOAc (20 mL), washed with water and brine, dried over Na₂SO₄, filtered and concentrated to dryness. The residue was purified by flash chromatography (silica gel, 0-5% MeOH in DCM) to give the title compound (150 mg, 62.4% yield) as yellow solid. ¹H NMR (400 MHz, CDCl₃) δ 8.16 (d, J=6.9 Hz, 1H), 7.71 (s, 1H), 7.65 (s, 1H), 7.59 (s, 1H), 7.02 (d, J=7.6 Hz, 1H), 6.95 (d, J=6.6 Hz, 1H), 6.77 (d, J=7.6 Hz, 1H), 2.96 (t, J=7.5 Hz, 2H), 2.77 (t, J=7.3 Hz, 2H), 2.23-2.11 (m, 2H). LC/MS (ESI) (m/z): 250 (M+H)+.

Intermediate B7: 6-methyl-5-(pyrazolo[1,5-a]pyridin-5-yl)-2,3-dihydro-1H-inden-4-amine

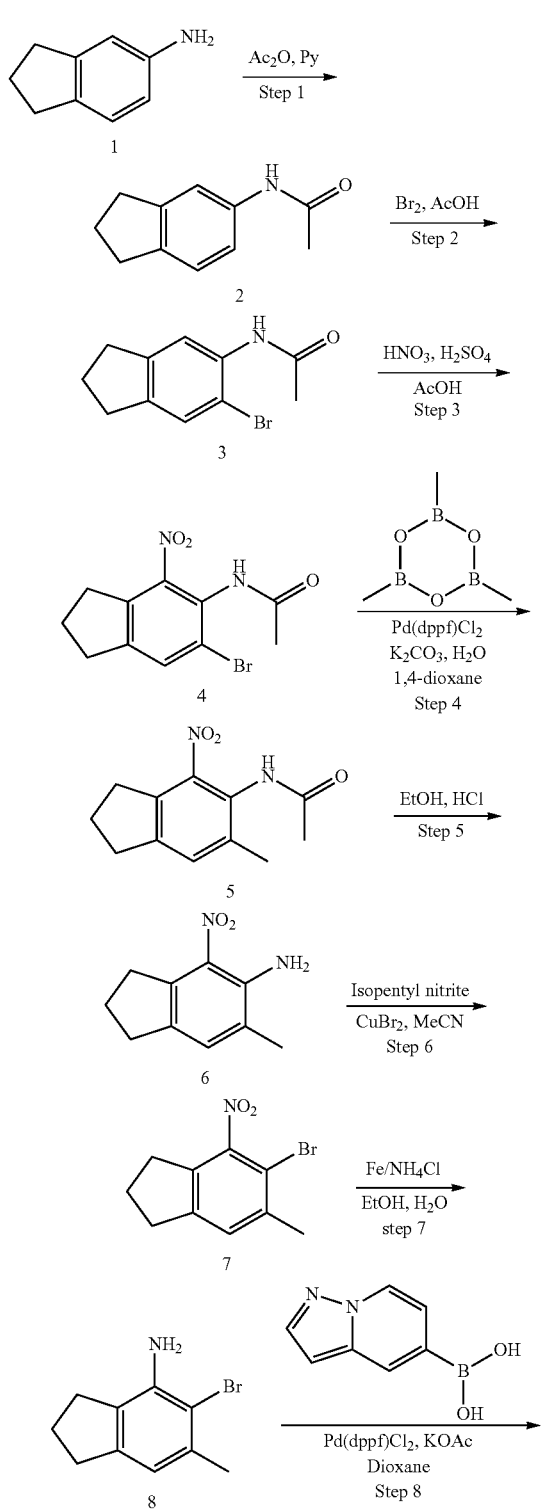

-continued

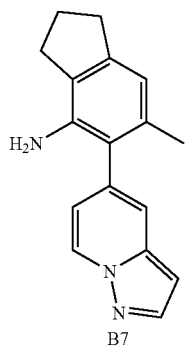

B7

Step 1: N-(2,3-dihydro-1H-inden-5-yl)acetamide

To a mixture of 2,3-dihydro-1H-inden-5-amine (5 g, 37.5 mmol) and pyridine (4.86 mL, 60.1 mmol) in DCM (50 mL) was added acetic anhydride (3.88 mL, 41.3 mmol) drop-wisely at 0° C. and the mixture was stirred at 0° C. for 1 hr. The mixture was quenched with water and extracted with DCM (3×30 mL). The combined organic layers were washed with brine, dried over anhydrous $Na_2SO_4$, filtered and concentrated to dryness to give the title compound (5.9 g, 89.7% yield) as yellow solid. $^1$H NMR (400 MHz, $CDCl_3$) δ 7.44 (s, 1H), 7.14 (s, 2H), 2.91-2.84 (m, 4H), 2.16 (s, 3H), 2.10-2.02 (m, 2H). LC/MS (ESI) (m/z): 176 $(M+H)^+$.

Step 2: N-(6-bromo-2,3-dihydro-1H-inden-5-yl)acetamide

To a solution of N-(2,3-dihydro-1H-inden-5-yl)acetamide (5.9 g, 33.7 mmol) in AcOH (90 mL) was added $Br_2$ (2.08 mL, 40.4 mmol) drop-wisely over a period of 1 hr at 10° C. After being stirred at 10° C. for additional 10 min, the mixture was poured into ice-water and extracted with DCM (2×50 mL). The combined organic layers were washed with brine, saturated aq·$NaHCO_3$ solution and saturated aq·$NaHSO_3$ solution successively, dried over $Na_2SO_4$, filtered and concentrated to dryness to give the title compound (7 g, 81.8% yield) as white solid. 1H NMR (400 MHz, $CDCl_3$) δ 7.44 (s, 1H), 7.14 (s, 2H), 2.91-2.84 (m, 4H), 2.16 (s, 3H), 2.10-2.02 (m, 2H). LC/MS (ESI) (m/z): 254 $(M+H)^+$.

Step 3: N-(6-bromo-4-nitro-2,3-dihydro-1H-inden-5-yl)acetamide

To a stirred solution of N-(6-bromo-2,3-dihydro-1H-inden-5-yl)acetamide (7 g, 27.6 mmol) in AcOH (40 mL) and sulfuric acid (20 mL) was added a precooled mixture of sulfuric acid (20 mL) and nitric acid (24.8 mL, 275.5 mmol) drop-wisely below 20° C. for 1 hr and the resulting mixture was stirred at r.t. for another 1 hr. The mixture was poured into ice-water and stirred at 0° C. for 2 hrs. The mixture was filtered and the filter cake was washed with water, dried over $Na_2SO_4$, filtered and concentrated to dryness to give the title compound (7.3 g, 88.6% yield) as brown solid. $^1$H NMR (400 MHz, $CDCl_3$) δ 7.65 (s, 1H), 7.34 (s, 1H), 3.11-3.07 (t, J=7.5 Hz, 2H), 3.01-2.97 (t, J=7.6 Hz, 2H), 2.20 (s, 3H), 2.19-2.11 (m, 2H). LC/MS (ESI) (m/z): 299 $(M+H)^+$.

Step 4: N-(6-methyl-4-nitro-2,3-dihydro-1H-inden-5-yl)acetamide

To a mixture of N-(6-bromo-4-nitro-2,3-dihydro-1H-inden-5-yl)acetamide (7 g, 23.4 mmol), trimethyl-1,3,5,2,4,6-trioxatriborinane (11.7 mL, 46.8 mmol) and $K_2CO_3$ (34.7 g, 251 mmol) in 1,4-dioxane (70 mL) and $H_2O$ (15 mL) was added Pd(dppf)$Cl_2$ (1.71 g, 2.34 mmol) under $N_2$ atmosphere, the mixture was degassed under $N_2$ atmosphere for three times and stirred at 100° C. for 16 hrs. The mixture was diluted with EtOAc, washed with water and brine, dried over anhydrous $Na_2SO_4$, filtered and concentrated to dryness. The residue was purified by flash chromatography (0-20% EtOAc in PE) to give the title compound (2.9 g, 52.9% yield) as yellow solid. $^1$H NMR (400 MHz, $CDCl_3$) δ 7.74 (s, 1H), 7.31 (s, 1H), 3.11-3.07 (t, J=7.5 Hz, 2H), 2.96-2.93 (t, J=7.5 Hz, 2H), 2.27 (s, 3H), 2.19 (s, 3H), 2.16-2.08 (m, 2H). LC/MS (ESI) (m/z): 235 $(M+H)^+$.

Step 5: 6-methyl-4-nitro-2,3-dihydro-1H-inden-5-amine

To a solution of N-(6-methyl-4-nitro-2,3-dihydro-1H-inden-5-yl)acetamide (2.9 g, 12.4 mmol) in EtOH (60 mL) was added conc·HCl (60 mL) and the mixture was stirred at 80° C. overnight. The mixture was concentrated to dryness and the residue was neutralized with 2 M aq·NaOH solution. The mixture was extracted with DCM (2×20 mL) and the combined organic layers were washed with water and brine, dried over anhydrous $Na_2SO_4$, filtered and concentrated to dryness to give the title compound (2.1 g, 88.3% yield) as yellow solid. $^1$H NMR (400 MHz, $CDCl_3$) δ 7.15 (s, 1H), 5.81 (s, 2H), 3.32-3.28 (t, J=7.5 Hz, 2H), 2.84-2.81 (t, J=7.6 Hz, 2H), 2.20 (s, 3H), 2.09-2.01 (m, 2H). LC/MS (ESI) (m/z): 193 $(M+H)^+$.

Step 6: 5-bromo-6-methyl-4-nitro-2,3-dihydro-1H-indene

A mixture of 6-methyl-4-nitro-2,3-dihydro-1H-inden-5-amine (2.1 g, 10.9 mmol) and isopentyl nitrite (1.41 g, 12.0 mmol) in $CH_3CN$ (30 mL) was heated to 55° C. and $CuBr_2$ (2.44 g, 10.9 mmol) was added under $N_2$ atmosphere and the mixture was stirred at 70° C. for 1 hr. The reaction mixture was cooled to r.t. and 1M aq·HCl (20 mL) was added. The reaction mixture was extracted with DCM (3×20 mL) and the combined organic layers were washed with brine, dried over $Na_2SO_4$, filtered and concentrated to dryness. The residue was purified by flash chromatography (silica gel, 0-10% EtOAc in PE) to give the title compound (1.7 g, 60.8% yield) as yellow solid. $^1$H NMR (400 MHz, DMSO-$d_6$): δ 7.49 (s, 1H), 2.93-2.87 (m, 4H), 2.40 (s, 3H), 2.12-2.05 (m, 2H). LC/MS (ESI) (m/z): 256 $(M+H)^+$.

Step 7: 5-bromo-6-methyl-2,3-dihydro-1H-inden-4-amine

To a solution of 5-bromo-6-methyl-4-nitro-2,3-dihydro-1H-indene (1.7 g, 6.64 mmol) in EtOH (20 mL) was added saturated aq·$NH_4Cl$ solution (4 mL) and Fe (3.7 g, 66.4 mmol) and the mixture was stirred at 80° C. for 2 hrs. After cooling to room temperature, the reaction was diluted with EtOAc (30 mL) and filtered through a pad of Celite. The filtrate was washed with water and brine, dried over anhydrous $MgSO_4$, filtered and concentrated to dryness. The residue was purified by flash chromatography (silica gel, 0-10% EtOAc in PE) to give the title compound (1.4 g, 93.3% yield) as pink solid. $^1$H NMR (400 MHz, DMSO-$d_6$) δ 6.47 (s, 1H), 4.94 (s, 2H), 2.75-2.71 (t, J=7.5 Hz, 2H), 2.70-2.66 (t, J=7.3 Hz, 2H), 2.23 (s, 3H), 2.02-1.93 (m, 2H). LC/MS (ESI) (m/z): 226 $(M+H)^+$.

Step 8: 6-methyl-5-(pyrazolo[1,5-a]pyridin-5-yl)-2,3-dihydro-1H-inden-4-amine

To a mixture of pyrazolo[1,5-a]pyridin-5-ylboronic acid (100 mg, 0.6 mmol) and 5-bromo-6-methyl-2,3-dihydro-1H-inden-4-amine (150 mg, 0.6 mmol) in 1,4-dioxane (10 mL) and water (2 mL) was added $K_2CO_3$ (260 mg, 1.9 mmol) followed by Pd(dppf)Cl$_2$ (50 mg, 0.07 mmol) under $N_2$ atmosphere. The mixture was degassed under $N_2$ atmosphere for three times and stirred at 90° C. for 16 hrs. After cooling, the reaction was diluted with EtOAc and filtered through a pad of Celite. The filtrate was washed with water and brine, dried over anhydrous $Na_2SO_4$, filtered and concentrated to dryness. The residue was purified by flash chromatography (silica gel, 0-40% EtOAc in PE) to give the title compound (110 mg, 67.7% yield) as white solid. $^1$H NMR (400 MHz, CDCl$_3$) δ 8.55 (d, J=7.1 Hz, 1H), 7.99 (d, J=2.2 Hz, 1H), 7.44 (s, 1H), 6.74-6.62 (m, 2H), 6.53 (d, J=1.9 Hz, 1H), 2.94 (t, J=7.5 Hz, 2H), 2.74 (t, J=7.3 Hz, 2H), 2.18-2.11 (m, 2H), 2.06 (s, 3H). LC/MS (ESI) (m/z): 264 (M+H)$^+$.

The intermediates in the following Table 1 were prepared by using a method and starting materials analogous to that used to prepare the intermediates as described herein.

TABLE 1

| intermediate | Analytical data | method |
|---|---|---|
| Intermediate B2 | $^1$H NMR (400 MHz, CDCl$_3$) δ 8.67 (s, 1H), 8.37 (s, 1H), 7.81 (d, J = 9.0 Hz, 1H), 7.67 (d, J = 9.2 Hz, 1H), 6.99 (d, J = 7.5 Hz, 1H), 6.79 (d, J = 7.5 Hz, 1H), 2.98 (t, J = 7.5 Hz, 2H), 2.78 (t, J = 7.3 Hz, 2H), 2.26-2.12 (m, 2H). LC/MS (ESI) m/z: 251 (M + H)$^+$. | Intermediate B1 |
| Intermediate B3 | $^1$H NMR (400 MHz, CDCl$_3$) δ 8.62 (d, J = 7.0 Hz, 1H), 8.36 (s, 1H), 7.86 (s, 1H), 7.21 (d, J = 6.9 Hz, 1H), 7.03 (d, J = 7.6 Hz, 1H), 6.80 (d, J = 7.6 Hz, 1H), 2.98 (t, J = 7.5 Hz, 2H), 2.78 (t, J = 7.3 Hz, 2H), 2.25-2.09 (m, 2H). LC/MS (ESI) (m/z): 251 (M + H)$^+$. | Intermediate B1 |
| Intermediate B4 | $^1$H NMR (400 MHz, CDCl$_3$) δ 8.50 (d, J = 7.1 Hz, 1H), 7.97 (s, 1H), 7.61 (s, 1H), 7.02 (d, J = 7.6 Hz, 1H), 6.89 (d, J = 6.4 Hz, 1H), 6.78 (d, J = 7.6 Hz, 1H), 6.52 (s, 1H), 2.97 (t, J = 7.5 Hz, 2H), 2.78 (t, J = 7.3 Hz, 2H), 2.23-2.12 (m, 2H). LC/MS (ESI) (m/z): 250 (M + H)$^+$. | Intermediate B1 |

TABLE 1-continued

| intermediate | Analytical data | method |
|---|---|---|
| 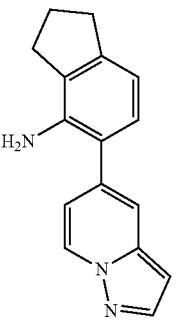

Intermediate B5 | ¹H NMR (400 MHz, DMSO-d₆) δ 8.67 (d, J = 7.2 Hz, 1H), 7.99 (d, J = 1.9 Hz, 1H), 7.62 (s, 1H), 6.92-6.84 (m, 2H), 6.60-6.58 (m, 2H), 4.66 (s, 2H), 2.83 (t, J = 7.4 Hz, 2H), 2.71 (t, J = 7.3 Hz, 2H), 2.07-1.99 (m, 2H). LC/MS (ESI) (m/z): 250 (M + H)⁺. | Intermediate B1 |
| 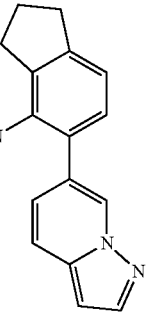

Intermediate B6 | ¹H NMR (400 MHz, CDCl₃) δ 8.55 (s, 1H), 7.97 (d, J = 1.6 Hz, 1H), 7.59 (d, J = 9.0 Hz, 1H), 7.23 (s, 1H), 7.01 (d, J = 7.6 Hz, 1H), 6.78 (d, J = 7.5 Hz, 1H), 6.55 (s, 1H), 2.97 (t, J = 7.5 Hz, 2H), 2.78 (t, J = 7.3 Hz, 2H), 2.22-2.12 (m, 2H). LC/MS (ESI) (m/z): 250 (M + H)⁺. | Intermediate B1 |
| 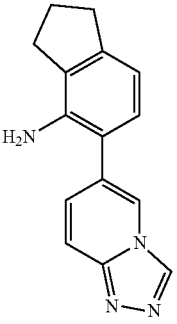

Intermediate B8 | LC/MS (ESI) (m/z): 251 (M + H)⁺. | Intermediate B1 |
| 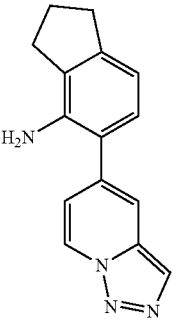

Intermediate B9 | ¹H NMR (400 MHz, CDCl₃) δ 8.77 (d, J = 7.2 Hz, 1H), 8.05 (s, 1H), 7.79 (s, 1H), 7.15 (d, J = 7.2 Hz, 1H), 7.02 (d, J = 7.6 Hz, 1H), 6.80 (d, J = 7.6 Hz, 1H), 2.98 (t, J = 7.5 Hz, 2H), 2.79 (t, J = 7.3 Hz, 2H), 2.28-2.11 (m, 2H). LC/MS (ESI) (m/z): 251 (M + H)⁺. | Intermediate B1 |

TABLE 1-continued

| intermediate | Analytical data | method |
|---|---|---|
| Intermediate B10 | $^1$H NMR (400 MHz, CDCl$_3$) δ 8.14 (s, 1H), 7.97 (s, 1H), 7.50 (d, J = 9.4 Hz, 1H), 7.46 (s, 1H), 6.99 (d, J = 7.6 Hz, 1H), 6.85 (d, J = 9.3 Hz, 1H), 6.76 (d, J = 7.5 Hz, 1H), 2.97 (t, J = 7.4 Hz, 2H), 2.77 (t, J = 7.3 Hz, 2H), 2.23-2.12 (m, 2H). LC/MS (ESI) (m/z): 250 (M + H)$^+$. | Intermediate B1 |
| Intermediate B11 | LC/MS (ESI) (m/z): 264 (M + H)$^+$. | Intermediate B7 |
| Intermediate B12 | LC/MS (ESI) (m/z): 264 (M + H)$^+$. | Intermediate B7 |
| Intermediate B13 | $^1$H NMR (400 MHz, DMSO) δ 8.32 (s, 1H), 7.92 (s, 1H), 7.58 (s, 2H), 6.96 (d, J = 9.1 Hz, 1H), 6.46 (s, 1H), 4.32 (s, 2H), 2.79 (t, J = 7.4 Hz, 2H), 2.65 (t, J = 7.2 Hz, 2H), 2.00 (d, J = 7.2 Hz, 2H), 1.92 (s, 3H). LC/MS (ESI) (m/z): 264 (M + H)$^+$. | Intermediate B7 |

TABLE 1-continued

| intermediate | Analytical data | method |
|---|---|---|
| Intermediate B14 | ¹H NMR (400 MHz, CDCl₃) δ 8.59 (d, J = 3.8 Hz, 1H), 7.62 (d, J = 3.9 Hz, 1H), 7.12 (d, J = 3.5 Hz, 1H), 6.68 (s, 1H), 6.28 (d, J = 3.9 Hz, 1H), 2.95 (t, J = 7.5 Hz, 2H), 2.74 (t, J = 7.3 Hz, 2H), 2.19-2.12 (m, 2H), 1.93 (s, 3H), 1.24 (s, 9H). LC/MS (ESI) (m/z): 364 (M + H)⁺. | Intermediate B7 |

Example 1: (R)-4-cyclopropyl-N-((5-(pyrazolo[1,5-a]pyridin-5-yl)-2,3-dihydro-1H-inden-4-yl)carbamoyl)-6,7-dihydro-4H-pyrazolo[5,1-c][1,4]oxazine-2-sulfonamide

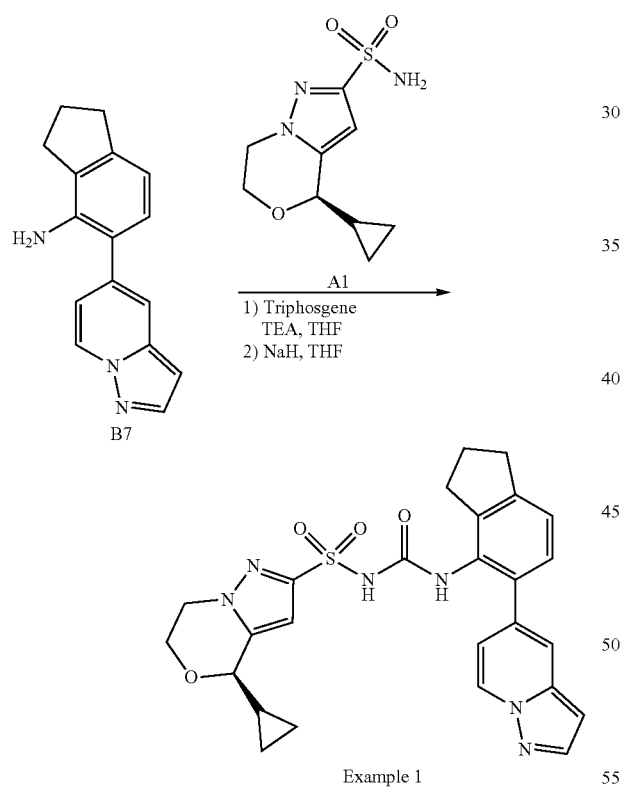

To a mixture of 5-(pyrazolo[1,5-a]pyridin-5-yl)-2,3-dihydro-1H-inden-4-amine (intermediate B5, 30 mg, 0.12 mmol) and Et₃N (36 mg, 0.36 mmol) in THF (3 mL) was added triphosgene (21 mg, 0.07 mmol) in portions under N₂ atmosphere at 0° C. After being stirred at 0° C. for 0.5 hr, the mixture was filtered and the filtrate was directly used in the next reaction. To a solution of (R)-4-cyclopropyl-6,7-dihydro-4H-pyrazolo[5,1-c][1,4]oxazine-2-sulfonamide (intermediate A1, 40 mg, 0.18 mmol) in THF (1 mL) was added NaH (22 mg, 0.54 mmol, 60% dispersion in mineral oil) in portions at 0° C., after being stirred at 0° C. for 0.5 hr, the above filtrate was added drop-wisely to the mixture. The resulting mixture was stirred at r.t. for 0.5 hr.

The mixture was poured into ice water and acidified with 1N aq·HCl to pH-4. The mixture was extracted with EtOAc (3×10 mL) and the combined organic layers were washed with brine, dried over anhydrous Na₂SO₄, filtered and concentrated to dryness. The residue was purified by prep-HPLC(C₁₈, 10~80% acetonitrile in H₂O with 0.1% ammonium bicarbonate) to give the title compound (10 mg, 10.7% yield) as white solid. ¹H NMR (400 MHz, DMSO-d₆) δ 8.56 (d, J=7.2 Hz, 1H), 8.00 (d, J=2.2 Hz, 1H), 7.79 (s, 1H), 7.58 (s, 1H), 7.18 (d, J=2.6 Hz, 2H), 6.80 (d, J=7.1 Hz, 1H), 6.59 (d, J=1.6 Hz, 1H), 6.49 (s, 1H), 4.31-4.24 (m, 1H), 4.17-4.07 (m, 2H), 3.98 (d, J=8.8 Hz, 1H), 3.95-3.87 (m, 1H), 2.92 (t, J=7.4 Hz, 2H), 2.72 (t, J=7.3 Hz, 2H), 2.05-1.90 (m, 2H), 1.16-1.06 (m, 1H), 0.70-0.63 (m, 1H), 0.61-0.64 (m, 1H), 0.52-0.42 (dt, J=8.5, 5.0 Hz, 2H). LC/MS (ESI) (m/z): 519 (M+H)⁺.

Example 2: (R)-4-cyclopropyl-N-((5-(pyrazolo[1,5-a]pyridin-6-yl)-2,3-dihydro-1H-inden-4-yl)carbamoyl)-6,7-dihydro-4H-pyrazolo[5,1-c][1,4]oxazine-2-sulfonamide

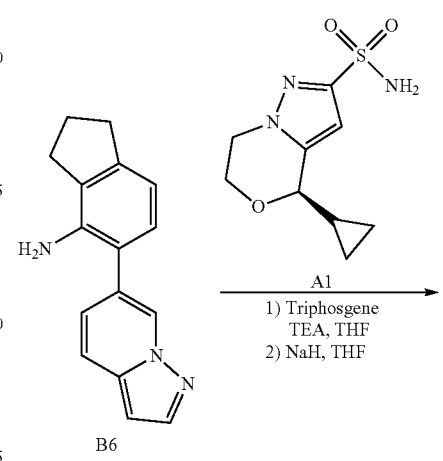

-continued

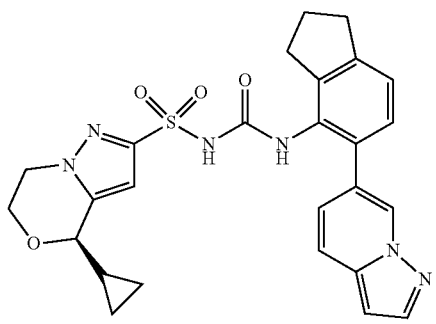

Example 2

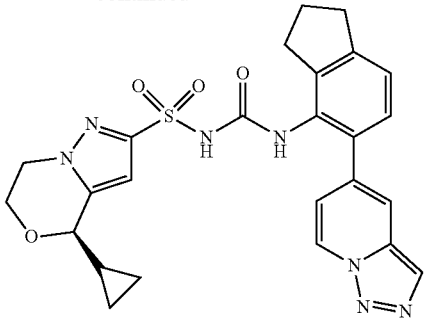

Example 3

The title compound was prepared as described for Example 1 from (R)-4-cyclopropyl-6,7-dihydro-4H-pyrazolo[5,1-c][1,4]oxazine-2-sulfonamide (intermediate A1) and 5-(pyrazolo[1,5-a]pyridin-6-yl)-2,3-dihydro-1H-inden-4-amine (intermediate B6). The residue was purified by prep.HPLC to give the title compound as white solid. $^1$H NMR (400 MHz, DMSO-$d_6$) δ 8.54 (s, 1H), 8.00 (d, J=2.2 Hz, 1H), 7.64 (d, J=9.1 Hz, 1H), 7.17 (s, 2H), 7.12 (d, J=9.1 Hz, 1H), 6.62 (d, J=1.5 Hz, 1H), 6.50 (s, 1H), 4.28 (dt, J=5.5, 3.0 Hz, 1H), 4.16-4.08 (m, 2H), 4.00 (d, J=9.0 Hz, 1H), 3.94-3.87 (m, 1H), 2.91 (t, J=7.4 Hz, 2H), 2.71 (t, J=7.3 Hz, 2H), 2.05-1.95 (m, 2H), 1.15-1.07 (m, 1H), 0.67-0.54 (m, 2H), 0.53-0.44 (m, 2H). LC/MS (ESI) m/z: 519 (M+H)$^+$.

Example 3: (R)-N-((5-([1,2,3]triazolo[1,5-a]pyridin-5-yl)-2,3-dihydro-1H-inden-4-yl)carbamoyl)-4-cyclopropyl-6,7-dihydro-4H-pyrazolo[5,1-c][1,4]oxazine-2-sulfonamide

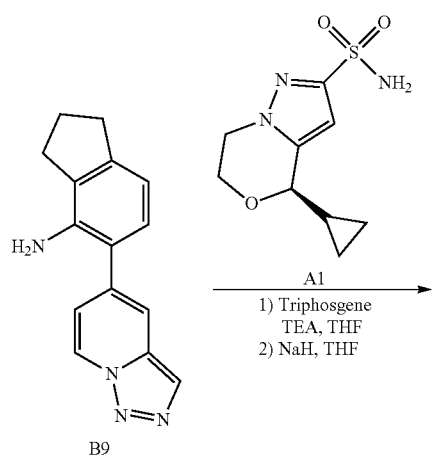

The title compound was prepared as described for Example 1 from (R)-4-cyclopropyl-6,7-dihydro-4H-pyrazolo[5,1-c][1,4]oxazine-2-sulfonamide (intermediate A1) and 5-([1,2,3]triazolo[1,5-a]pyridin-5-yl)-2,3-dihydro-1H-inden-4-amine (intermediate B9). The residue was purified by prep.HPLC to give the title compound as white solid. $^1$H NMR (400 MHz, DMSO-$d_6$) δ 8.97 (d, J=6.8 Hz, 1H), 8.17 (s, 1H), 7.83 (s, 1H), 7.21 (s, 2H), 7.08 (d, J=6.7 Hz, 1H), 6.46 (s, 1H), 4.30-4.25 (m, 1H), 4.14-4.07 (m, 2H), 3.97-3.89 (m, 2H), 2.93 (t, J=7.3 Hz, 2H), 2.74 (t, J=7.1 Hz, 2H), 2.03-1.99 (m, 2H), 1.13-1.07 (m, 1H), 0.68-0.63 (m, 1H), 0.59-0.54 (m, 1H), 0.49-0.44 (m, 2H). LC/MS (ESI) m/z: 520 (M+H)$^+$.

Example 4: (R)-N-((5-([1,2,4]triazolo[1,5-a]pyridin-6-yl)-2,3-dihydro-1H-inden-4-yl)carbamoyl)-4-cyclopropyl-6,7-dihydro-4H-pyrazolo[5,1-c][1,4]oxazine-2-sulfonamide

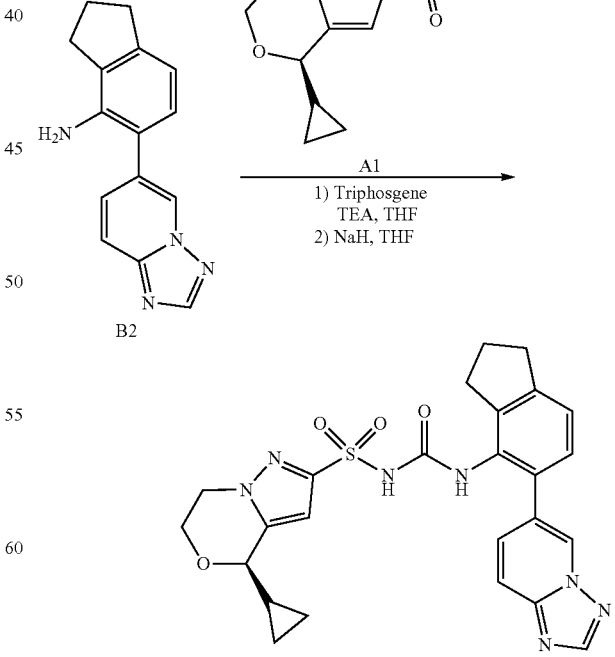

Example 4

The title compound was prepared as described for Example 1 from (R)-4-cyclopropyl-6,7-dihydro-4H-pyrazolo[5,1-c][1,4]oxazine-2-sulfonamide (intermediate A1) and 5-([1,2,4]triazolo[1,5-a]pyridin-6-yl)-2,3-dihydro-1H-inden-4-amine (intermediate B2). The residue was purified by prep.HPLC to give the title compound as white solid. $^1$H NMR (400 MHz, DMSO-$d_6$) δ 8.80 (s, 1H), 8.47 (s, 1H), 7.72 (d, J=9.2 Hz, 1H), 7.64 (d, J=9.1 Hz, 1H), 7.14 (dd, J=17.0, 7.6 Hz, 2H), 6.28 (s, 1H), 4.25 (d, J=11.5 Hz, 2H), 4.04 (s, 3H), 2.91 (t, J=7.3 Hz, 2H), 2.79 (t, J=7.2 Hz, 2H), 2.02-1.95 (m, 2H), 1.14-1.06 (m, 1H), 0.65 (s, 1H), 0.57 (d, J=8.1 Hz, 1H), 0.47 (d, J=9.2 Hz, 2H). LC/MS (ESI) m/z: 520 (M+H)$^+$.

Example 5: (S)-4-cyclopropyl-N-((5-(pyrazolo[1,5-a]pyridin-5-yl)-2,3-dihydro-1H-inden-4-yl)carbamoyl)-6,7-dihydro-4H-pyrazolo[5,1-c][1,4]oxazine-2-sulfonamide

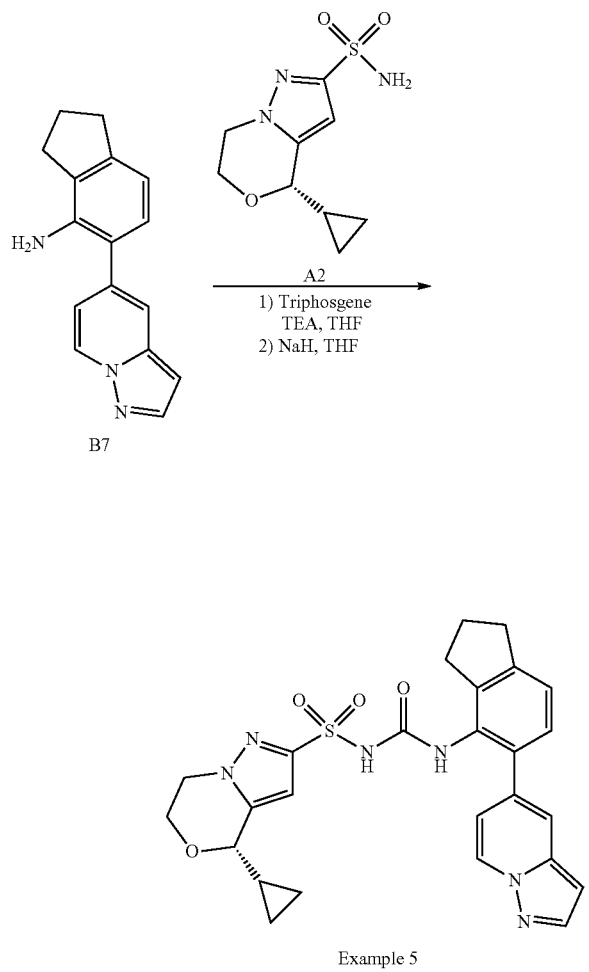

Example 5

The title compound was prepared as described for Example 1 from (S)-4-cyclopropyl-6,7-dihydro-4H-pyrazolo[5,1-c][1,4]oxazine-2-sulfonamide (intermediate A2) and 5-(pyrazolo[1,5-a]pyridin-5-yl)-2,3-dihydro-1H-inden-4-amine (intermediate B5). The residue was purified by prep.HPLC to give the title compound as white solid. $^1$H NMR (400 MHz, DMSO-$d_6$) δ 8.57 (d, J=7.2 Hz, 1H), 8.01 (d, J=2.1 Hz, 1H), 7.59 (s, 1H), 7.20-7.16 (m, 2H), 6.80 (d, J=7.4 Hz, 1H), 6.59 (d, J=1.7 Hz, 1H), 6.49 (s, 1H), 4.30-4.26 (m, 1H), 4.13-4.10 (m, 2H), 3.98 (d, J=8.9 Hz, 1H), 3.95-3.88 (m, 1H), 2.92 (t, J=7.4 Hz, 2H), 2.72 (t, J=7.3 Hz, 2H), 2.04-1.96 (m, 2H), 1.15-1.07 (m, 1H), 0.70-0.63 (m, 1H), 0.60-0.55 (m, 1H), 0.53-0.44 (m, 2H). LC/MS (ESI) m/z: 519 (M+H)$^+$.

Example 6: (S)-4-cyclopropyl-N-((5-(pyrazolo[1,5-a]pyridin-6-yl)-2,3-dihydro-1H-inden-4-yl)carbamoyl)-6,7-dihydro-4H-pyrazolo[5,1-c][1,4]oxazine-2-sulfonamide

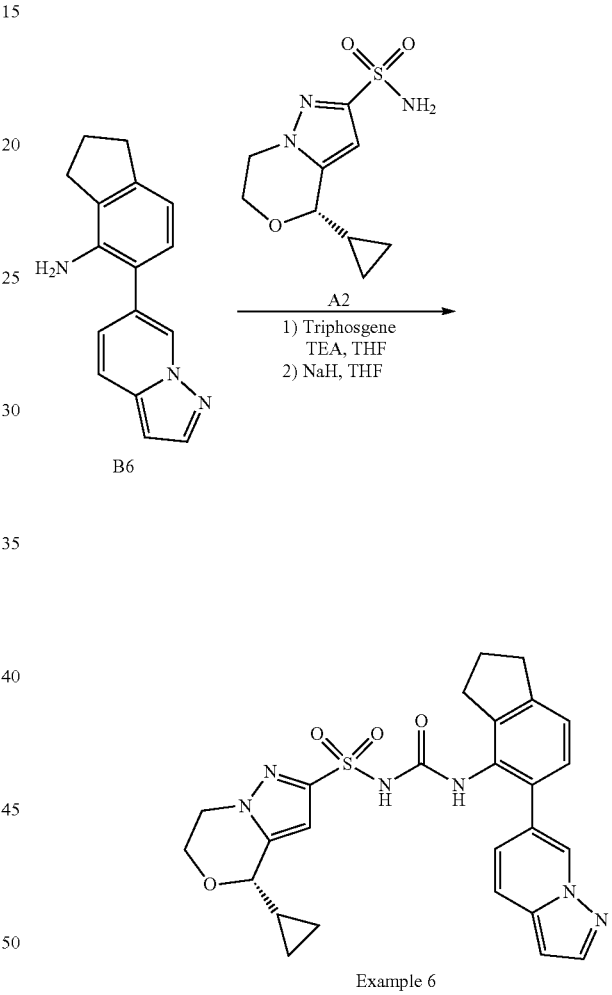

Example 6

The title compound was prepared as described for Example 1 from (S)-4-cyclopropyl-6,7-dihydro-4H-pyrazolo[5,1-c][1,4]oxazine-2-sulfonamide (intermediate A2) and 5-(pyrazolo[1,5-a]pyridin-6-yl)-2,3-dihydro-1H-inden-4-amine (intermediate B6). The residue was purified by prep.HPLC to give the title compound as white solid. $^1$H NMR (400 MHz, DMSO-$d_6$) δ 8.55 (s, 1H), 8.00 (d, J=2.1 Hz, 1H), 7.64 (d, J=9.2 Hz, 1H), 7.15 (d, J=9.9 Hz, 3H), 6.62 (s, 1H), 6.47 (s, 1H), 4.27 (d, J=12.1 Hz, 1H), 4.10 (s, 2H), 3.99 (d, J=9.1 Hz, 1H), 3.90 (dt, J=13.8, 6.7 Hz, 1H), 2.92 (t, J=7.4 Hz, 2H), 2.73 (t, J=7.2 Hz, 2H), 2.04-1.94 (m, 2H), 1.15 (t, J=7.3 Hz, 1H), 0.66 (d, J=8.0 Hz, 1H), 0.57 (d, J=4.4 Hz, 1H), 0.52-0.42 (m, 2H). LC/MS (ESI) m/z: 519 (M+H)$^+$.

Example 7: (S)-N-((5-([1,2,3]triazolo[1,5-a]pyridin-5-yl)-2,3-dihydro-1H-inden-4-yl)carbamoyl)-4-cyclopropyl-6,7-dihydro-4H-pyrazolo[5,1-c][1,4]oxazine-2-sulfonamide Example 8: (S)-N-((5-([1,2,4]triazolo[1,5-a]pyridin-6-yl)-2,3-dihydro-1H-inden-4-yl)carbamoyl)-4-cyclopropyl-6,7-dihydro-4H-pyrazolo[5,1-c][1,4]oxazine-2-sulfonamide

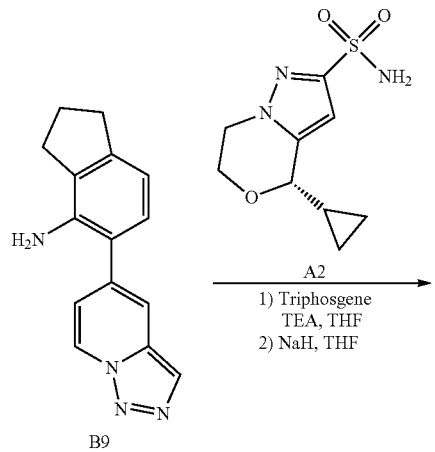

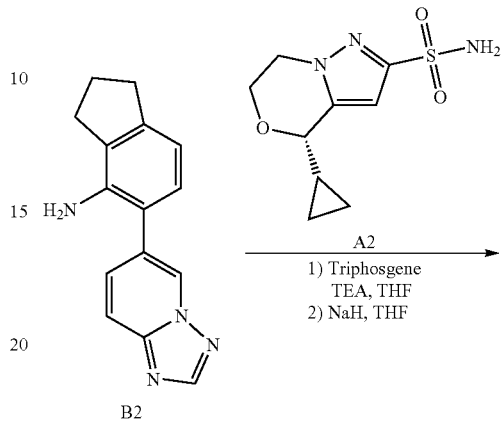

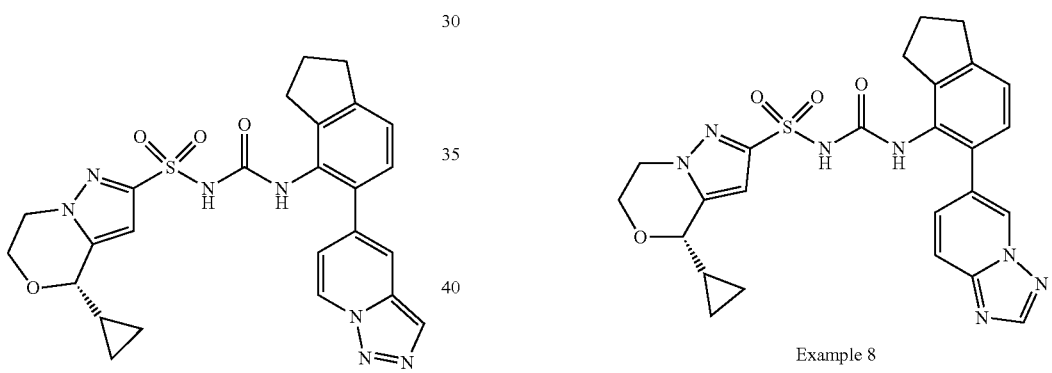

The title compound was prepared as described for Example 1 from (S)-4-cyclopropyl-6,7-dihydro-4H-pyrazolo[5,1-c][1,4]oxazine-2-sulfonamide (intermediate A2) and 5-([1,2,3]triazolo[1,5-a]pyridin-5-yl)-2,3-dihydro-1H-inden-4-amine (intermediate B9). The residue was purified by prep.HPLC to give the title compound as white solid. $^1$H NMR (400 MHz, DMSO-$d_6$) δ 8.80 (s, 1H), 8.47 (s, 1H), 7.72 (d, J=9.2 Hz, 1H), 7.64 (d, J=9.1 Hz, 1H), 7.14 (dd, J=17.0, 7.6 Hz, 2H), 6.28 (s, 1H), 4.25 (d, J=11.5 Hz, 2H), 4.04 (s, 3H), 2.91 (t, J=7.3 Hz, 2H), 2.79 (t, J=7.2 Hz, 2H), 2.02-1.95 (m, 2H), 1.14-1.06 (m, 1H), 0.65 (s, 1H), 0.57 (d, J=8.1 Hz, 1H), 0.47 (d, J=9.2 Hz, 2H). LC/MS (ESI) m/z: 520 (M+H)$^+$.

The title compound was prepared as described for Example 1 from (S)-4-cyclopropyl-6,7-dihydro-4H-pyrazolo[5,1-c][1,4]oxazine-2-sulfonamide (intermediate A2) and 5-([1,2,4]triazolo[1,5-a]pyridin-6-yl)-2,3-dihydro-1H-inden-4-amine (intermediate B2). The residue was purified by prep.HPLC to give the title compound as white solid. $^1$H NMR (400 MHz, DMSO-$d_6$) δ 8.81 (s, 1H), 8.50 (s, 1H), 7.74 (d, J=9.1 Hz, 1H), 7.61 (d, J=9.0 Hz, 1H), 7.17 (q, J=7.8 Hz, 2H), 6.37 (s, 1H), 4.27 (d, J=11.8 Hz, 1H), 4.08 (s, 2H), 3.99-3.86 (m, 2H), 2.92 (t, J=7.7 Hz, 3H), 2.77 (t, J=7.3 Hz, 2H), 2.08 (s, 1H), 2.04-1.95 (m, 2H), 1.19-1.10 (m, 2H), 0.71-0.43 (m, 4H). LC/MS (ESI) m/z: 520 (M+H)$^+$.

Example 9: (R)-4-cyclopropyl-N-((6-methyl-5-(pyrazolo[1,5-a]pyridin-5-yl)-2,3-dihydro-1H-inden-4-yl)carbamoyl)-6,7-dihydro-4H-pyrazolo[5,1-c][1,4]oxazine-2-sulfonamide

Example 10: (R)-4-cyclopropyl-N-((5-(imidazo[1,5-a]pyridin-7-yl)-2,3-dihydro-1H-inden-4-yl)carbamoyl)-6,7-dihydro-4H-pyrazolo[5,1-c][1,4]oxazine-2-sulfonamide

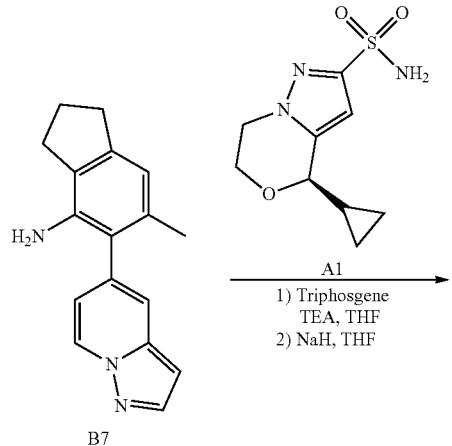

B7

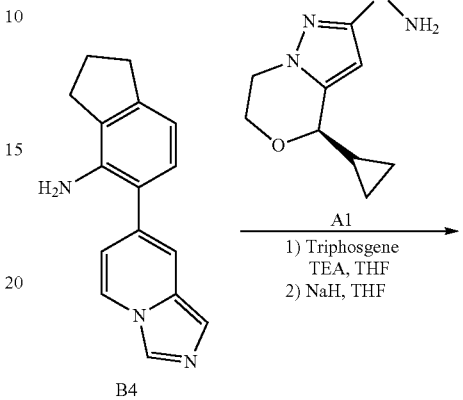

B4

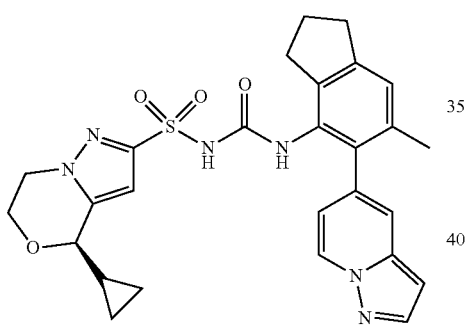

Example 9

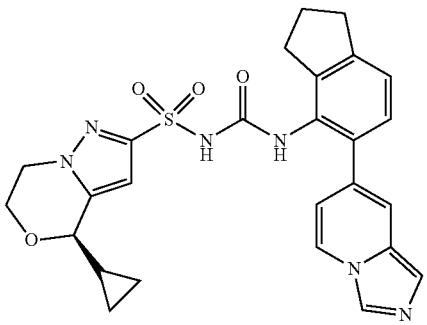

Example 10

The title compound was prepared as described for Example 1 from (R)-4-cyclopropyl-6,7-dihydro-4H-pyrazolo[5,1-c][1,4]oxazine-2-sulfonamide (intermediate A1) and 6-methyl-5-(pyrazolo[1,5-a]pyridin-5-yl)-2,3-dihydro-1H-inden-4-amine (intermediate B7). The residue was purified by prep.HPLC to give the title compound as white solid. $^1$H NMR (400 MHz, DMSO-$d_6$) δ 8.58 (s, 1H), 8.00 (d, J=2.0 Hz, 1H), 7.39 (s, 1H), 7.24 (s, 1H), 7.02 (s, 1H), 6.54 (dd, J=16.6, 9.6 Hz, 2H), 6.39 (s, 1H), 4.27 (d, J=12.3 Hz, 1H), 4.08 (s, 2H), 3.99 (d, J=8.4 Hz, 1H), 3.95-3.85 (m, 1H), 2.86 (t, J=7.3 Hz, 2H), 2.71-2.58 (m, 2H), 2.03 (s, 3H), 1.94 (d, J=8.8 Hz, 2H), 1.18-1.05 (m, 1H), 0.70-0.61 (m, 1H), 0.59-0.40 (m, 3H). LC/MS (ESI) m/z: 533 (M+H)$^+$.

The title compound was prepared as described for Example 1 from (R)-4-cyclopropyl-6,7-dihydro-4H-pyrazolo[5,1-c][1,4]oxazine-2-sulfonamide (intermediate A1) and 5-(imidazo[1,5-a]pyridin-7-yl)-2,3-dihydro-1H-inden-4-amine (intermediate B4). The residue was purified by prep.HPLC to give the title compound as white solid. $^1$H NMR (400 MHz, DMSO-$d_6$) δ 8.38 (s, 1H), 8.29 (d, J=7.3 Hz, 1H), 7.43 (s, 1H), 7.34 (s, 1H), 7.15 (q, J=8.0 Hz, 2H), 6.55 (dd, J=27.8, 7.4 Hz, 2H), 4.27 (d, J=11.8 Hz, 1H), 4.08 (d, J=20.7 Hz, 2H), 3.98 (d, J=9.1 Hz, 1H), 3.95-3.85 (m, 1H), 2.90 (t, J=7.4 Hz, 2H), 2.72-2.64 (m, 2H), 1.99 (dd, J=16.7, 9.5 Hz, 2H), 1.16-1.06 (m, 1H), 0.74-0.62 (m, 1H), 0.60-0.40 (m, 3H). LC/MS (ESI) m/z: 519 (M+H)$^+$.

Example 11: (R)-4-cyclopropyl-N-((5-(imidazo[1,2-a]pyridin-7-yl)-2,3-dihydro-1H-inden-4-yl)carbamoyl)-6,7-dihydro-4H-pyrazolo[5,1-c][1,4]oxazine-2-sulfonamide Example 12: (R)-4-cyclopropyl-N-((5-(imidazo[1,5-a]pyridin-6-yl)-2,3-dihydro-1H-inden-4-yl)carbamoyl)-6,7-dihydro-4H-pyrazolo[5,1-c][1,4]oxazine-2-sulfonamide

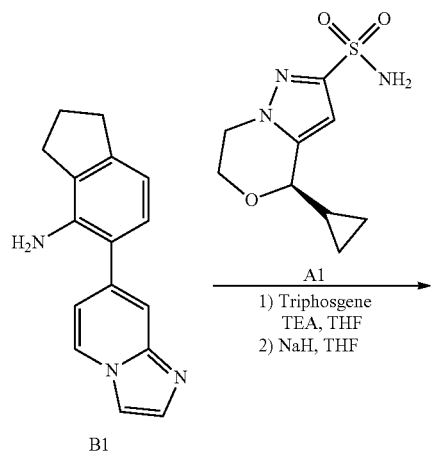

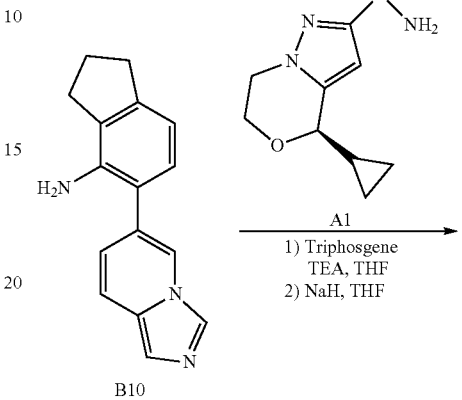

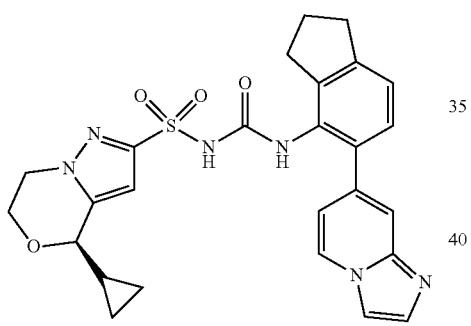

Example 11

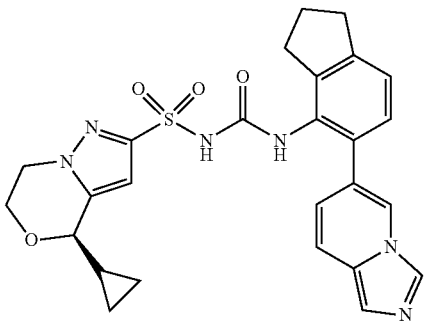

Example 12

The title compound was prepared as described for Example 1 from (R)-4-cyclopropyl-6,7-dihydro-4H-pyrazolo[5,1-c][1,4]oxazine-2-sulfonamide (intermediate A1) and 5-(imidazo[1,2-a]pyridin-7-yl)-2,3-dihydro-1H-inden-4-amine (intermediate B1). The residue was purified by prep.HPLC to give the title compound as white solid. $^1$H NMR (400 MHz, DMSO-$d_6$) δ 8.53 (d, J=6.9 Hz, 1H), 7.98 (s, 1H), 7.61 (s, 1H), 7.44 (s, 1H), 7.21 (q, J=7.6 Hz, 2H), 6.82-6.80 (m, 1H), 6.60 (s, 1H), 4.32-4.27 (m, 1H), 4.18-4.14 (m, 2H), 4.03 (d, J=8.7 Hz, 1H), 3.96-3.90 (m, 1H), 2.92 (t, J=7.2 Hz, 2H), 2.70-2.66 (m, 2H), 2.03-1.96 (m, 3H), 1.16-1.10 (m, 1H), 0.69-0.63 (m, 1H), 0.61-0.50 (m, 2H), 0.49-0.43 (m, 1H). LC/MS (ESI) m/z: 519 (M+H)$^+$.

The title compound was prepared as described for Example 1 from (R)-4-cyclopropyl-6,7-dihydro-4H-pyrazolo[5,1-c][1,4]oxazine-2-sulfonamide (intermediate A1) and 5-(imidazo[1,5-a]pyridin-6-yl)-2,3-dihydro-1H-inden-4-amine (intermediate B10). The residue was purified by prep.HPLC to give the title compound as white solid. $^1$H NMR (400 MHz, DMSO-$d_6$) δ 8.35 (s, 1H), 8.26 (s, 1H), 7.51 (d, J=9.7 Hz, 1H), 7.38 (s, 1H), 7.21 (d, J=7.9 Hz, 1H), 7.16 (d, J=7.6 Hz, 1H), 6.66 (d, J=9.2 Hz, 1H), 6.58 (s, 1H), 4.29 (d, J=11.9 Hz, 1H), 4.14 (s, 2H), 4.01 (d, J=8.8 Hz, 1H), 3.94 (d, J=13.1 Hz, 1H), 2.92 (t, J=7.2 Hz, 2H), 2.68 (d, J=6.9 Hz, 2H), 2.00 (t, J=7.3 Hz, 2H), 1.16-1.08 (m, 1H), 0.70-0.62 (m, 1H), 0.60-0.45 (m, 3H). LC/MS (ESI) m/z: 519 (M+H)$^+$.

Example 13: (R)-N-((5-([1,2,4]triazolo[1,5-a]pyridin-7-yl)-2,3-dihydro-1H-inden-4-yl)carbamoyl)-4-cyclopropyl-6,7-dihydro-4H-pyrazolo[5,1-c][1,4]oxazine-2-sulfonamide Example 14: (R)-N-((5-([1,2,4]triazolo[4,3-a]pyridin-6-yl)-2,3-dihydro-1H-inden-4-yl)carbamoyl)-4-cyclopropyl-6,7-dihydro-4H-pyrazolo[5,1-c][1,4]oxazine-2-sulfonamide

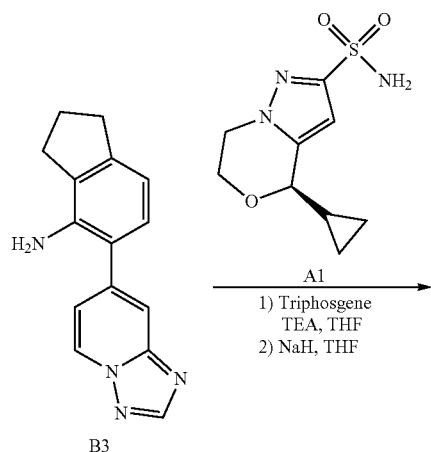

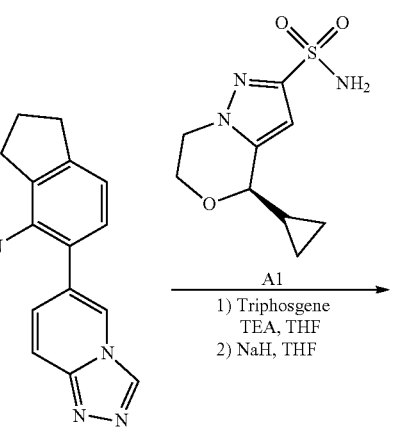

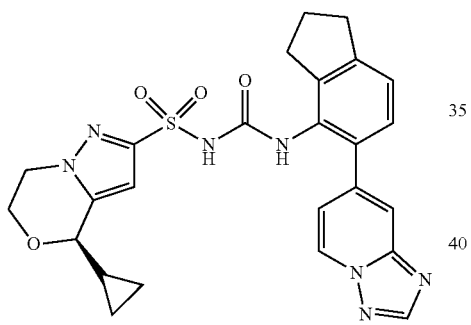

Example 13

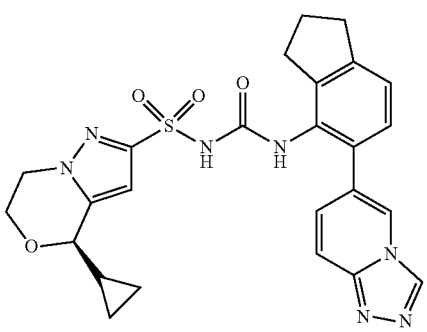

Example 14

The title compound was prepared as described for Example 1 from (R)-4-cyclopropyl-6,7-dihydro-4H-pyrazolo[5,1-c][1,4]oxazine-2-sulfonamide (intermediate A1) and 5-([1,2,4]triazolo[1,5-a]pyridin-7-yl)-2,3-dihydro-1H-inden-4-amine (intermediate B3). The residue was purified by prep.HPLC to give the title compound as white solid. $^1$H NMR (400 MHz, DMSO-$d_6$) δ 8.86 (d, J=7.1 Hz, 1H), 8.51 (s, 1H), 7.71 (s, 1H), 7.22 (s, 2H), 7.13 (d, J=7.0 Hz, 1H), 6.49 (d, J=14.2 Hz, 1H), 4.28 (dt, J=11.6, 3.3 Hz, 1H), 4.13 (d, J=4.5 Hz, 2H), 3.99 (d, J=8.9 Hz, 1H), 3.96-3.89 (m, 1H), 2.93 (t, J=7.4 Hz, 2H), 2.74 (t, J=7.2 Hz, 2H), 2.04-1.97 (m, 2H), 1.11 (ddd, J=12.2, 8.4, 3.8 Hz, 1H), 0.65 (dt, J=8.5, 4.3 Hz, 1H), 0.57 (dd, J=7.9, 3.6 Hz, 1H), 0.51-0.42 (m, 2H). LC/MS (ESI) m/z: 520 (M+H)$^+$.

The title compound was prepared as described for Example 1 from (R)-4-cyclopropyl-6,7-dihydro-4H-pyrazolo[5,1-c][1,4]oxazine-2-sulfonamide (intermediate A1) and 5-([1,2,4]triazolo[4,3-a]pyridin-6-yl)-2,3-dihydro-1H-inden-4-amine (intermediate B8). The residue was purified by prep.HPLC to give the title compound as white solid. $^1$H NMR (400 MHz, DMSO-$d_6$) δ 9.21 (d, J=9.4 Hz, 1H), 8.48 (d, J=14.7 Hz, 1H), 7.63 (d, J=9.6 Hz, 1H), 7.35 (d, J=8.8 Hz, 1H), 7.12 (s, 2H), 6.29 (s, 1H), 4.26 (s, 1H), 4.04 (s, 1H), 3.94 (d, J=9.4 Hz, 1H), 2.91 (t, J=7.5 Hz, 2H), 2.79 (t, J=7.1 Hz, 2H), 2.33 (s, 1H), 2.02-1.92 (m, 2H), 1.24 (s, 1H), 1.07 (d, J=8.1 Hz, 1H), 0.70-0.41 (m, 5H). LC/MS (ESI) m/z: 520 (M+H)$^+$.

Example 15: (R)-4-cyclopropyl-N-((5-(imidazo[1,2-a]pyridin-7-yl)-6-methyl-2,3-dihydro-1H-inden-4-yl)carbamoyl)-6,7-dihydro-4H-pyrazolo[5,1-c][1,4]oxazine-2-sulfonamide Example 16: 7-cyclopropyl-N-((5-(pyrazolo[1,5-a]pyridin-5-yl)-2,3-dihydro-1H-inden-4-yl)carbamoyl)-6,7-dihydro-4H-pyrazolo[5,1-c][1,4]oxazine-2-sulfonamide

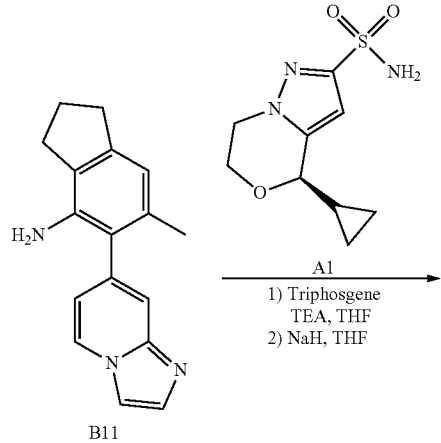

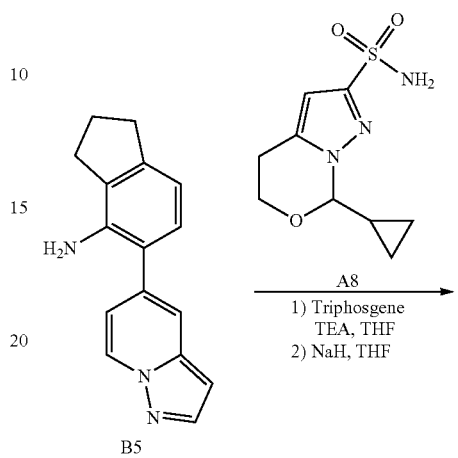

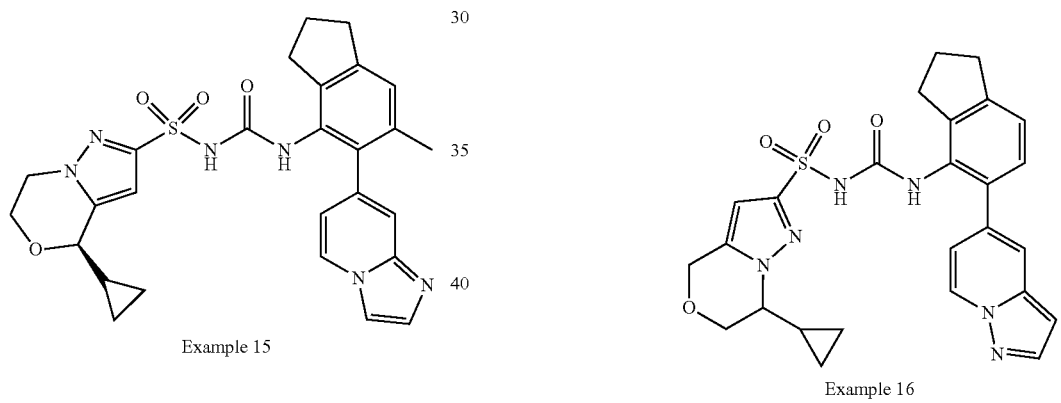

The title compound was prepared as described for Example 1 from (R)-4-cyclopropyl-6,7-dihydro-4H-pyrazolo[5,1-c][1,4]oxazine-2-sulfonamide (intermediate A1) and 5-(imidazo[1,2-a]pyridin-7-yl)-6-methyl-2,3-dihydro-1H-inden-4-amine (intermediate B11). The residue was purified by prep.HPLC to give the title compound as white solid. $^1$H NMR (400 MHz, DMSO-$d_6$) δ 8.55 (d, J=5.9 Hz, 1H), 8.01 (s, 1H), 7.62 (s, 1H), 7.26 (s, 1H), 7.09 (s, 1H), 6.57 (d, J=6.6 Hz, 2H), 4.29-4.30 (m, 1H), 4.15-4.17 (m, 2H), 4.06 (d, J=8.3 Hz, 1H), 3.93-3.95 (m, 1H), 2.88 (t, J=7.5 Hz, 2H), 2.66 (d, J=21.1 Hz, 2H), 2.05 (s, 3H), 1.98-1.92 (m, 2H), 1.14-1.16 (m, 1H), 0.66-0.67 (m, 1H), 0.63-0.52 (m, 2H), 0.47-0.48 (m, 1H). LC/MS (ESI) m/z: 533 (M+H)$^+$.

The title compound was prepared as described for Example 1 from 7-cyclopropyl-6,7-dihydro-4H-pyrazolo[5,1-c][1,4]oxazine-2-sulfonamide (intermediate A8) and 5-(pyrazolo[1,5-a]pyridin-5-yl)-2,3-dihydro-1H-inden-4-amine (intermediate B5). The residue was purified by prep.HPLC to give the title compound as white solid. $^1$H NMR (400 MHz, CDCl$_3$) δ 8.34 (d, J=7.2 Hz, 1H), 7.93 (d, J=2.1 Hz, 1H), 7.45 (s, 1H), 7.22 (d, J=7.7 Hz, 1H), 7.15 (d, J=7.6 Hz, 1H), 6.70 (dd, J=7.2, 1.6 Hz, 1H), 6.47 (d, J=1.8 Hz, 1H), 6.24 (s, 1H), 4.77 (d, J=15.3 Hz, 1H), 4.67 (d, J=15.2 Hz, 1H), 4.03-3.94 (m, 2H), 3.29-3.23 (m, 1H), 2.98 (t, J=7.4 Hz, 2H), 2.78 (t, J=7.3 Hz, 2H), 2.07 (dt, J=14.0, 7.0 Hz, 2H), 1.18-1.08 (m, 1H), 0.69-0.52 (m, 3H), 0.33-0.24 (m, 1H). LC/MS (ESI) m/z: 519 (M+H)$^+$.

Example 17: N-((6-methyl-5-(pyrazolo[1,5-a]pyridin-5-yl)-2,3-dihydro-1H-inden-4-yl)carbamoyl)-6',7'-dihydrospiro[cyclobutane-1,4'-pyrazolo[5,1-c][1,4]oxazine]-2'-sulfonamide Example 18: 8-cyclopropyl-N-((6-methyl-5-(pyrazolo[1,5-a]pyridin-5-yl)-2,3-dihydro-1H-inden-4-yl)carbamoyl)-5,6-dihydro-8H-imidazo[2,1-c][1,4]oxazine-2-sulfonamide

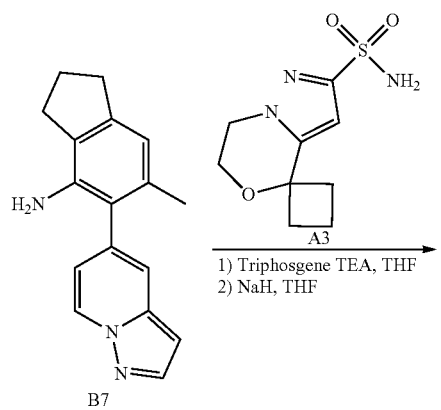

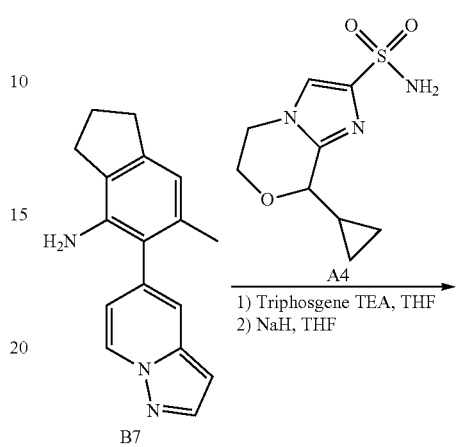

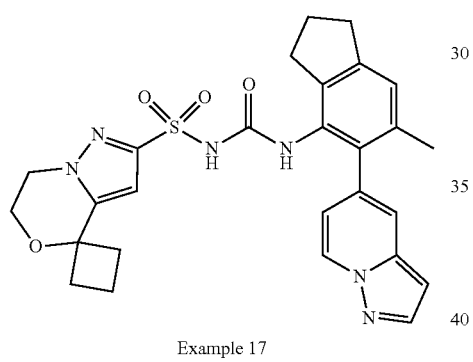

Example 17

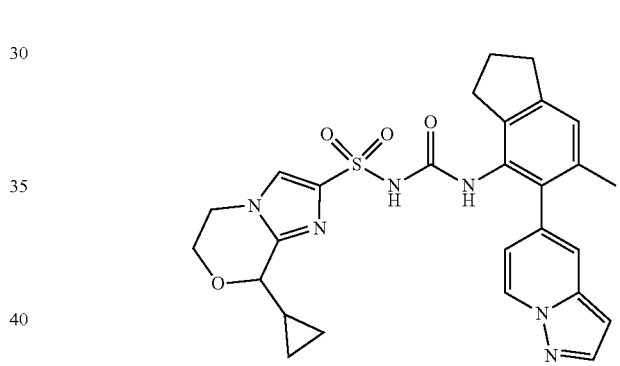

Example 18

The title compound was prepared as described for Example 1 from 6',7'-dihydrospiro[cyclobutane-1,4'-pyrazolo[5,1-c][1,4]oxazine]-2'-sulfonamide (intermediate A3) and 6-methyl-5-(pyrazolo[1,5-a]pyridin-5-yl)-2,3-dihydro-1H-inden-4-amine (intermediate B7). The residue was purified by prep.HPLC to give the title compound as white solid. $^1$H NMR (400 MHz, DMSO-d$_6$) δ 8.59 (dd, J=15.4, 7.1 Hz, 1H), 8.01 (d, J=8.1 Hz, 1H), 7.41 (d, J=5.3 Hz, 2H), 7.04 (d, J=18.8 Hz, 1H), 6.56 (dd, J=15.0, 8.5 Hz, 2H), 4.07 (d, J=28.8 Hz, 2H), 2.87-2.88 (m, 2H), 2.68-2.69 (m, 2H), 2.35 (d, J=8.3 Hz, 4H), 2.05 (s, 3H), 1.96 (d, J=8.3 Hz, 4H), 1.51 (d, J=8.2 Hz, 1H), 1.24-1.25 (m, 1H). LC/MS (ESI) m/z: 533 (M+H)$^+$.

The title compound was prepared as described for Example 1 from 8-cyclopropyl-5,6-dihydro-8H-imidazo[2,1-c][1,4]oxazine-2-sulfonamide (intermediate A4) and 6-methyl-5-(pyrazolo[1,5-a]pyridin-5-yl)-2,3-dihydro-1H-inden-4-amine (intermediate B7). The residue was purified by prep.HPLC to give the title compound as white solid. $^1$H NMR (400 MHz, DMSO-d$_6$) δ 8.61 (t, J=6.7 Hz, 1H), 8.01 (d, J=2.2 Hz, 1H), 7.39 (d, J=6.1 Hz, 2H), 7.04 (s, 1H), 6.58 (d, J=1.7 Hz, 1H), 6.55-6.47 (m, 1H), 4.17 (dd, J=23.8, 10.7 Hz, 2H), 4.04-3.99 (m, 2H), 3.87-3.82 (m, 1H), 2.86 (t, J=6.9 Hz, 2H), 2.64-2.59 (m, 2H), 2.03 (s, 3H), 1.93 (t, J=8.0 Hz, 2H), 1.23 (br, 1H), 0.62 (dd, J=10.6, 9.7 Hz, 1H), 0.47 (d, J=4.7 Hz, 3H). LC/MS (ESI) m/z: 533 (M+H)$^+$.

Example 19: 8-cyclopropyl-N-((6-methyl-5-(1H-pyrrolo[2,3-b]pyridin-4-yl)-2,3-dihydro-1H-inden-4-yl)carbamoyl)-5,6-dihydro-8H-imidazo[2,1-c][1,4]oxazine-2-sulfonamide

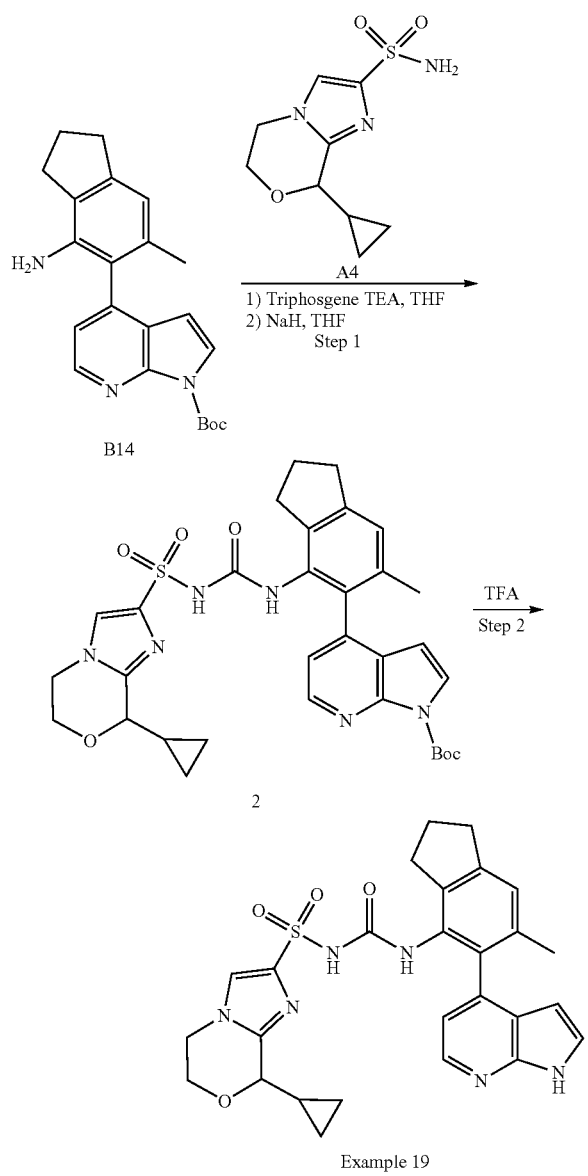

Example 19

Step 1: tert-butyl 4-(4-(3-((8-cyclopropyl-5,6-dihydro-8H-imidazo[2,1-c][1,4]oxazin-2-yl)sulfonyl)ureido)-6-methyl-2,3-dihydro-1H-inden-5-yl)-1H-pyrrolo[2,3-b]pyridine-1-carboxylate To a solution of tert-butyl 4-(4-amino-2,3-dihydro-1H-inden-5-yl)-1H-pyrrolo[2,3-b]pyridine-1-carboxylate (B14, 86 mg, 0.25 mmol) and TEA (75 mg, 0.75 mmol) in THF (4 mL) was added triphosgene (24 mg, 0.08 mmol) at 0° C. After being stirred at 0° C. for 0.5 hr, the mixture was filtered and the filtrate was directly used in the next reaction. To a solution of 8-cyclopropyl-5,6-dihydro-8H-imidazo[2,1-c][1,4]oxazine-2-sulfonamide (A4, 60 mg, 0.247 mmol) in THF (4 mL) was added NaH (30 mg, 0.75 mmol, 60% dispersion in mineral oil) at 0° C. and the mixture was stirred at room temperature for 30 min. The above filtrate was added to the mixture at 0° C. and the resulting mixture was stirred at r.t. for 3 hrs. The mixture was poured into ice water and acidified with 1N aq·HCl to pH-4. The mixture was extracted with EtOAc (3×10 mL) and the combined organic layers were washed with brine, dried over anhydrous $Na_2SO_4$, filtered and concentrated to dryness. The residue was purified by flash chromatography (silica gel, 0-8% MeOH in PE) to give the title compound (100 mg, 64% yield) as white solid. LC/MS (ESI) m/z: 633 (M+H)$^+$.

Step 2: 3-({8-cyclopropyl-5H,6H,8H-imidazo[2,1-c][1,4]oxazin-2-yl}sulfonyl)-1-(6-methyl-5-{1H-pyrrolo[2,3-b]pyridin-4-yl}-2,3-dihydro-1H-inden-4-yl)urea To a solution of tert-butyl 4-(4-(3-((8-cyclopropyl-5,6-dihydro-8H-imidazo[2,1-c][1,4]oxazin-2-yl)sulfonyl)ureido)-6-methyl-2,3-dihydro-1H-inden-5-yl)-1H-pyrrolo[2,3-b]pyridine-1-carboxylate (100 mg, 0.16 mmol) in DCM (8 mL) was added TFA (2 mL) and the reaction was stirred at room temperature for 1 hr. The reaction was poured into aq·$NaHCO_3$ solution and extracted with DCM (2×10 mL). The combined organic layers were washed with brine, dried over $Na_2SO_4$, filtered and concentrated to dryness. The residue was purified by prep-HPLC to give the title compound (15 mg, 18% yield) as white solid. $^1$H NMR (400 MHz, DMSO-d$_6$) δ 11.69 (s, 1H), 8.23-8.15 (m, 1H), 7.48 (d, J=8.7 Hz, 1H), 7.40-7.35 (m, 1H), 7.08 (d, J=15.7 Hz, 2H), 6.73 (dd, J=8.3, 4.9 Hz, 1H), 5.98-5.87 (m, 1H), 4.21 (dt, J=12.1, 3.7 Hz, 1H), 4.14 (dd, J=7.5, 5.7 Hz, 1H), 4.05 (dd, J=6.0, 3.7 Hz, 2H), 3.87 (ddd, J=8.3, 6.7, 2.6 Hz, 1H), 2.89 (t, J=7.5 Hz, 2H), 2.61-2.54 (m, 2H), 2.00-1.91 (m, 2H), 1.88 (s, 3H), 1.21 (dd, J=13.0, 7.8 Hz, 1H), 0.69-0.58 (m, 1H), 0.55-0.44 (m, 3H). LC/MS (ESI) m/z: 533 (M+H)$^+$.

Example 20: 4,4-dimethyl-N-((6-methyl-5-(1H-pyrrolo[2,3-b]pyridin-4-yl)-2,3-dihydro-1H-inden-4-yl)carbamoyl)-6,7-dihydro-4H-pyrazolo[5,1-c][1,4]oxazine-2-sulfonamide

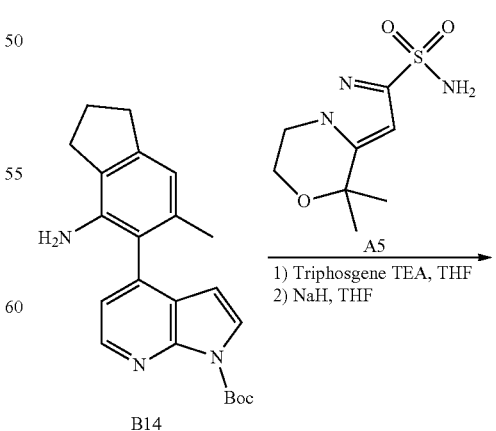

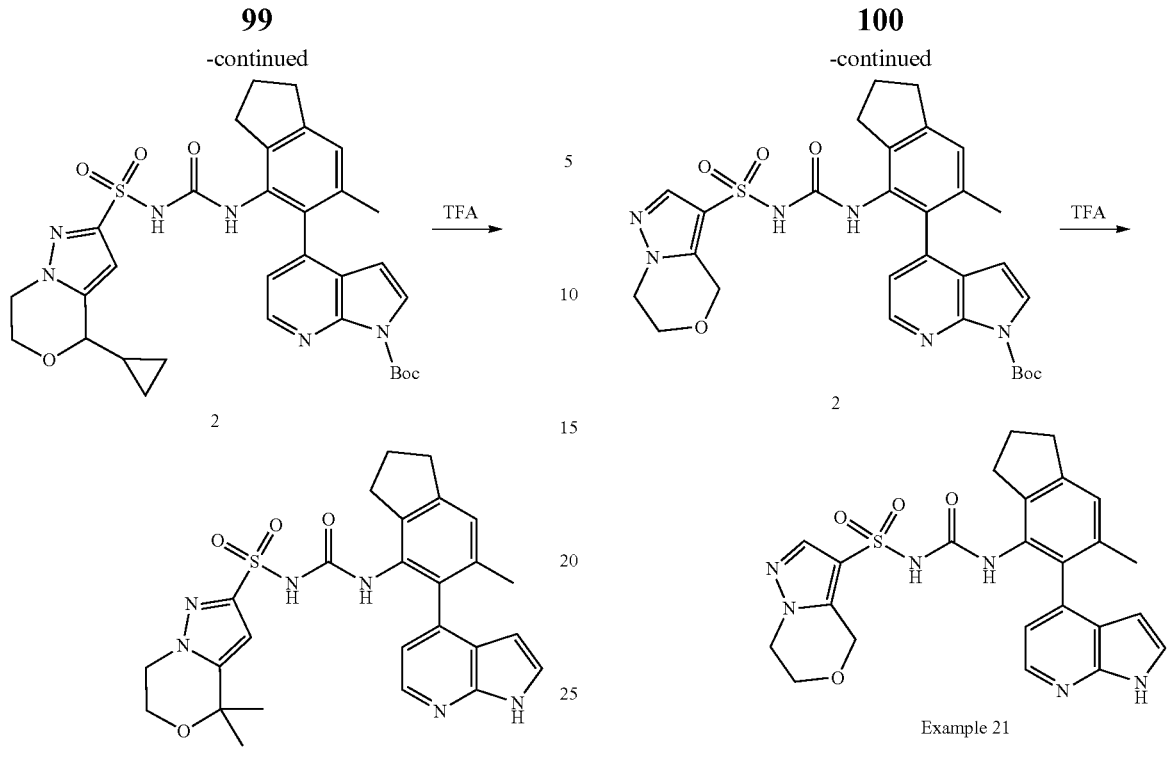

Example 20

The title compound was prepared as described for Example 19 from 4,4-dimethyl-6,7-dihydro-4H-pyrazolo[5,1-c][1,4]oxazine-2-sulfonamide (intermediate A5) and tert-butyl 4-(4-amino-6-methyl-2,3-dihydro-1H-inden-5-yl)-1H-pyrrolo[2,3-b]pyridine-1-carboxylate (intermediate B14). The residue was purified by prep.HPLC to give the title compound as white solid. $^1$H NMR (400 MHz, DMSO-d$_6$) δ 11.67 (s, 1H), 8.19 (d, J=4.8 Hz, 1H), 7.35 (s, 1H), 7.01 (s, 1H), 6.74 (d, J=4.7 Hz, 1H), 5.92 (s, 1H), 4.05 (s, 4H), 2.87 (t, J=7.6 Hz, 2H), 2.59 (s, 2H), 1.95-1.90 (m, 2H), 1.87 (s, 3H), 1.46 (s, 6H). LC/MS (ESI) m/z: 521 (M+H)$^+$.

Example 21: N-((6-methyl-5-(1H-pyrrolo[2,3-b]pyridin-4-yl)-2,3-dihydro-1H-inden-4-yl)carbamoyl)-6,7-dihydro-4H-pyrazolo[5,1-c][1,4]oxazine-3-sulfonamide Example 21

The title compound was prepared as described for Example 19 from 6,7-dihydro-4H-pyrazolo[5,1-c][1,4]oxazine-3-sulfonamide (intermediate A7) and tert-butyl 4-(4-amino-6-methyl-2,3-dihydro-1H-inden-5-yl)-1H-pyrrolo[2,3-b]pyridine-1-carboxylate (intermediate B14). The residue was purified by prep.HPLC to give the title compound as white solid. 1H NMR (400 MHz, CD$_3$OD) δ 8.13 (d, J=4.9 Hz, 1H), 7.58 (s, 1H), 7.28 (d, J=3.5 Hz, 1H), 7.11 (s, 1H), 6.82 (d, J=4.9 Hz, 1H), 6.04 (d, J=3.5 Hz, 1H), 4.85-4.84 (m, 2H), 4.19 (t, J=5.0 Hz, 2H), 4.08 (t, J=5.0 Hz, 2H), 2.96 (t, J=7.4 Hz, 2H), 2.79 (s, 2H), 2.11-2.02 (m, 2H), 1.94 (s, 3H). LC/MS (ESI) (m/z): 493 (M+H)$^+$.

Example 22: 4,4-dimethyl-N-((6-methyl-5-(pyrazolo[1,5-a]pyridin-5-yl)-2,3-dihydro-1H-inden-4-yl)carbamoyl)-6,7-dihydro-4H-pyrazolo[5,1-c][1,4]oxazine-2-sulfonamide

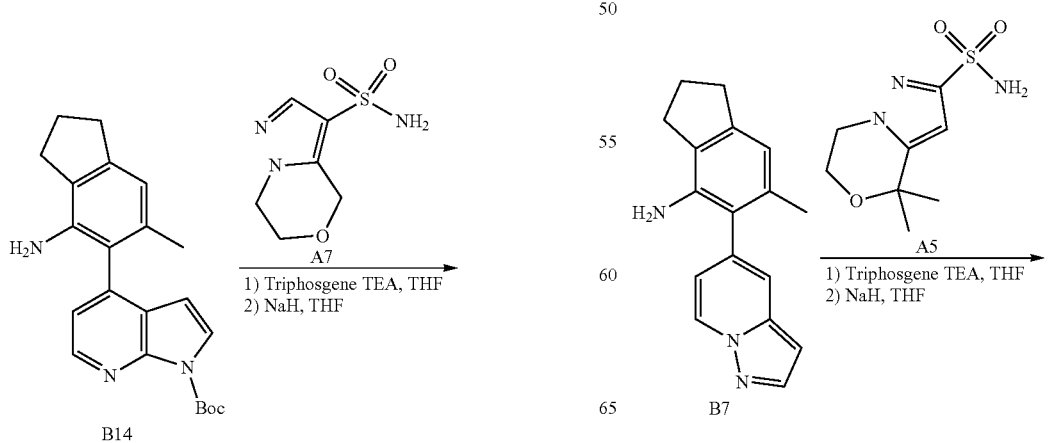

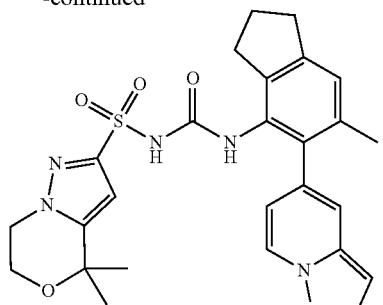

Example 22

The title compound was prepared as described for Example 1 from 4,4-dimethyl-6,7-dihydro-4H-pyrazolo[5,1-c][1,4]oxazine-2-sulfonamide (intermediate A5) and 6-methyl-5-(pyrazolo[1,5-a]pyridin-5-yl)-2,3-dihydro-1H-inden-4-amine (intermediate B7). The residue was purified by prep.HPLC to give the title compound as white solid. ¹H NMR (400 MHz, CD₃OD) δ 8.50 (d, J=7.1 Hz, 1H), 7.97 (d, J=2.3 Hz, 1H), 7.44 (s, 1H), 7.10 (s, 1H), 6.65 (dd, J=7.1, 1.5 Hz, 1H), 6.59 (d, J=1.7 Hz, 1H), 6.53 (s, 1H), 4.15-4.09 (m, 4H), 2.93 (t, J=7.4 Hz, 2H), 2.68 (dd, J=16.6, 8.0 Hz, 2H), 2.10 (s, 3H), 2.06-2.00 (m, 2H), 1.53 (s, 6H). LC/MS (ESI) m/z: 521 (M+H)⁺.

Example 23: N-((6-methyl-5-(pyrazolo[1,5-a]pyridin-5-yl)-2,3-dihydro-1H-inden-4-yl)carbamoyl)-6,7-dihydro-4H-pyrazolo[5,1-c][1,4]oxazine-2-sulfonamide

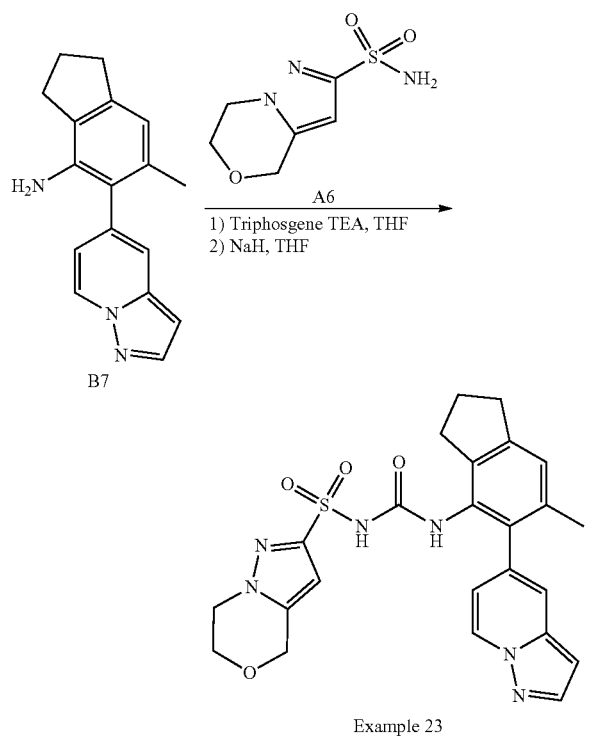

Example 23

The title compound was prepared as described for Example 1 from 6,7-dihydro-4H-pyrazolo[5,1-c][1,4]oxazine-2-sulfonamide (intermediate A6) and 6-methyl-5-(pyrazolo[1,5-a]pyridin-5-yl)-2,3-dihydro-1H-inden-4-amine (intermediate B7). The residue was purified by prep.HPLC to give the title compound as white solid. ¹H NMR (400 MHz, CD₃OD) δ 8.47 (d, J=7.1 Hz, 1H), 7.97 (d, J=2.3 Hz, 1H), 7.42 (s, 1H), 7.08 (d, J=13.5 Hz, 1H), 6.64 (d, J=7.1 Hz, 1H), 6.57 (d, J=2.0 Hz, 1H), 6.30 (s, 1H), 4.80 (s, 2H), 4.13 (s, 4H), 2.93 (t, J=7.3 Hz, 2H), 2.82-2.66 (m, 2H), 2.13-1.99 (m, 5H). LC/MS (ESI) (m/z): 493 (M+H)⁺.

Example 24: 1-cyclopropyl-N-((5-(pyrazolo[1,5-a]pyridin-5-yl)-2,3-dihydro-1H-inden-4-yl)carbamoyl)-2,3-dihydro-1H-pyrido[2,3-b][1,4]oxazine-7-sulfonamide

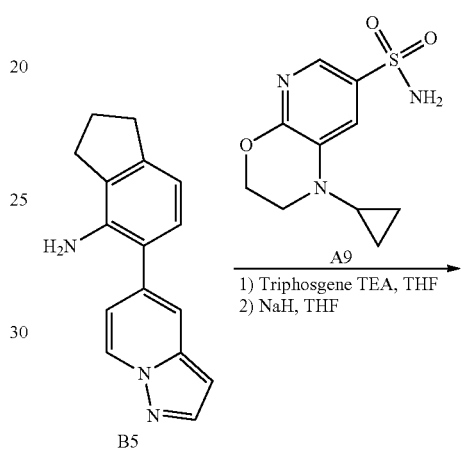

Example 24

The title compound was prepared as described for Example 1 from 1-cyclopropyl-2,3-dihydro-1H-pyrido[2,3-b][1,4]oxazine-7-sulfonamide (intermediate A9) and 5-(pyrazolo[1,5-a]pyridin-5-yl)-2,3-dihydro-1H-inden-4-amine (intermediate B5). The residue was purified by prep.HPLC to give the title compound as white solid. ¹H NMR (400 MHz, DMSO-d₆) δ 8.51-8.43 (m, 1H), 7.99 (d, J=2.2 Hz, 1H), 7.95-7.90 (m, 1H), 7.69 (d, J=2.1 Hz, 1H), 7.50 (s, 1H), 7.16 (s, 2H), 6.72-6.62 (m, 1H), 6.54 (d, J=1.7 Hz, 1H), 4.40 (s, 3H), 2.92 (s, 2H), 2.70-2.66 (m, 2H), 2.37-2.23 (m, 2H), 1.99 (s, 3H), 1.07 (d, J=5.2 Hz, 1H), 0.82-0.77 (m, 2H), 0.56 (s, 2H). LC/MS (ESI) m/z: 531 (M+H)⁺.

Example 25: 1-cyclopropyl-N-((6-methyl-5-(pyrazolo[1,5-a]pyridin-5-yl)-2,3-dihydro-1H-inden-4-yl)carbamoyl)-2,3-dihydro-1H-pyrido[2,3-b][1,4]oxazine-7-sulfonamide

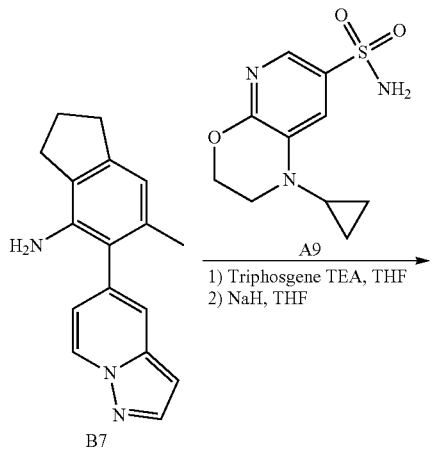

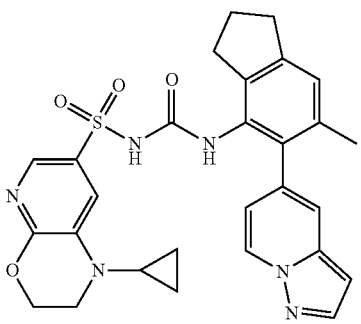

Example 25

The title compound was prepared as described for Example 1 from 1-cyclopropyl-2,3-dihydro-1H-pyrido[2,3-b][1,4]oxazine-7-sulfonamide (intermediate A9) and 6-methyl-5-(pyrazolo[1,5-a]pyridin-5-yl)-2,3-dihydro-1H-inden-4-amine (intermediate B7). The residue was purified by prep.HPLC to give the title compound as white solid. $^1$H NMR (400 MHz, DMSO-$d_6$) δ 8.51 (d, J=7.1 Hz, 1H), 8.00 (d, J=2.1 Hz, 1H), 7.85 (d, J=1.9 Hz, 1H), 7.64 (d, J=2.0 Hz, 1H), 7.33 (s, 1H), 7.05 (s, 1H), 6.56 (d, J=1.5 Hz, 1H), 6.46 (d, J=8.1 Hz, 1H), 4.40 (s, 2H), 2.91-2.83 (m, 4H), 2.60 (d, J=7.3 Hz, 2H), 2.29 (br, 1H), 2.03 (s, 3H), 1.94 (t, J=7.0 Hz, 2H), 0.80 (d, J=4.8 Hz, 2H), 0.57-0.56 (m, 2H). LC/MS (ESI) m/z: 545 (M+H)$^+$.

Example 26: N-((6-methyl-5-(pyrazolo[1,5-a]pyridin-5-yl)-2,3-dihydro-1H-inden-4-yl)carbamoyl)-6,7-dihydro-4H-pyrazolo[5,1-c][1,4]oxazine-3-sulfonamide

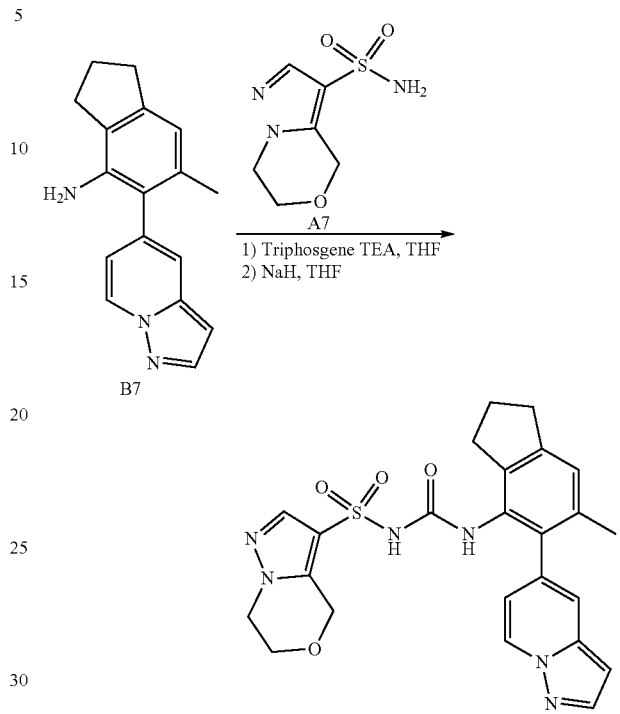

Example 26

The title compound was prepared as described for Example 1 from 6,7-dihydro-4H-pyrazolo[5,1-c][1,4]oxazine-3-sulfonamide (intermediate A7) and 6-methyl-5-(pyrazolo[1,5-a]pyridin-5-yl)-2,3-dihydro-1H-inden-4-amine (intermediate B7). The residue was purified by prep.HPLC to give the title compound as white solid. $^1$H NMR (400 MHz, CD$_3$OD) δ 8.45 (d, J=7.1 Hz, 1H), 7.96 (d, J=2.3 Hz, 1H), 7.66 (s, 1H), 7.35 (s, 1H), 7.11 (s, 1H), 6.59-6.54 (m, 2H), 4.93 (d, J=4.8 Hz, 2H), 4.19 (t, J=5.1 Hz, 2H), 4.07 (dd, J=7.5, 3.6 Hz, 2H), 2.94 (t, J=7.5 Hz, 2H), 2.75 (dd, J=10.7, 7.2 Hz, 2H), 2.10-2.04 (m, 5H). LC/MS (ESI) (m/z): 493 (M+H)$^+$.

Example 27: (S)-6-methoxy-N-((6-methyl-5-(pyrazolo[1,5-a]pyridin-5-yl)-2,3-dihydro-1H-inden-4-yl)carbamoyl)-6,7-dihydro-5H-pyrazolo[5,1-b][1,3]oxazine-3-sulfonamide

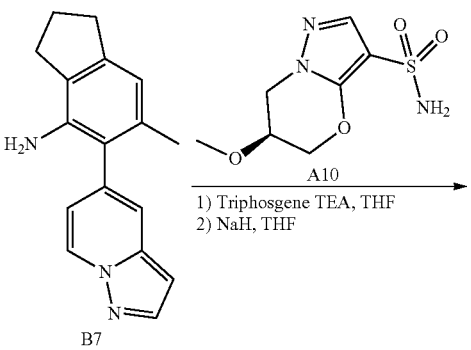

-continued

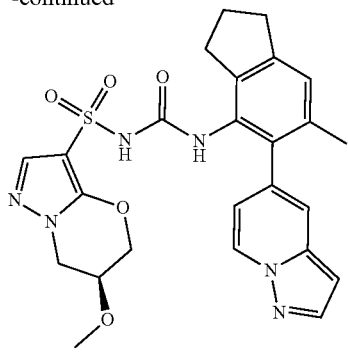

Example 27

The title compound was prepared as described for Example 1 from (S)-6-methoxy-6,7-dihydro-5H-pyrazolo[5,1-b][1,3]oxazine-3-sulfonamide (intermediate A10) and 6-methyl-5-(pyrazolo[1,5-a]pyridin-5-yl)-2,3-dihydro-1H-inden-4-amine (intermediate B7). The residue was purified by prep.HPLC to give the title compound as white solid. $^1$H NMR (400 MHz, DMSO-$d_6$) δ 8.62 (d, J=19.4 Hz, 1H), 8.03 (s, 1H), 7.47 (s, 1H), 7.40 (s, 1H), 7.07 (s, 1H), 6.59 (s, 1H), 6.49 (d, J=13.5 Hz, 1H), 4.54 (d, J=13.0 Hz, 1H), 4.25 (d, J=15.0 Hz, 4H), 4.05 (s, 1H), 2.88 (t, J=7.2 Hz, 2H), 2.62 (d, J=43.7 Hz, 3H), 2.33-2.34 (m, 1H), 2.04 (s, 3H), 2.01-1.92 (m, 3H), 1.24-1.25 (m, 1H). LC/MS (ESI) (m/z): 523 (M+H)$^+$.

Example 28: (S)-N-((5-(imidazo[1,2-a]pyridin-7-yl)-6-methyl-2,3-dihydro-1H-inden-4-yl)carbamoyl)-6-methoxy-6,7-dihydro-5H-pyrazolo[5,1-b][1,3]oxazine-3-sulfonamide

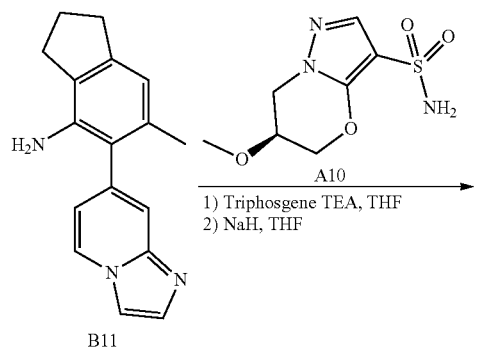

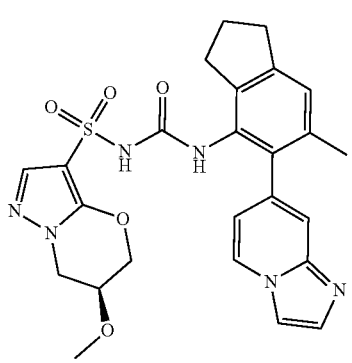

Example 28

The title compound was prepared as described for Example 1 from (S)-6-methoxy-6,7-dihydro-5H-pyrazolo[5,1-b][1,3]oxazine-3-sulfonamide (intermediate A10) and 5-(imidazo[1,2-a]pyridin-7-yl)-6-methyl-2,3-dihydro-1H-inden-4-amine (intermediate B11). The residue was purified by prep.HPLC to give the title compound as white solid. LC/MS (ESI) (m/z): 523 (M+H)$^+$.

Example 29: (S)-6-methoxy-N-((6-methyl-5-(pyrazolo[1,5-a]pyridin-6-yl)-2,3-dihydro-1H-inden-4-yl)carbamoyl)-6,7-dihydro-5H-pyrazolo[5,1-b][1,3]oxazine-3-sulfonamide

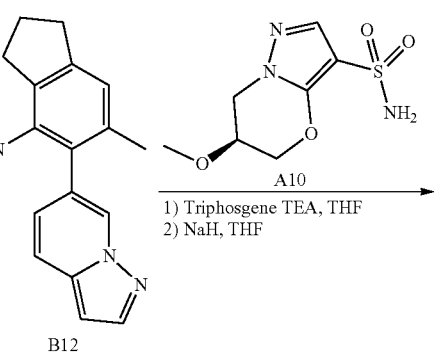

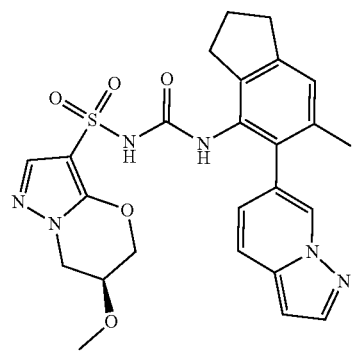

Example 29

The title compound was prepared as described for Example 1 from (S)-6-methoxy-6,7-dihydro-5H-pyrazolo[5,1-b][1,3]oxazine-3-sulfonamide (intermediate A10) and 6-methyl-5-(pyrazolo[1,5-a]pyridin-6-yl)-2,3-dihydro-1H-inden-4-amine (intermediate B12). The residue was purified by prep.HPLC to give the title compound as white solid. $^1$H NMR (400 MHz, DMSO-$d_6$) δ 8.41 (d, J=14.4 Hz, 1H), 8.03 (s, 1H), 7.68 (dd, J=15.8, 9.3 Hz, 1H), 7.49 (d, J=4.7 Hz, 1H), 7.08 (s, 1H), 6.83 (t, J=7.6 Hz, 1H), 6.67 (s, 1H), 4.56 (d, J=11.7 Hz, 1H), 4.36-4.12 (m, 3H), 4.05 (s, 1H), 3.41 (s, 3H), 2.88 (t, J=7.3 Hz, 2H), 2.64 (d, J=33.4 Hz, 2H), 2.05 (s, 3H), 2.01-1.89 (m, 2H). LC/MS (ESI) (m/z): 523 (M+H)$^+$.

Example 30: (S)-N-((5-(imidazo[1,2-a]pyridin-6-yl)-6-methyl-2,3-dihydro-1H-inden-4-yl)carbamoyl)-6-methoxy-6,7-dihydro-5H-pyrazolo[5,1-b][1,3]oxazine-3-sulfonamide

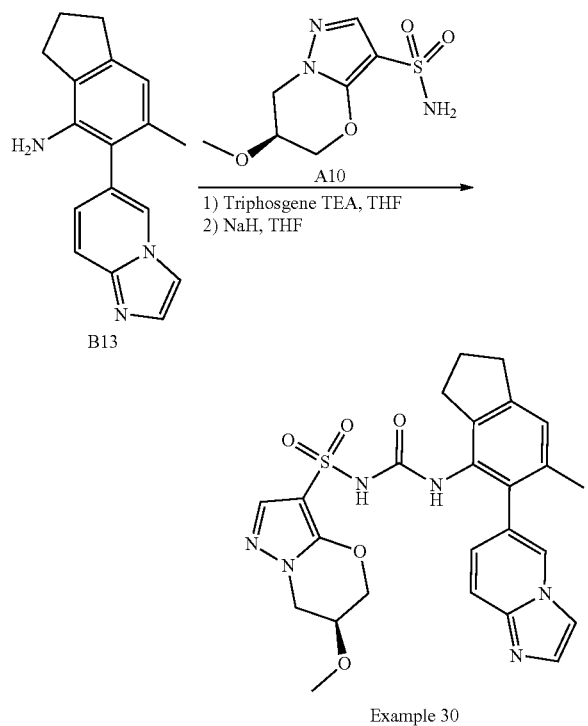

Example 30

The title compound was prepared as described for Example 1 from (S)-6-methoxy-6,7-dihydro-5H-pyrazolo[5,1-b][1,3]oxazine-3-sulfonamide (intermediate A10) and 5-(imidazo[1,2-a]pyridin-6-yl)-6-methyl-2,3-dihydro-1H-inden-4-amine (intermediate B13). The residue was purified by prep.HPLC to give the title compound as white solid. $^1$H NMR (400 MHz, DMSO-$d_6$) δ 8.30 (s, 1H), 7.90 (d, J=10.4 Hz, 1H), 7.60 (s, 1H), 7.56 (d, J=8 Hz, 1H) 7.52-7.47 (m, 1H), 7.08 (s, 1H), 6.87-6.78 (m, 1H), 4.54 (d, J=14.4 Hz, 1H), 4.35-4.28 (m, 1H), 4.23 (s, 2H), 4.05 (s, 1H), 3.38 (s, 3H), 2.88 (t, J=7.2 Hz, 2H), 2.67 (s, 2H), 2.62-2.56 (m, 1H), 2.04 (s, 3H), 2.02-1.85 (m, 2H). LC/MS (ESI) (m/z): 523 (M+H)$^+$.

Biological Studies

The following method was used for compound screening.
1. Seed THP-1 cells (5.56*10^5 cells/mL) containing 1.0 ug/mL LPS (SIGMA, L6529) in 45 uL RPMI 1640 medium (without FBS) into 384-well plate (Thermo Scientific, 164688).
2. Add 5 uL compound (10 doses starting from 5 uM, 1:3 dilution) or vehicle (0.05% DMSO in medium) to the appropriate wells.
3. Centrifuge the plates at 1000 rpm for 2 mins and incubate for 3 hrs at 37° C., 5% CO$_2$.
4. Add 5 uL nigericin (MEC, HY-100381) (final conc. 5 uM) to sample wells and positive control wells; add 5 uL RPMI 1640 medium to negative control wells.
5. Centrifuge plates at 1000 rpm for 2 mins and incubate for 1 hr at 37° C., 5% CO$_2$.
6. At the end of the incubation period, centrifuge plates at 1000 rpm for 6 mins and transfer 8 uL supernatant into 384-well assay plates (PerkinElmer, 6008280).
7. Add 8 ul RPMI 1640 medium into each well and spin down for 10 secs.
8. Prepare the standard solutions and pre-mixed IL1β antibodie solution of Human IL1β kits (PerkinElmer, 62HIL1BPEH) according to the instruction.
9. Add 16 uL standard solutions into clear wells of 384-well assay plates.
10. Add 4 uL pre-mixed IL1β antibodie solution to all wells including sample wells, positive control wells, negative control wells and standard solutions wells.
11. Seal the plates, spin down for 10 secs, incubation for overnight at RT and read on an HTRF® compatible reader (BMG LABTECH, PHERAstar FS).
12. The concentrations of IL1β for treated wells are calculated by the standard curve.
13. The IC$_{50}$ data is fitted to a non-liner regression equation (log inhibitor vs. response—Variable slope four parameters)).

The results of the pyroptosis assay are summarized in Table 2 below as THP IC$_{50}$.*

TABLE 2

| Example No | THP IC$_{50}$ |
|---|---|
| 1 | A |
| 2 | B |
| 3 | A |
| 4 | B |
| 5 | A |
| 6 | B |
| 7 | B |
| 8 | B |
| 9 | A |
| 10 | B |
| 11 | B |
| 12 | B |
| 13 | B |
| 14 | C |
| 15 | A |
| 16 | B |
| 17 | A |
| 18 | A |
| 19 | C |
| 20 | B |
| 21 | B |
| 22 | A |
| 23 | A |
| 24 | A |
| 25 | A |
| 26 | B |
| 27 | A |
| 28 | A |
| 29 | A |
| 30 | A |

*NLRP3 inhibitory activity - THP IC$_{50}$: A: ≤100 nM; B: >100 nM and ≤500 nM; C: >500 nM and ≤1 uM.

We claim:

1. A compound of Formulae (II)-(IV):

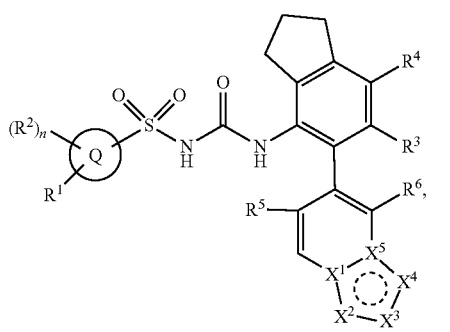
(II)

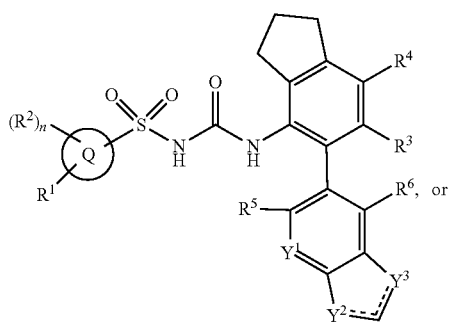
(III)

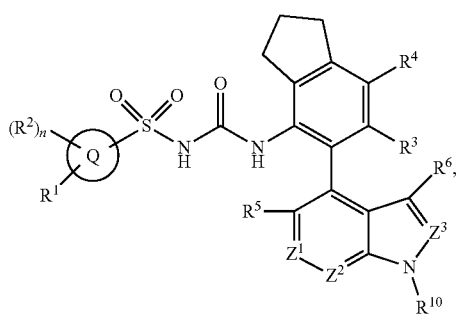
(IV)

or a pharmaceutically acceptable salt, tautomer or stereoisomer thereof, wherein:

Ring Q is a fused 6,5-bicyclic heteroaryl or a fused 6,6-bicyclic heteroaryl ring system comprising 1, 2 or 3 nitrogen atoms as ring members and optionally comprising 1 or 2 ring members selected from O, S or $S(=O_2)$, wherein the Ring Q bears $R^1$ and $R^2$ substituents as indicated in Formulae (II)-(IV), and optionally bears 1 or 2 $R^{12}$ substituents;

$X^1$ and $X^5$ are each independently N or C; and $X^2$, $X^3$, and $X^4$ are each independently N or $CR^7$, and the dashed circle denotes bonds forming a five-membered aromatic ring; provided that at least two but no more than three of $X^1$, $X^2$, $X^3$, $X^4$ and $X^5$ are N;

$Y^1$ is N or CH, $Y^2$ is N, $NR^8$ or CH, and $Y^3$ is N, $NR^8$ or CH, and

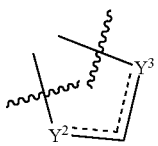

in Formula (III) denotes

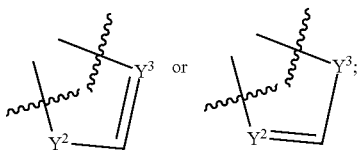

provided that two of $Y^1$, $Y^2$, and $Y^3$, are N;

$Z^1$ is N or CH, $Z^2$ is N or $CR^9$, and $Z^3$ is N or CH; provided that at least one of $Z^1$, $Z^2$, and $Z^3$, are N;

each occurrence of $R^1$ is independently hydrogen, $C_{1-4}$alkyl, halo$C_{1-4}$alkyl, $C_{3-7}$cycloalkyl, $C_{1-4}$alkoxy, $C_{3-7}$cycloalkoxy, oxo (=O), $NR^aR^b$, $C(=O)OR^a$, $OC(=O)R^a$, $C(=O)NR^aR^b$, $NR^bC(=O)R^a$, $C(=O)NHC(=O)R^a$, or 4-6-membered heterocyclyl, each of which is optionally substituted with one to three $R^{11}$;

each occurrence of $R^2$ is independently $C_{1-4}$alkyl, halo$C_{1-4}$alkyl, $C_{3-7}$cycloalkyl, halogen, CN, OH, $C_{1-4}$alkoxy, $NR^aR^b$, $C(=O)NR^aR^b$, or 4-6-membered heterocyclyl, each of which is optionally substituted with one to two $R^{11}$, or two $R^2$ groups at geminal position may optionally form a spiro $C_{3-5}$cycloalkyl;

$R^3$, $R^4$, $R^5$, and $R^6$ are each independently hydrogen, halogen, CN, $C_{1-4}$alkyl, or halo$C_{1-4}$alkyl;

each occurrence of $R^7$ is independently hydrogen or $C_{1-4}$alkyl;

each occurrence of $R^8$ is independently hydrogen or $C_{1-4}$alkyl;

each occurrence of $R^9$ is independently hydrogen, $C_{1-4}$alkyl or $C_{1-4}$alkoxy;

each occurrence of $R^{10}$ is independently hydrogen, $C_{1-4}$alkyl, $C_{3-7}$cycloalkyl, or 4-6-membered heterocyclyl optionally substituted with $C_{1-4}$alkyl;

each occurrence of $R^{11}$ is independently, $C_{1-4}$alkyl, halo$C_{1-4}$alkyl, halogen, CN, OH, $C_{3-7}$cycloalkyl, $C_{1-4}$alkoxy, $C_{3-7}$cycloalkoxy, $NR^aR^b$, $C(=O)OR^a$, $OC(=O)R^a$, $C(=O)NR^aR^b$, $NR^bC(=O)R^a$, $C(=O)NHC(=O)R^a$, or 4-6-membered heterocyclyl;

each occurrence of $R^{12}$ is independently hydrogen, $C_{1-4}$alkyl, halo$C_{1-4}$alkyl, $C_{3-7}$cycloalkyl, $C_{1-4}$alkyl-$C_{3-7}$cycloalkyl, $C_{1-4}$alkyl-$NR^aR^b$, $C(=O)R^a$, $C(=O)NR^aR^b$, or 4-6-membered heterocyclyl optionally substituted with one to three groups selected from $C_{1-4}$alkyl, halo$C_{1-4}$alkyl, $C_{3-7}$cycloalkyl, halogen, CN, OH, $C_{1-4}$alkoxy, $C_{3-7}$cycloalkoxy, or $NR^aR^b$, each occurrence of $R^a$ and $R^b$ is independently hydrogen, $C_{1-4}$alkyl, $C_{3-5}$cycloalkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl; and each occurrence of n is independently 0, 1, or 2.

2. The compound of claim 1, wherein
each occurrence of Ring Q is independently

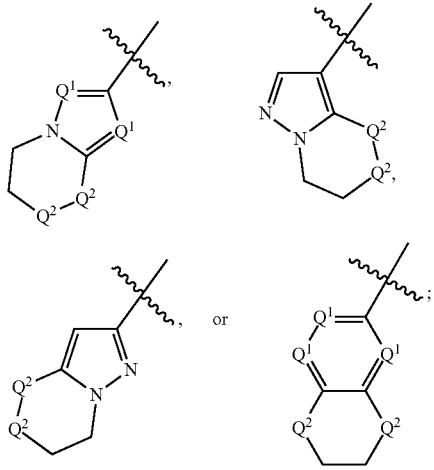

or each occurrence of $Q^1$ is independently N or CH, provided that at least one $Q^1$ is N;

each occurrence of $Q^2$ is independently O, S, $S(=O_2)$, $CH_2$, or $NR^{12}$, and $R^1$-$R^{12}$ and $R^a$ and $R^b$ are as defined in claim 1.

3. The compound of claim 2, having the structure of Formula (II):

(II)

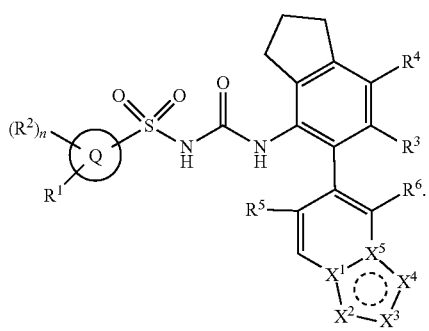

4. The compound of claim 3, wherein

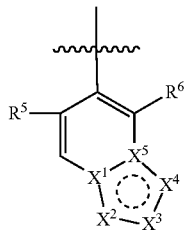

in Formula (II) is

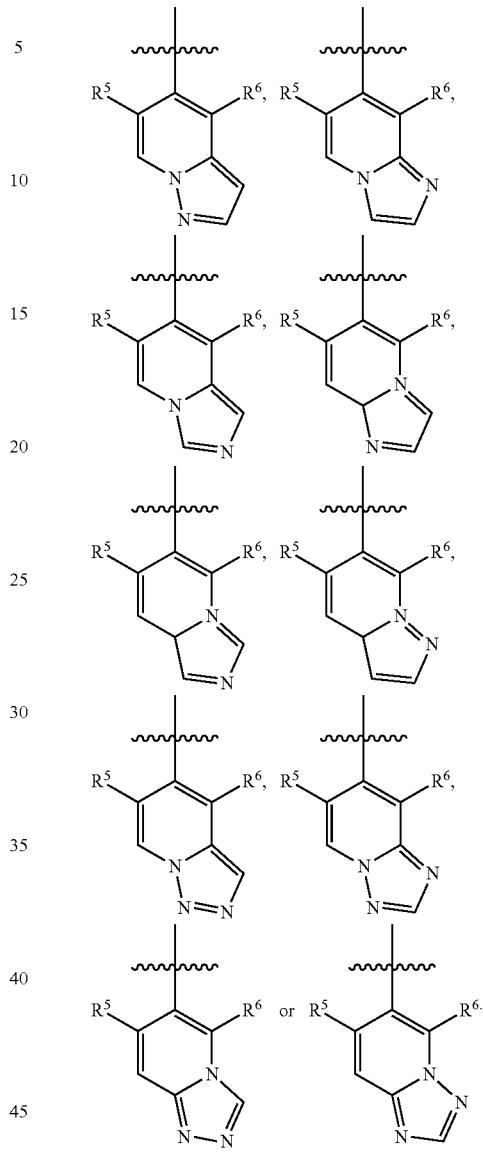

5. The compound of claim 2, having the structure of Formula (III):

(III)

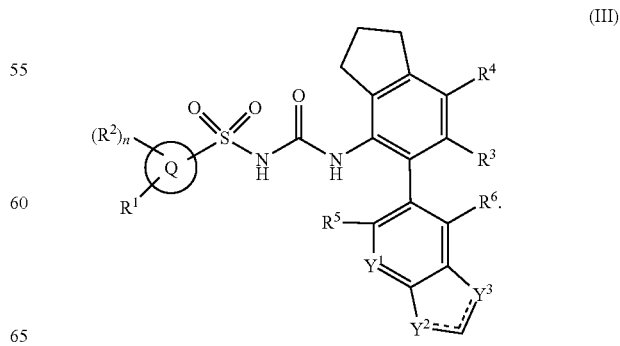

6. The compound of claim 5, wherein

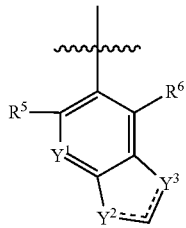

in Formula (III) is

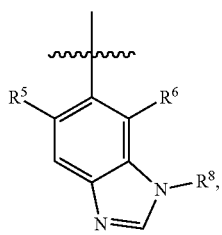 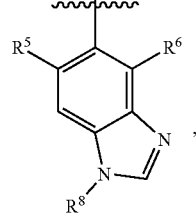

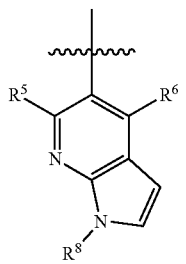 or 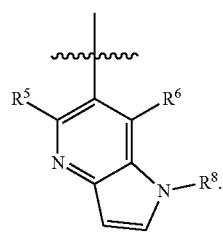

7. The compound of claim 2, having the structure of Formula (IV):

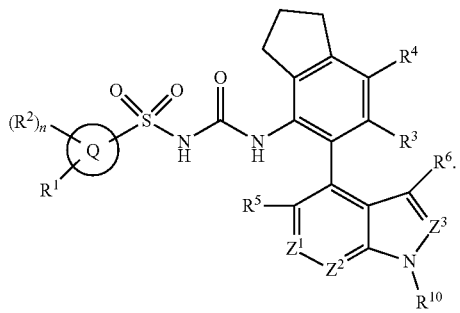

(IV)

8. The compound of claim 7, wherein

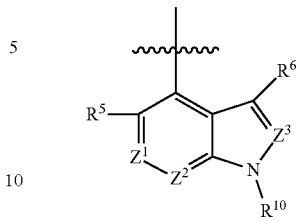

in Formula (IV) is

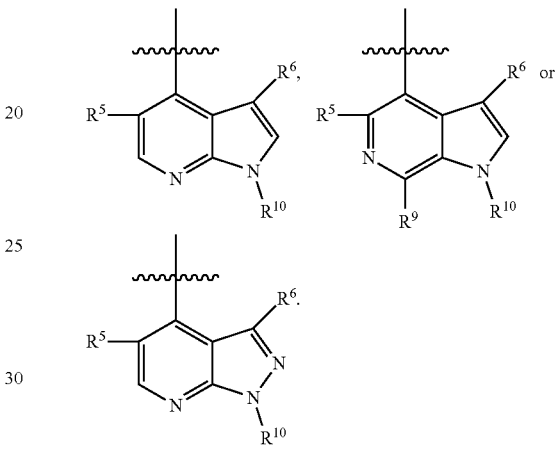

9. The compound of claim 2, wherein each occurrence of Ring Q together with $R^1$ and $R^2$ is independently selected from:

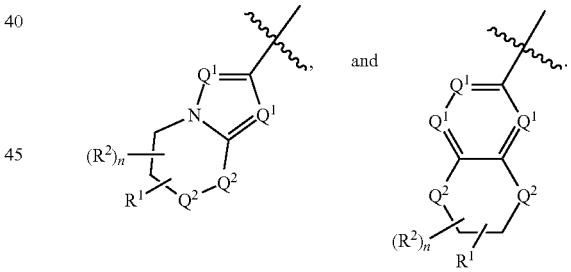

10. The compound of claim 2, wherein each occurrence of $Q^1$ is independently N or CH, provided that only one $Q^1$ is N per ring.

11. The compound of claim 1, wherein each occurrence of $R^1$ is independently $C_{1-4}$alkyl, halo$C_{1-4}$alkyl, $C_{3-5}$cycloalkyl, $C_{1-4}$alkoxy, $C_{3-5}$cycloalkoxy, $NR^aR^b$, or 4-6-membered heterocyclyl, each of which is optionally substituted with one to three $R^{11}$.

12. The compound of claim 1, wherein each occurrence of $R^2$ is independently hydrogen, $C_{1-4}$alkyl, halo$C_{1-4}$alkyl, $C_{3-5}$cycloalkyl, halogen, CN, OH, $C_{1-4}$alkoxy, $NR^aR^b$, or 4-6-membered heterocyclyl, each of which is optionally substituted with one to two $R^{11}$.

13. The compound of claim 1, wherein:
each occurrence of $R^3$ is hydrogen, methyl, F, or Cl;
each occurrence of $R^4$ is hydrogen, methyl or halogen;

each occurrence of $R^5$ is hydrogen or methyl;
each occurrence of $R^6$ is hydrogen or methyl;
each occurrence of $R^7$ is hydrogen or methyl;
each occurrence of $R^8$ is hydrogen or methyl; and/or
each occurrence of $R^9$ is hydrogen, methyl or methoxy.

14. The compound of claim 1, wherein each occurrence of $R^{10}$ is independently hydrogen, $C_{1-4}$alkyl, $C_{3-5}$cycloalkyl, or 4-6-membered heterocyclyl optionally substituted with $C_{1-4}$alkyl, in which the 4-6-membered heterocyclyl contains one to two heteroatoms selected from N, O and S;

each occurrence of $R^{11}$ is independently hydrogen, $C_{1-4}$alkyl, $C_{3-5}$cycloalkyl, halogen, CN, OH, $C_{1-4}$alkoxy, $C_{3-5}$cycloalkoxy, $NR^aR^b$, or 4-6-membered heterocyclyl, in which the 4-6-membered heterocyclyl contains one to two heteroatoms selected from N, O and S; and/or each occurrence of $R^{12}$ is independently hydrogen, $C_{1-4}$alkyl, halo$C_{1-4}$alkyl, $C_{3-5}$cycloalkyl, $C_{1-4}$alkyl-$C_{3-5}$cycloalkyl, $C_{1-4}$alkyl-$NR^aR^b$, $C(=O)R^a$, $C(=O)NR^aR^b$, or 4-6-membered heterocyclyl optionally substituted with one to three groups selected from $C_{1-4}$alkyl, halo$C_{1-4}$alkyl, $C_{3-5}$cycloalkyl, halogen, CN, OH, $C_{1-4}$alkoxy, $C_{3-5}$cycloalkoxy, or $NR^aR^b$, in which the 4-6-membered heterocyclyl contains one to two heteroatoms selected from N, O and S.

15. The compound of claim 1, selected from:

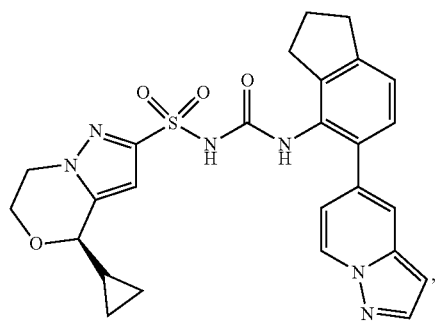

,

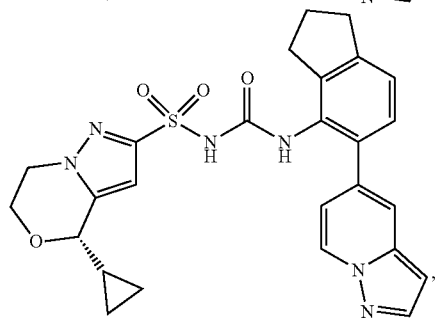

,

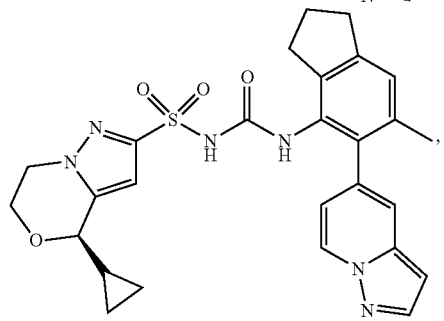

,

-continued

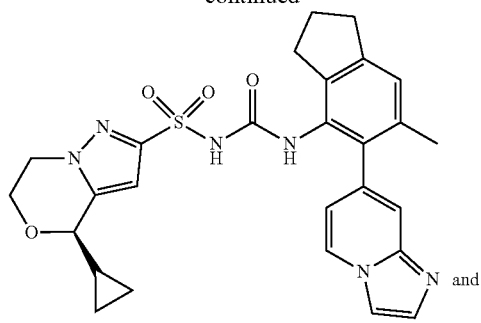

and

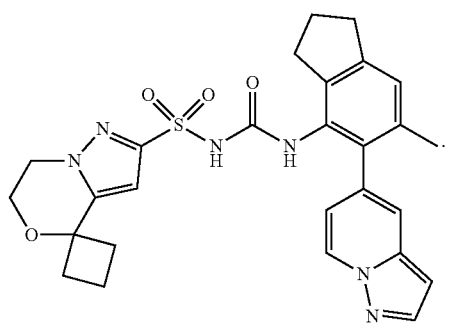

.

16. The compound of claim 1, selected from:

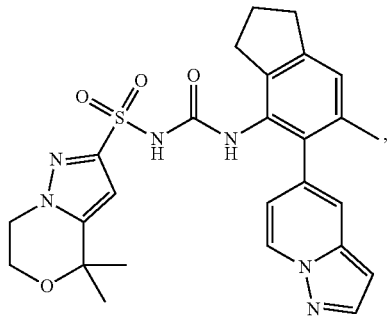

,

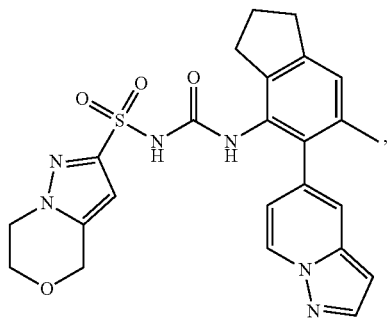

,

117
-continued

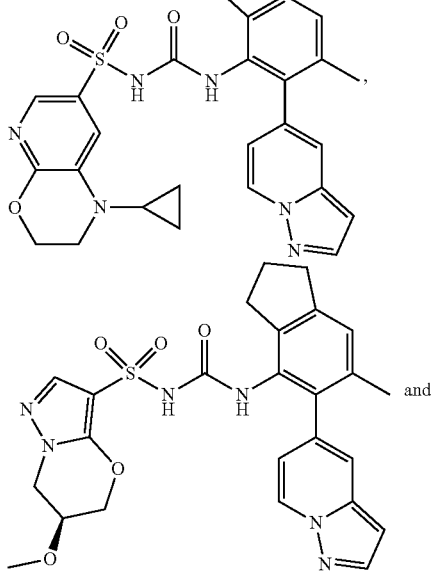

and

118
-continued

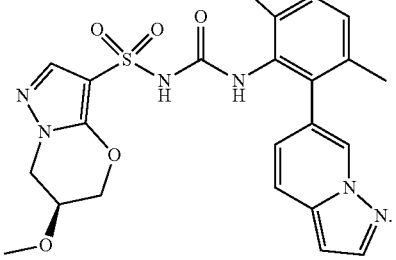

17. A pharmaceutical composition comprising the compound of claim 1, and a pharmaceutically acceptable carrier.

18. A method for treating a disease or condition which is responsive to inhibition of the NLRP3 in a subject in need thereof, comprising administering an effective amount of a compound of claim 1 to the subject.

19. The method of claim 18, wherein the disease is Cryopyrin-associated periodic syndrome, multiple sclerosis, Alzheimer's disease, Parkinson's disease, atherosclerosis, type 2 diabetes, gout flares or osteoarthritis.

* * * * *